(12) United States Patent
Ausubel et al.

(10) Patent No.: US 11,278,025 B2
(45) Date of Patent: Mar. 22, 2022

(54) ANTIBIOTIC COMPOUNDS

(71) Applicants: The General Hospital Corporation, Boston, MA (US); Rhode Island Hospital, A Lifespan-Partner, Providence, RI (US); Temple University-Of The Commonwealth System Of Higher Education, Philadelphia, PA (US)

(72) Inventors: Frederick M. Ausubel, Newton, MA (US); Wooseong Kim, Providence, RI (US); Eleftherios Mylonakis, Providence, RI (US); William M. Wuest, Atlanta, GA (US)

(73) Assignees: The General Hospital Corporation, Boston, MA (US); Rhode Island Hospital, A Lifespan-Partner, Providence, RI (US); Temple University-Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/614,251

(22) PCT Filed: May 17, 2018

(86) PCT No.: PCT/US2018/033232
§ 371 (c)(1),
(2) Date: Nov. 15, 2019

(87) PCT Pub. No.: WO2018/213609
PCT Pub. Date: Nov. 22, 2018

(65) Prior Publication Data
US 2020/0190009 A1 Jun. 18, 2020

Related U.S. Application Data

(60) Provisional application No. 62/648,912, filed on Mar. 27, 2018, provisional application No. 62/625,292, filed on Feb. 1, 2018, provisional application No. 62/507,754, filed on May 17, 2017.

(51) Int. Cl.
| | | |
|---|---|---|
| *C07C 65/11* | (2006.01) | |
| *C07C 65/17* | (2006.01) | |
| *A61P 31/04* | (2006.01) | |
| *A01N 31/08* | (2006.01) | |
| *C07C 39/17* | (2006.01) | |
| *C07C 235/66* | (2006.01) | |
| *A61K 45/06* | (2006.01) | |

(52) U.S. Cl.
CPC .............. *A01N 31/08* (2013.01); *A61P 31/04* (2018.01); *C07C 39/17* (2013.01); *C07C 65/11* (2013.01); *C07C 65/17* (2013.01); *C07C 235/66* (2013.01); *A61K 45/06* (2013.01); *C07C 2603/74* (2017.05)

(58) Field of Classification Search
CPC ......... C07C 65/11; C07C 65/17; C07C 39/17; A61P 31/04
See application file for complete search history.

(56) References Cited

U.S. PATENT DOCUMENTS

| | | |
|---|---|---|
| 4,200,738 A | 4/1980 | Hill et al. |
| 4,717,720 A * | 1/1988 | Shroot ................ A61Q 5/00 514/63 |
| 5,304,121 A | 4/1994 | Sahatjian |
| 5,602,104 A | 2/1997 | Shroot et al. |
| 5,886,026 A | 3/1999 | Hunter et al. |
| 6,099,562 A | 8/2000 | Ding |
| 6,127,415 A | 10/2000 | Pfahl et al. |
| 6,462,064 B1 | 10/2002 | Pfahl et al. |
| 7,014,866 B2 | 3/2006 | Infeld et al. |
| 8,101,793 B2 | 1/2012 | Merlini et al. |
| 2003/0055110 A1 | 3/2003 | Voegel et al. |
| 2006/0079502 A1 | 4/2006 | Lang |
| 2006/0094744 A1 | 5/2006 | Maryanoff et al. |
| 2010/0076219 A1 | 3/2010 | Kavinsh et al. |

FOREIGN PATENT DOCUMENTS

| | | |
|---|---|---|
| WO | WO 1998/001132 | 1/1998 |
| WO | WO 2016/196964 | 12/2016 |

OTHER PUBLICATIONS

Allison et al., "Metabolite-enabled eradication of bacterial persisters by aminoglycosides," Nature, May 2011, 473(7346):216-220.
Altucci et al., "RAR and RXR modulation in cancer and metabolic disease," Nat. Rev. Drug Discov., Oct. 2007, 6(10):793-810.
Baba et al., "Genome and virulence determinants of high virulence community-acquired MRSA," The Lancet, May 2002, 359(9320):1819-1827.
Baddour et al., "Infective endocarditis in adults: diagnosis, antimicrobial therapy, and management of complications: a scientific statement for healthcare professionals from the American Heart Association," Circulation, Oct. 2015, 132(15):1435-1486.
Beanan & Strome, "Characterization of a germ-line proliferation mutation in C. elegans," Development, Nov. 1992, 116(3):755-766.
Berger et al., "Molecular dynamics simulations of a fluid bilayer of dipalmitoylphosphatidylcholine at full hydration, constant pressure, and constant temperature," Biophys. J., May 1997, 72(5):2002-2013.
Buchholtz et al., "Severity of gentamicin's nephrotoxic effect on patients with infective endocarditis: a prospective observational cohort study of 373 patients," Clin. Infect. Dis., Jan. 2009, 48(1):65-71.
Carias et al., "Genetic linkage and cotransfer of a novel, vanB-containing transposon (Tn5382) and a low-affinity penicillin-binding protein 5 gene in a clinical vancomycin-resistant Enterococcus faecium isolate," J. Bacteriol., Sep. 1998, 180(17):4426-4434.
Cassat et al., "Investigation of biofilm formation in clinical isolates of *Staphylococcus aureus*," Methods Mol. Biol., 2007, 391:127-144.

(Continued)

*Primary Examiner* — Jeffrey S Lundgren
*Assistant Examiner* — Chris E Simmons
(74) *Attorney, Agent, or Firm* — Fish & Richardson P.C.

(57) ABSTRACT

The present application provides compounds and methods of treating bacterial infection, including bacterial infection caused by *P. acnes*.

7 Claims, 23 Drawing Sheets

(56) References Cited

OTHER PUBLICATIONS

Chen et al., "Interaction of daptomycin with lipid bilayers: a lipid extracting effect," Biochemistry, Aug. 2014, 53(33):5384-5392.
Conlon et al., "Activated ClpP kills persisters and eradicates a chronic biofilm infection," Nature, Nov. 2013, 503(7476):365-370.
Conlon et al., "Persister formation in Staphylococcus aureus is associated with ATP depletion," Nature Microbiology, May 2016, 1(5):16051, 7 pages.
Cosgrove et al., "Initial low-dose gentamicin for Staphylococcus aureus bacteremia and endocarditis is nephrotoxic," Clin. Infect. Dis. Mar. 2009, 48(6):713-721.
Creighton et al., "Three-dimensional graphene-based microbarriers for controlling release and reactivity in colloidal liquid phases," ACS Nano, Feb. 2016, 10(2):2268-2276.
Cui et al., "Disruption of membrane by colistin kills uropathogenic Escherichia coli persisters and enhances killing of other antibiotics," Antimicrob. Agents Chemother., Nov. 2016, 60(11):6867-6871.
Cui et al., "DNA microarray-based identification of genes associated with glycopeptide resistance in Staphylococcus aureus," Antimicrob. Agents Chemother., Aug. 2005, 49(8):3404-3413.
Davies & Davies, "Origins and evolution of antibiotic resistance," Microbiol. Mol. Biol. Rev., Sep. 2010, 74(3):417-433.
Dunn et al., "Hepatocyte function and extracellular matrix geometry: long-term culture in a sandwich configuration," FASEB J., Feb. 1989, 3(2):174-177.
Dunn et al., "Hepatocytes in collagen sandwich: evidence for transcriptional and translational regulation," J. Cell Biol., Feb. 1992, 116(4):1043-1053.
Elbaz & Ben-Yehuda, "The metabolic enzyme ManA reveals a link between cell wall integrity and chromosome morphology," PLoS Genet., Sep. 2010, 6(9):e1001119, 12 pages.
Engman et al., "The YjbH adaptor protein enhances proteolysis of the transcriptional regulator Spx in Staphylococcus aureus," J. Bacteriol., Mar. 2012, 194(5):1186-1194.
Falord et al., "Investigation of the Staphylococcus aureus GraSR regulon reveals novel links to virulence, stress response and cell wall signal transduction pathways," PLoS One, Jul. 2011, 6(7):e21323, 17 pages.
Farha et al., "Collapsing the proton motive force to identify synergistic combinations against Staphylococcus aureus," Chemistry & Biology, Sep. 2013, 20(9):1168-1178.
Fey et al., "A genetic resource for rapid and comprehensive phenotype screening of nonessential Staphylococcus aureus genes," Mbio, Mar. 2013, 4(1):e00537-12, 8 pages.
Freireich et al., "Quantitative comparison of toxicity of anticancer agents in mouse, rat, hamster, dog, monkey, and man," Cancer Chemother. Rep, May 1966, 50(4): 219-244.
Friedman et al., "Genetic changes that correlate with reduced susceptibility to daptomycin in Staphylococcus aureus," Antimicrob. Agents Chemother., Apr. 2006, 50(4):2137-2145.
Friedrich et al., "Antibacterial action of structurally diverse cationic peptides on Gram-positive bacteria," Antimicrob. Agents Chemother., Aug. 2000, 44(8):2086-2092.
Ganewatta et al., "Bio-inspired resin acid-derived materials as anti-bacterial resistance agents with unexpected activities," Chem. Sci., 2014, 5(5):2011-2016.
García-Solache et al., "Genome sequence of the multiantibiotic-resistant Enterococcus faecium Strain C68 and insights on the pLRM23 colonization plasmid," Genome Announc., Jun. 2016, 4(3):e01719-15.
Garsin et al., "A simple model host for identifying Gram-positive virulence factors," Proc. Natl. Acad. Sci. U.S.A., Sep. 2001, 98(19):10892-10897.
Göhring et al., "New role of the disulfide stress effector YjbH in β-lactam susceptibility of Staphylococcus aureus," Antimicrob. Agents Chemother., Dec. 2011, 55(12):5452-5458.
Hess et al., "GROMACS 4: algorithms for highly efficient, load-balanced, and scalable molecular Simulation," J. Chem. Theory Comput., Mar. 2008, 4(3):435-447.
Hub et al.,. "g_wham—a free weighted histogram analysis implementation including robust error and autocorrelation estimates," J. Chem. Theory Comput., Nov. 2010, 6(12):3713-3720.
Hurdle et al., "Targeting bacterial membrane function: an underexploited mechanism for treating persistent infections," Nat. Rev. Microbiol. Jan. 2011, 9(1):62-75.
International Preliminary Report on Patentability in PCT Appln. No. PCT/US2018/033232, dated Nov. 19, 2019, 7 pages.
Irby et al., "A review of adapalene in the treatment of acne vulgaris," J. Adolesc. Health, Nov. 2008, 43(5):421-424.
Isralewitz et al., "Steered molecular dynamics and mechanical functions of proteins," Curr. Opin. Struct. Biol., Apr. 2001, 11(2):224-230.
Joshi et al., "N-terminal aromatic tag induced self assembly of tryptophan-arginine rich ultra short sequences and their potent antibacterial activity," RSC Advances, 2015, 5(84):68610-68620.
Kamentsky et al., "Improved structure, function and compatibility for CellProfiler: modular high-throughput image analysis software," Bioinformatics, Feb. 2011, 27(8):1179-1180.
Kemnitz & Loewen, "Amide Resonance' Correlates with a Breadth of C—N Rotation Barriers," J. Am. Chem. Soc., Feb. 2007, 129(9)::2521-2528.
Kim et al., "A new class of synthetic retinoid antibiotics effective against bacterial persisters," Nature, Apr. 2018, 556(7699):103, 19 pages.
Kim et al., "Identification of an antimicrobial agent effective against methicillin-resistant Staphylococcus aureus persisters using a fluorescence-based screening strategy," PLoS One, 2015, 10(6):e0127640.
Kim et al., "NH125 kills methicillin-resistant Staphylococcus aureus persisters by lipid bilayer disruption," Future Med. Chem., Mar. 2016, 8(3):257-269.
Kumar et al., "The weighted histogram analysis method for free-energy calculations on biomolecules I. The method," J. Comput. Chem., Oct. 1992, 13(8):1011-1021.
Lee et al., "Process of inducing pores in membranes by melittin," Proc. Natl. Acad. Sci. U.S.A., Aug. 2013, 110(35):14243-14248.
Lehar et al., "Novel antibody-antibiotic conjugate eliminates intracellular S. aureus," Nature, Nov. 2015, 527(7578):323-328.
Lew & Waldvogel, "Osteomyelitis," The Lancet, Jul. 2004, 364:369-379.
Liu & Xiang, "A high yield and pilot-scale process for the preparation of adapalene," Org. Process Res. Dev., Mar. 2006, 10(2):285-288.
Liu et al., "Clinical practice guidelines by the Infectious Diseases Society of America for the treatment of methicillin-resistant Staphylococcus aureus infections in adults and children," Clin. Infect. Dis., Feb. 2011, 52(3):e18-e55.
Malde et al., "An automated force field topology builder (ATB) and repository: version 1.0,". J. Chem. Theory. Comput., Nov. 2011, 7(12)4026-4037.
Mao et al. 'Synthesis of Benzyl-, Allyl-, and Allenyl-boronates via Copper-Catalyzed Borylation of Alcohols', Organic Letters, Feb. 16, 2017 (Feb. 16, 2017), vol. 19, pp. 1204-1207; p. 1205.
Maron & Ames, "Revised methods for the Salmonella mutagenicity test," Mutat. Res., May 1983, 113(3-4):173-215.
Meehl et al., "Interaction of the GraRS two-component system with the VraFG ABC transporter to support vancomycin-intermediate resistance in Staphylococcus aureus," Antimicrob. Agents Chemother., Aug. 2007, 51(8):2679-2689.
Milner-White, "The partial charge of the nitrogen atom in peptide bonds," Protein Sci., Nov. 1997, 6(11):2477-2482.
Monk et al., "Transforming the untransformable: application of direct transformation to manipulate genetically Staphylococcus aureus and Staphylococcus epidermidis," Mbio, May 2012, 3(2):e00277-11.
Moy et al., "High-throughput screen for novel antimicrobials using a whole animal infection model," ACS Chem. Biol., Jun. 2009, 4(7):527-533.

(56) References Cited

OTHER PUBLICATIONS

Neoh et al., "Mutated response regulator graR is responsible for phenotypic conversion of *Staphylococcus aureus* from heterogeneous vancomycin-intermediate resistance to vancomycin-intermediate resistance," Antimicrob. Agents Chemother., Jan. 2008, 52(1):45-53.
Odds, "Synergy, antagonism, and what the chequerboard puts between them," J. Antimicrob. Chemother. Jul. 2003, 52(1):1-1.
PCT International Search Report and Written Opinion in International Appln. No. PCT/US18/33232, dated Oct. 4, 2018, 15 pages.
Piggot et al., "Electroporation of the *E. coli* and *S. aureus* membranes: molecular dynamics simulations of complex bacterial membranes," J. Phys. Chem. B, Oct. 2011, 115(45):13381-13388.
Rahme et al., "Common virulence factors for bacterial pathogenicity in plants and animals," Science, Jun. 1995, 268(5219):1899-1902.
Rajamuthiah et al., "A defensin from the model beetle *Tribolium castaneum* acts synergistically with telavancin and daptomycin against multidrug resistant *Staphylococcus aureus*," PLoS One, Jun. 2015, 10(6):e0128576.
Rajamuthiah et al., "Whole animal automated platform for drug discovery against multi-drug resistant *Staphylococcus aureus*," PLoS One, Feb. 2014, 9(2):e89189.
Rice et al., "Enterococcus faecium low-affinity pbp5 is a transferable determinant," Antimicrob. Agents Chemother., Dec. 2005, 49(12):5007-5012.
Schmid et al., "Definition and testing of the GROMOS force-field versions 54A7 and 54B7," Eur. Biophys. J., Jul. 2011, 40(7):843-856.
Sharma et al., "Metabolic profiling based quantitative evaluation of hepatocellular metabolism in presence of adipocyte derived extracellular matrix," PLoS One, May 2011, 6(5):e20137.
Sharma-Kuinkel et al., "The *Staphylococcus aureus* LytSR two-component regulatory system affects biofilm formation," J. Bacteriol., Aug. 2009, 191(15):4767-4775.
Shimono et al., "Potent inhibition of heterotopic ossification by nuclear retinoic acid receptor-γ agonists," Nat. Med., Apr. 2011, 17(4):454-460.
Smith et al., "New insights into Acinetobacter baumannii pathogenesis revealed by high-density pyrosequencing and transposon mutagenesis," Genes Dev., Mar. 2007, 21(5):601-614.
Tan et al., "Killing of Caenorhabditis elegans by Pseudomonas aeruginosa used to model mammalian bacterial pathogenesis," Proc. Natl. Acad. Sci. U.S.A., Jan. 1999, 96(2):715-720.
Tanaka-Hino et al., "SEK-1 MAPKK mediates Ca2+ signaling to determine neuronal asymmetric development in Caenorhabditis elegans," EMBO Reports, Jan. 2002, 3(1):56-62.
Tang et al., "Combination of bexarotene and the retinoid CD1530 reduces murine oral-cavity carcinogenesis induced by the carcinogen 4-nitroquinoline 1-oxide," Proc. Natl. Acad. Sci. U.S.A., Jun. 2014, 111(24):8907-8912.
Thorisdottir et al., "IS6770, an enterococcal insertion-like sequence useful for determining the clonal relationship of clinical enterococcal isolates," J. Infect. Dis., Dec. 1994, 170(6):1539-1548.
Tong et al., "*Staphylococcus aureus* infections: epidemiology, pathophysiology, clinical manifestations, and management," Clin. Microbiol. Rev., Jul. 2015, 28(3):603-661.
Tu et al., "Destructive extraction of phospholipids from *Escherichia coli* membranes by graphene nanosheets," Nat. Nanotechnol., Aug. 2013, 8(8):594-601.
Valli et al., "Atypical retinoids ST1926 and CD437 are S-phase-specific agents causing DNA double-strand breaks: significance for the cytotoxic and antiproliferative activity," Mol. Cancer Ther., Aug. 2008, 7(9)2941-2954.
Weigel et al., "Genetic analysis of a high-level vancomycin-resistant isolate of *Staphylococcus aureus*," Science, Nov. 2003, 302(5650):1569-1571.
Williams & Hanson, "Synthesis of substituted asymmetrical biphenyl amino esters as alpha helix mimetics," Tetrahedron, Jul. 2012, 68(27-28):5406-5414.
Yang et al., "The *Staphylococcus aureus* two-component regulatory system, GraRS, senses and confers resistance to selected cationic antimicrobial peptides," Infect. Immun., Jan. 2012, 80(1):74-81.
Zhu et al., "Nanomechanical mechanism for lipid bilayer damage induced by carbon nanotubes confined in intracellular vesicles," Proc. Natl. Acad. Sci. U.S.A., Nov. 2016, 113(44):12374-12379.
Keren et al., "Persister cells and tolerance to antimicrobials," FEMS Microbiol. Lett., Jan. 2004, 230(1):13-18.
Owton et al., "tert-Butyl 3-Carboxyethyl-3-phosphonodiethylpropionate. A Novel Reagent for Stobbe-Like Condensations," Synth. Commun., Aug. 1993, 23(15):2119-2125.
Tietze et al., "Synthesis of a novel pentagastrin-drug conjugate for a targeted tumor therapy," Chem. Eur. J., Mar. 2008, 14(9):2811-2818.

\* cited by examiner

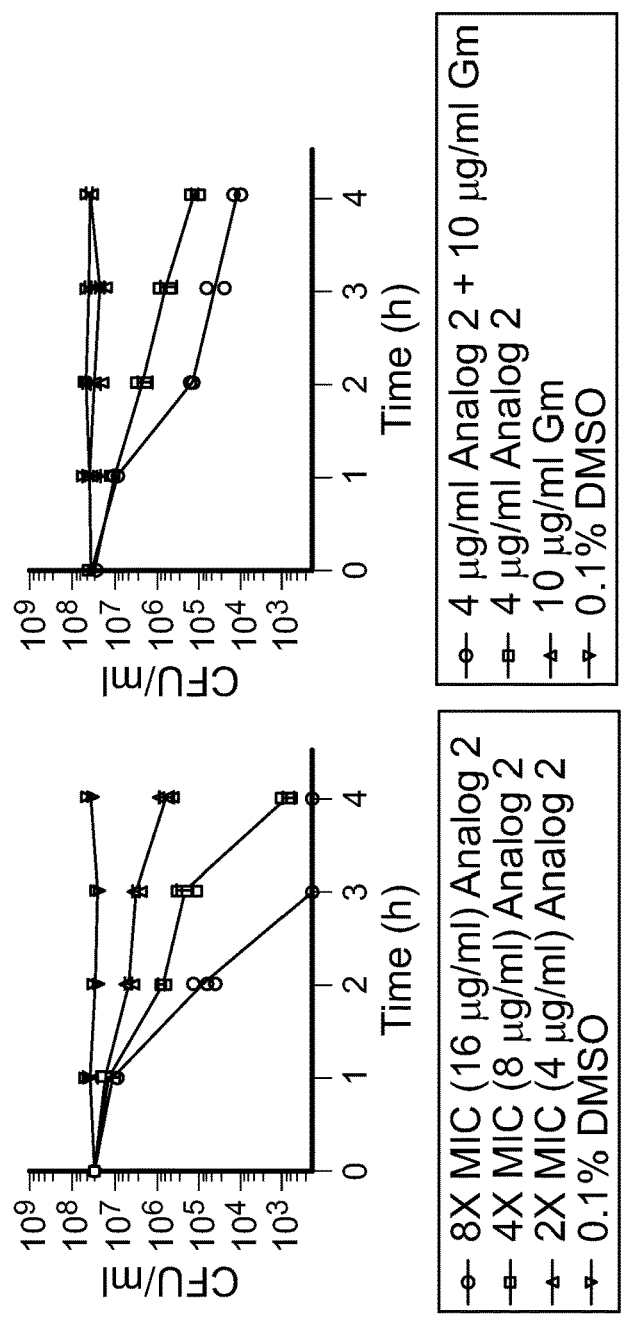
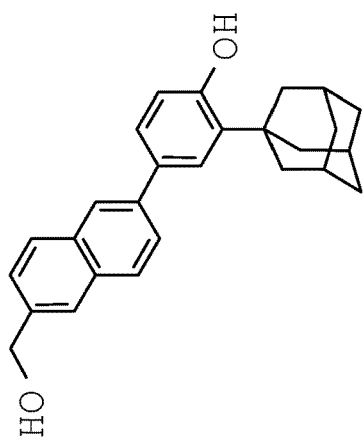
FIG. 2A
FIG. 2B

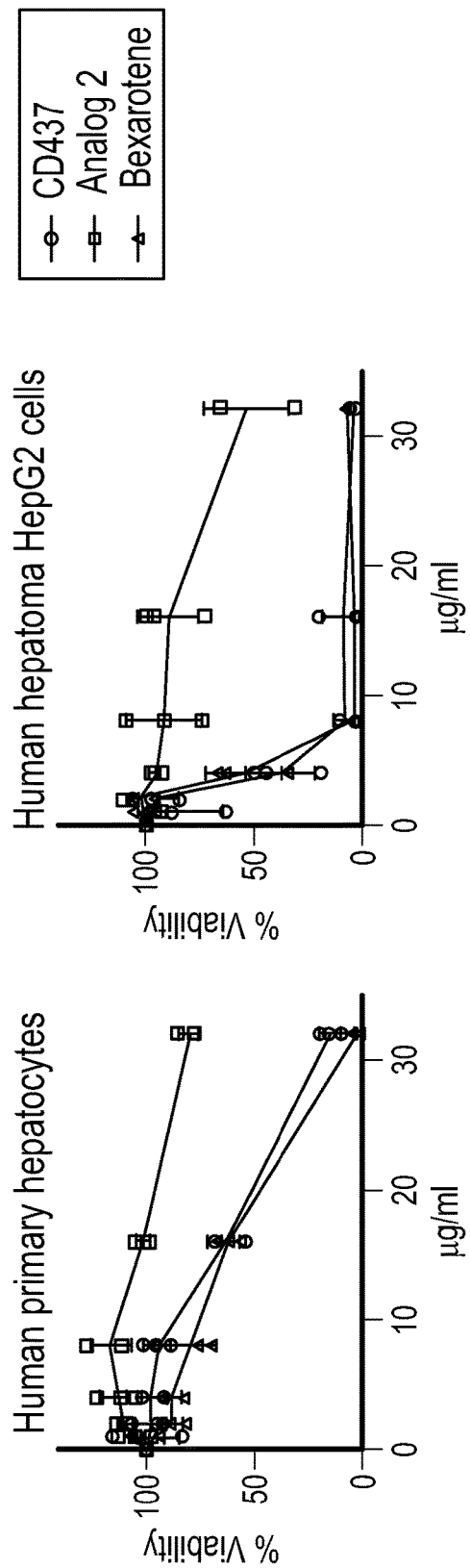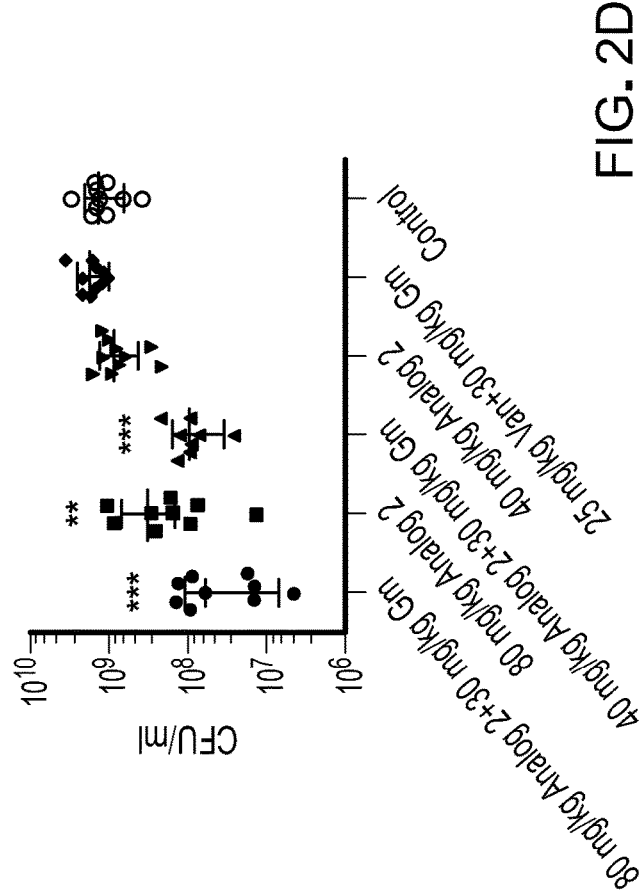
FIG. 2C
FIG. 2D

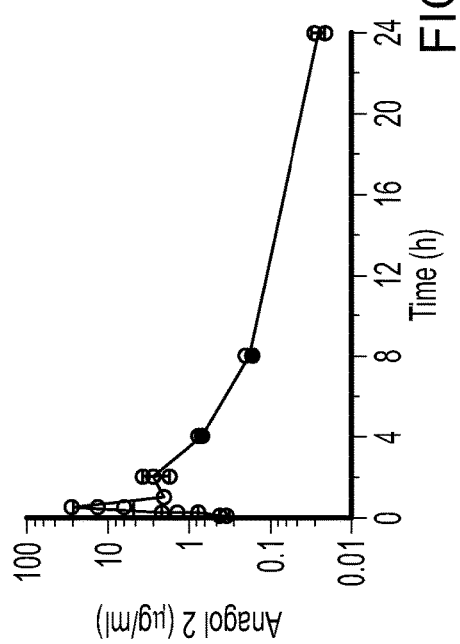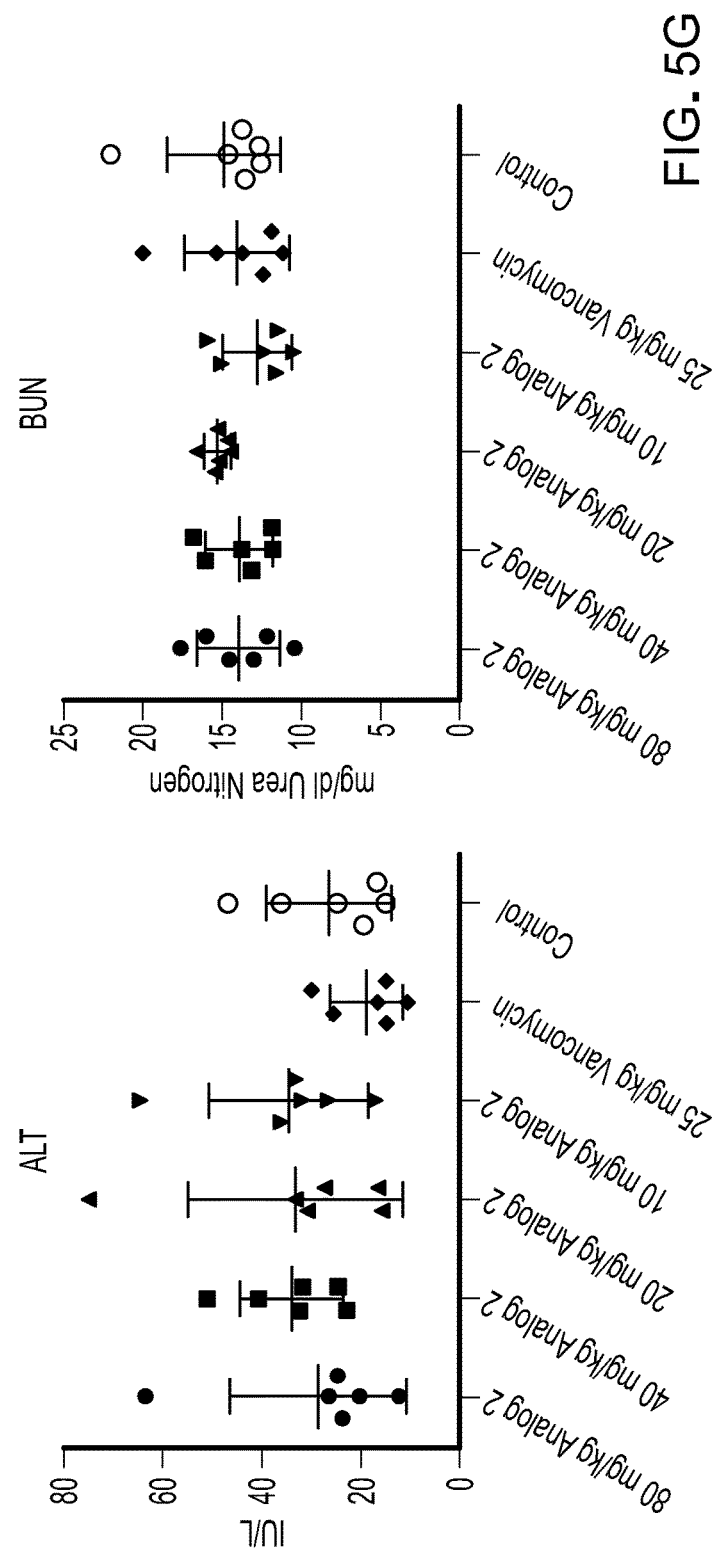

CD437

O2: −0.315e  O3: −0.367e
H1: 0.245e   C4: 0.437e

Analog 3

N3: −0.432e      O4: −0.383e
H1(H2): 0.226e   C5: 0.363e

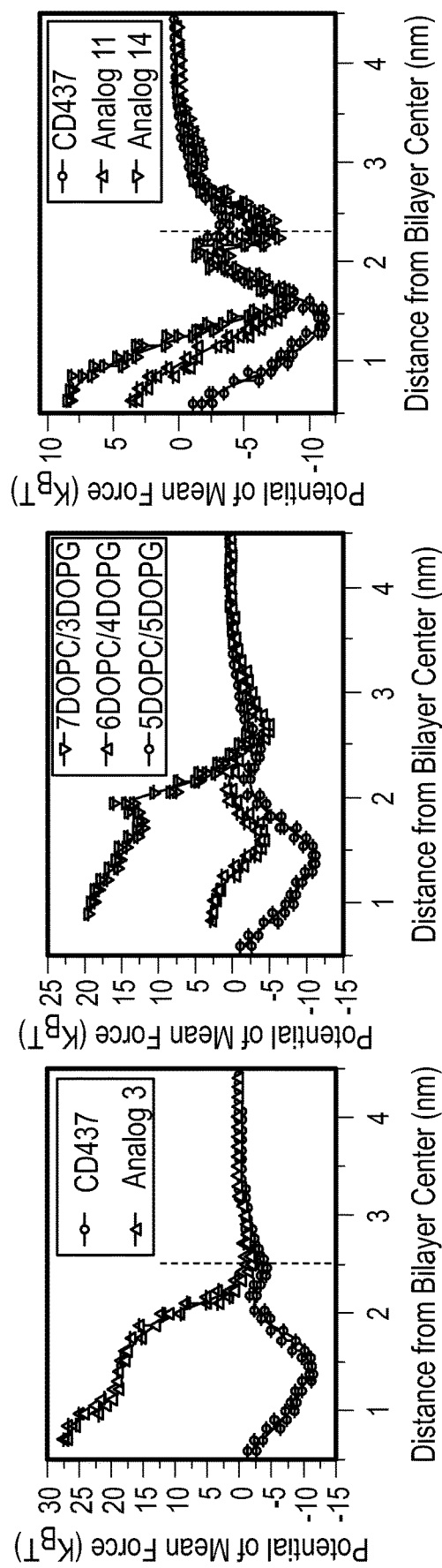
FIG. 6B
FIG. 6C
FIG. 6D
FIG. 6E

| Compounds | MIC (ug/mL) |
|---|---|
| Adapalene | >64 |
| CD437 | 2 |
| CD1530 | 2 |
| Analogue 2 | 8 |
| Adarotene | 4 |
| Tetracycline | 1 |

FIG. 8

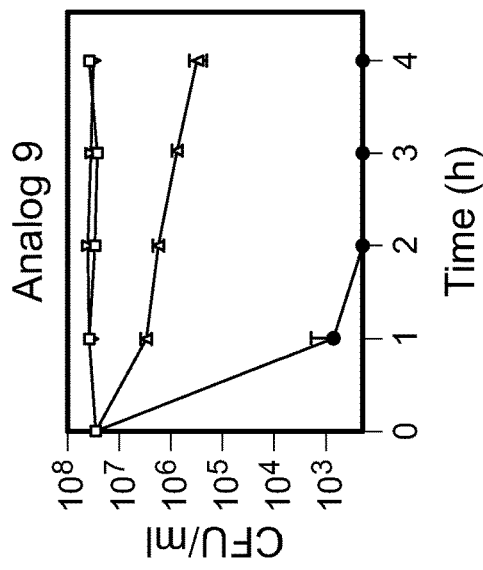
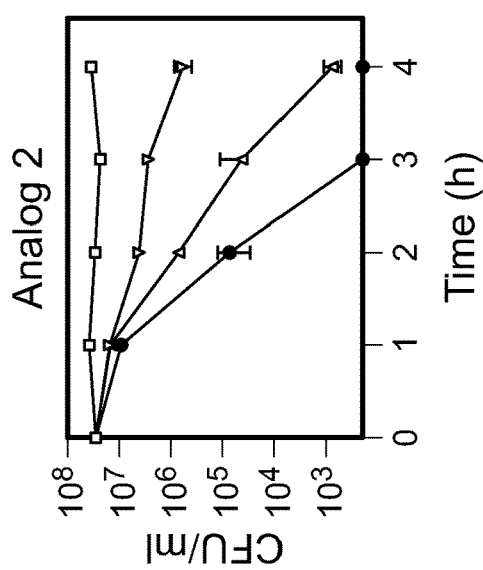
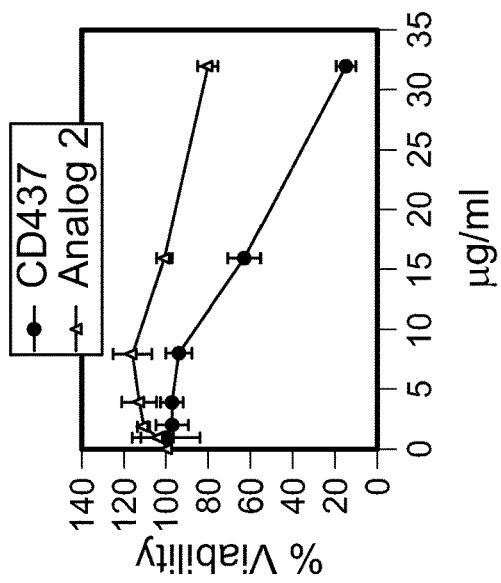
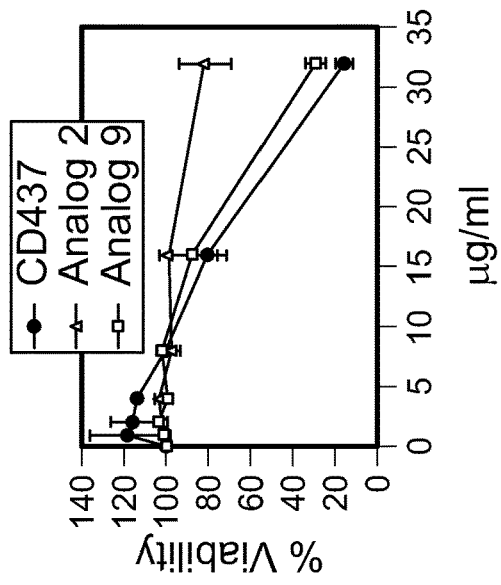
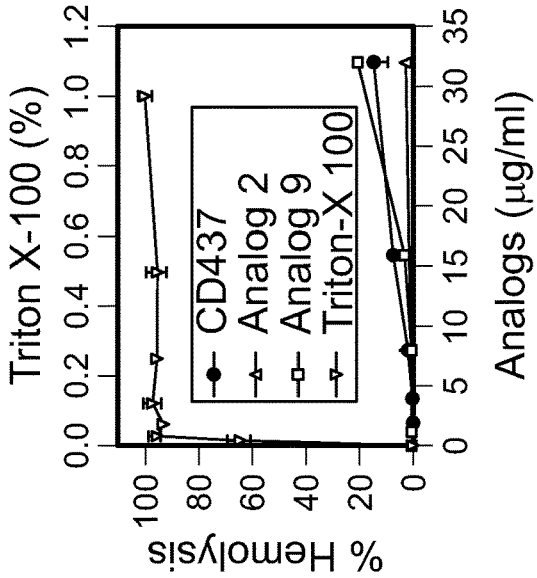
FIG. 9A
FIG. 9B
FIG. 9C
FIG. 9D

ANTIBIOTIC COMPOUNDS

CLAIM OF PRIORITY

This application is a national stage application of PCT/US2018/033232, filed May 17, 2018, which claims priority to U.S. patent application Ser. No. 62/648,912, filed on Mar. 27, 2018; U.S. patent application Ser. No. 62/625,292, filed on Feb. 1, 2018; and U.S. patent application Ser. No. 62/507,754, filed on May 17, 2017, the entire contents of which are hereby incorporated by reference.

FEDERALLY SPONSORED RESEARCH OR DEVELOPMENT

This invention was made with Government support under Grant No. P01 AI083214 awarded by the National Institutes of Health, and Grant No. 1R35GM119426 awarded by National Institute of General Medical Sciences. The Government has certain rights in the invention.

TECHNICAL FIELD

This invention relates to compounds useful in treating bacterial infections.

BACKGROUND

*S. aureus* and *Enterococcus* species have emerged as significant Gram-positive bacterial pathogens, presenting drug resistant strains such as methicillin resistant *S. aureus* (MRSA), vancomycin resistant *S. aureus* (VRSA), and vancomycin resistant *Enterococcus* (VRE). In 2005, 94,000 life-threating infections were attributed to *S. aureus*. Like MRSA, VRE has also become an important nosocomial pathogen, causing outbreaks in hospitals all over the world. VRE has been documented to colonize patients in dialysis units, neonatal units, hematology/oncology wards, and liver transplant units. The current arsenal of drugs is not sufficient to treat these infections.

SUMMARY

Despite the potential advantages of membrane-active antimicrobials such as the retinoids described here-including fast killing, low probability of developing resistance, and anti-persister activity—the major obstacle for developing retinoids as therapeutics is their potential cytotoxicity. The present disclosure provides membrane-active synthetic retinoids that are relatively selective for bacterial membranes, exhibit a high level of activity towards MRSA persister cells, and improved cytotoxicity profiles when compared to conventional synthetic retinoids.

In a first general aspect, the present disclosure provides a compound of Formula (I):

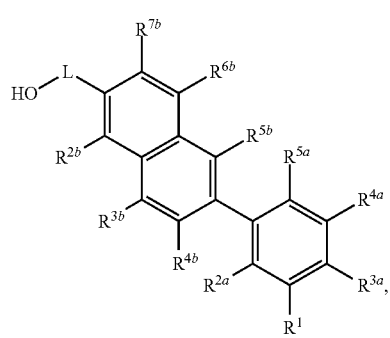

(I)

or a pharmaceutically acceptable salt thereof, wherein:

L is $C_{1-3}$ alkylene;

$R^1$ is selected from any one of the following moieties:

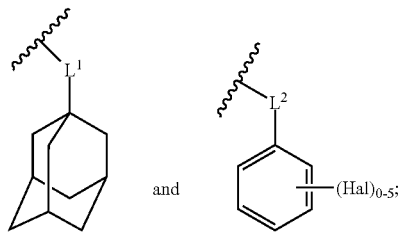

$L^1$ is $C_{1-3}$ alkylene, or $L^1$ is absent;

$L^2$ is $C_{1-3}$ alkylene;

each Hal is independently a halogen;

$R^{2a}$, $R^{3a}$, $R^{4a}$, and $R^{5a}$ are each independently selected from H and OH; provided that at least one of $R^{2a}$, $R^{3a}$, $R^{4a}$, and $R^{5a}$ is OH; and $R^{2b}$, $R^{3b}$, $R^{4b}$, $R^{5b}$, $R^{6b}$, and $R^{7b}$ are each independently selected from H, HO—$C_{1-3}$ alkylene, and —C(=O)OH.

Certain implementations of the first general aspect are described below:

In some embodiments, the compound of Formula (I) has any one of the following formulae:

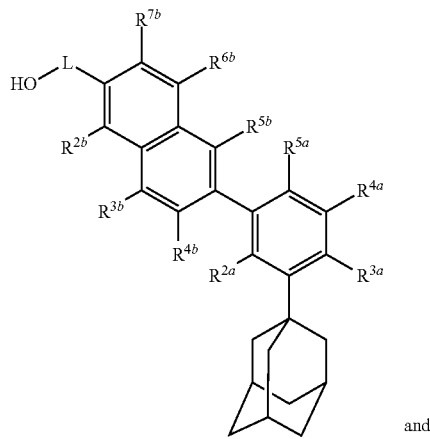

and

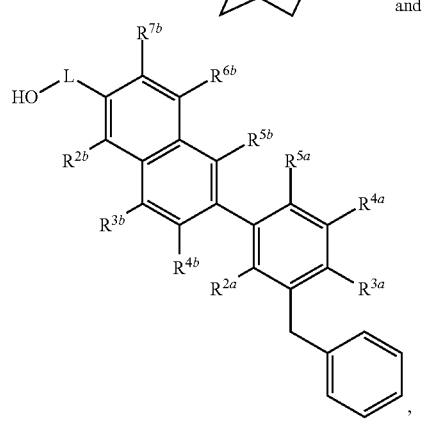

or a pharmaceutically acceptable salt thereof.

In some embodiments, the compound of Formula (I) has any one of the following formulae:

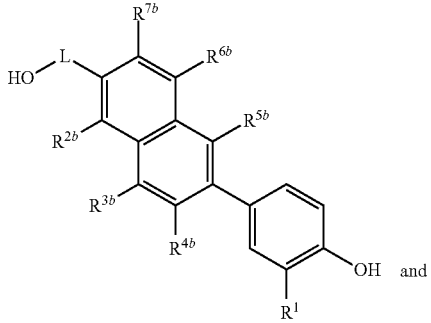

and

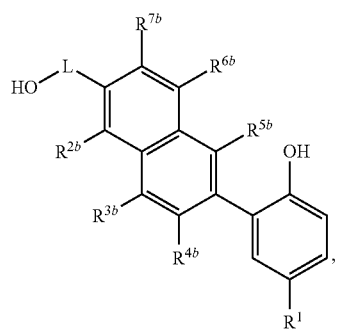

or a pharmaceutically acceptable salt thereof.

In some embodiments, $R^{2b}$, $R^{3b}$, $R^{4b}$, $R^{5b}$, $R^{6b}$, and $R^{7b}$ are each independently selected from H and —C(=O)OH.

In some embodiments, at least one of $R^{2b}$, $R^{3b}$, $R^{4b}$, $R^{5b}$, $R^{6b}$, and $R^{7b}$ is —C(=O)OH.

In some embodiments, each of $R^{2b}$, $R^{3b}$, $R^{4b}$, $R^{5b}$, $R^{6b}$, and $R^{7b}$ is H.

In some embodiments, L is methylene.

In some embodiments, the compound of Formula (I) is:

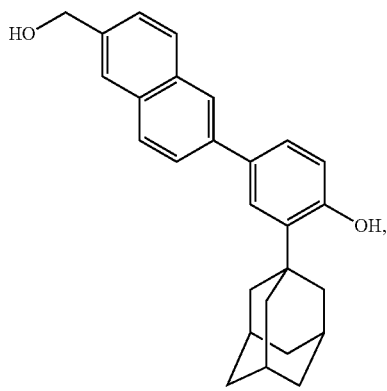 [SMILES: OCc1ccc2cc(-c3ccc(O)c(C45CC6CC(CC(C6)C4)C5)c3)ccc2c1]

or a pharmaceutically acceptable salt thereof.

In a second general aspect, the present disclosure provides a compound of Formula (II):

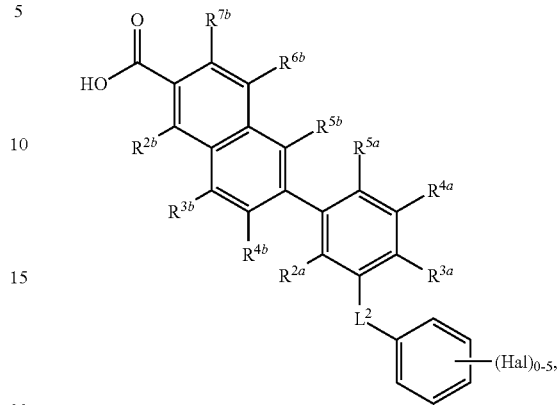

(II)

or a pharmaceutically acceptable salt thereof, wherein:
$L^2$ is $C_{1-3}$ alkylene;
each Hal is independently a halogen;
$R^{2a}$, $R^{3a}$, $R^{4a}$, and $R^{5a}$ are each independently selected from H and OH;
provided that at least one of $R^{2a}$, $R^{3a}$, $R^{4a}$, and $R^{5a}$ is OH; and
$R^{2b}$, $R^{3b}$, $R^{4b}$, $R^{5b}$, $R^{6b}$, and $R^{7b}$ are each independently selected from H, OH, HO—$C_{1-3}$ alkylene, and —C(=O)OH.

Certain implementations of the second general aspect are described below:

In some embodiments, the compound of Formula (II) has any one of the following formulae:

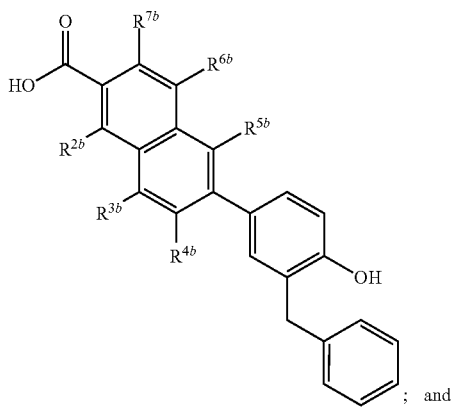

; and

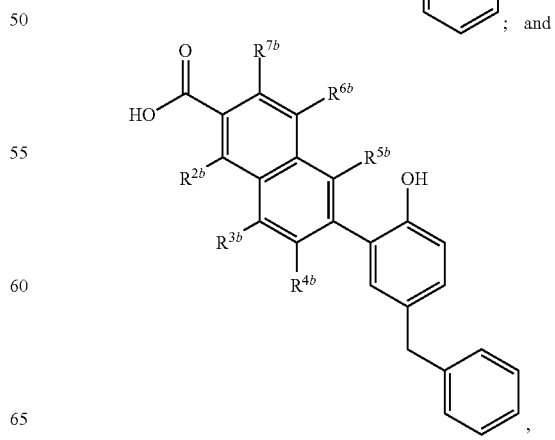

, or pharmaceutically acceptable salt thereof.

In some embodiments, $R^{2b}$, $R^{3b}$, $R^{4b}$, $R^{5b}$, $R^{6b}$, and $R^{7b}$ are each independently selected from H, OH, and —C(=O)OH.

In some embodiments, $R^{2b}$, $R^{3b}$, $R^{4b}$, $R^{5b}$, $R^{6b}$, and $R^{7b}$ are each independently selected from H and OH.

In some embodiments, the compound of Formula (II) is selected from:

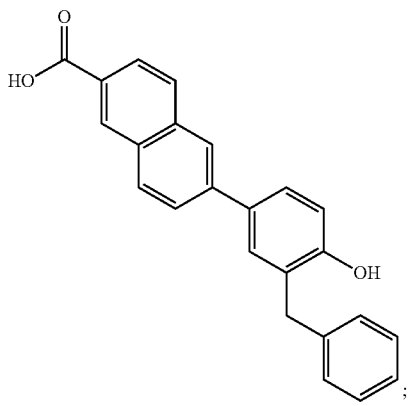

;

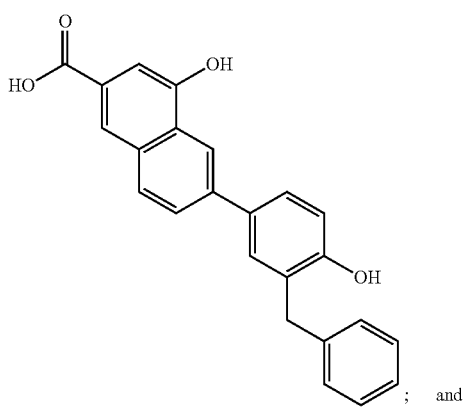

; and

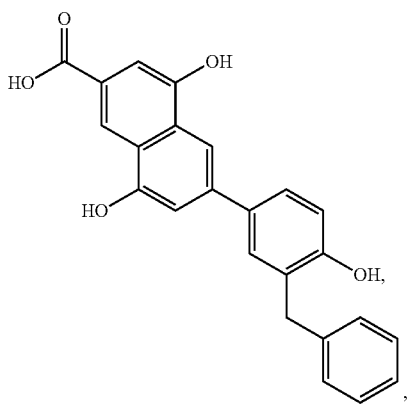

, or a pharmaceutically acceptable salt thereof.

In a third general aspect, the present disclosure provides a compound of Formula (III)

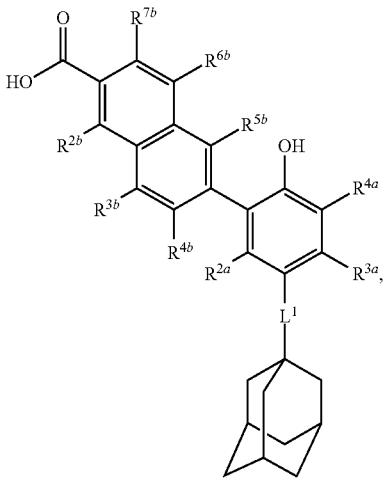

(III)

or a pharmaceutically acceptable salt thereof, wherein:

$L^1$ is $C_{1-3}$ alkylene, or $L^1$ is absent;

$R^{2a}$, $R^{3a}$, and $R^{4a}$ are each independently selected from H and OH; and $R^{2b}$, $R^{3b}$, $R^{4b}$, $R^{5b}$, $R^{6b}$, and $R^{7b}$ are each independently selected from H, OH, HO—$C_{1-3}$ alkylene, and —C(=O)OH.

Certain implementations of the third general aspect are described below.

In some embodiments, the compound of Formula (III) has formula:

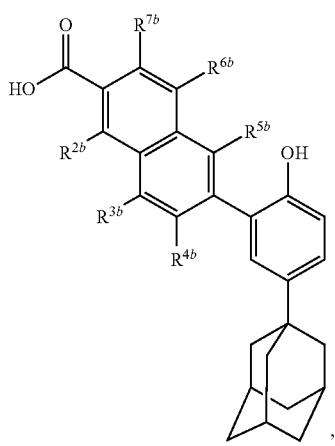

, or a pharmaceutically acceptable salt thereof.

In some embodiments, $R^{2b}$, $R^{3b}$, $R^{4b}$, $R^{5b}$, $R^{6b}$, and $R^{7b}$ are each independently selected from H, HO, and —C(=O)OH.

In some embodiments, $R^{2b}$, $R^{3b}$, $R^{4b}$, $R^{5b}$, $R^{6b}$, and $R^{7b}$ are each independently selected from H and HO.

In some embodiments, the compound of Formula (III) is selected from:

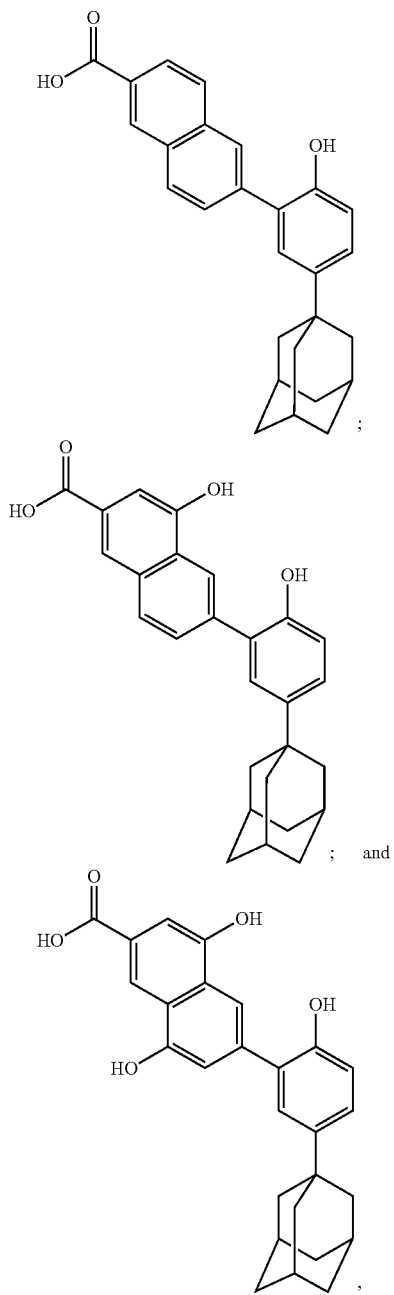

or pharmaceutically acceptable salt thereof.

In a fourth general aspect, the present disclosure provides a pharmaceutical composition comprising a compound selected from: a compound of Formula (I), a compound of Formula (II), and a compound of Formula (III), or a pharmaceutically acceptable salt thereof, and a pharmaceutically acceptable carrier.

Certain implementation of the fourth general aspect are described below:

In some embodiments, the pharmaceutical composition further comprises at least one additional therapeutic agent, or a pharmaceutically acceptable salt thereof.

In some embodiments, the additional therapeutic agent is an antibiotic.

In some embodiments, the antibiotic is selected from: a quinolone, a β-lactam, a cephalosporin, a penicillin, a carbapenem, a lipopetide, an aminoglycoside, a glycopeptide, a macrolide, an ansamycin, a sulfonamide, a monobactam, oxazolidinone, lipopeptide, macrolide, and a cationic antimicrobial peptide (CAMP).

In some embodiments, the antibiotic is selected from: an aminoglycoside and a cationic antimicrobial peptide (CAMP).

In some embodiments, the antibiotic is selected from: gentamicin and defensin 1, or a pharmaceutically acceptable salt thereof.

In some embodiments, the pharmaceutical composition is a topical composition.

In some embodiments, the topical composition is selected from: an aerosol spray, a cream, an emulsion, a foam, an oil, a gel, a lotion, a mousse, an ointment, and a patch.

In some embodiments, the pharmaceutical composition is suitable for administration by a parenteral injection.

In some embodiments, the pharmaceutical composition comprises:

(i) a compound of formula:

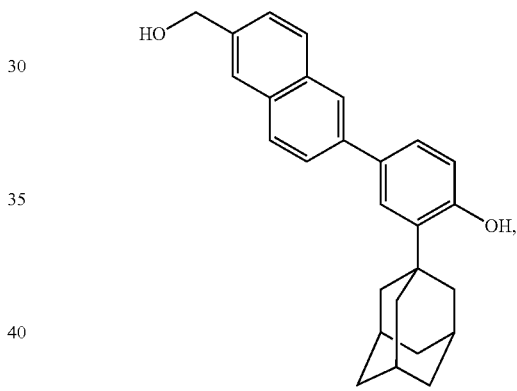

or a pharmaceutically acceptable salt thereof;

(ii) gentamicin, or a pharmaceutically acceptable salt thereof; and (iii) a pharmaceutically acceptable carrier.

In a fifth general aspect, the present disclosure provides a method of killing or inhibiting growth of bacteria, the method comprising contacting the bacteria with an effective amount of a compound selected from: a compound of Formula (I), a compound of Formula (II), and a compound of Formula (III), or a pharmaceutically acceptable salt thereof.

Certain implementations of the fifth general aspect are described below: In some embodiments, the contacting disrupts the bacterial membrane.

In some embodiments, the bacteria is Gram-negative.

In some embodiments, the bacteria is a member of a genus selected from: *Acinetobacter, Burkholderia, Acinetobacter, Burkholderia, Klebsiella, Pseudomonas,* and *Escherichia.*

In some embodiments, the bacteria is a member of a species selected from: *K. pneumoniae, P. aeruginosa,* Enterobacteriaceae, and *E. coli.*

In some embodiments, the bacteria is Gram-positive.

In some embodiments, the bacteria is a member of a genus selected from: *Staphylococcus* (including coagulase negative and coagulase positive), *Streptococcus, Propionibacterium, Peptococcus, Enterococcus*, and *Bacillus*.

In some embodiments, the bacteria is a member of a species selected from: *S. aureus, S. pyogenes, S. pneumoniae, S. salivarius, S. milleri, S. mutans, P. acnes, E. faecalis, E. faecium, B. subtilis*, and *B. anthracis*.

In some embodiments, the bacteria is resistant to one or more antibiotic agents selected from methicillin, vancomycin, rifampicin, gentamicin and ciprofloxacin.

In some embodiments, the bacteria is selected from: methicillin-susceptible *S. aureus* (MSSA), methicillin-resistant *S. aureus* (MRSA), vancomycin-resistant *S. aureus* (VRSA), and coagulase negative staphylococci.

In a sixth general aspect, the present disclosure provides a method of treating a bacterial infection, the method comprising administering to a subject in need thereof a therapeutically effective amount of a compound selected from: a compound of Formula (I), a compound of Formula (II), and a compound of Formula (II), or a pharmaceutically acceptable salt thereof, or a pharmaceutical composition of the fourth general aspect.

Certain implementations of the sixth general aspect are described below:

In some embodiments, the bacterial infection is caused by a Gram-negative bacteria.

In some embodiments, the Gram-negative bacteria is a member of a genus selected from: *Acinetobacter, Burkholderia, Acinetobacter, Burkholderia, Klebsiella, Pseudomonas*, and *Escherichia*.

In some embodiments, the Gram-negative bacteria is a member of a species selected from: *K. pneumoniae, P. aeruginosa*, a Enterobacteriaceae and *E. coli*.

In some embodiments, the bacterial infection is caused by a Gram-positive bacteria.

In some embodiments, the Gram-positive bacteria is a member of a genus selected from: *Staphylococcus* (including coagulase negative and coagulase positive), *Streptococcus, Propionibacterium, Peptococcus, Enterococcus*, and *Bacillus*.

In some embodiments, the Gram-positive bacteria is a member of a species selected from: *S. aureus, S. pyogenes, S. pneumoniae, S. salivarius, S. milleri, S. mutans, P. acnes, E. faecalis, E. faecium, B. subtilis*, and *B. anthracis*.

In some embodiments, the bacterial infection is resistant to treatment with one or more antibiotic agents selected from methicillin, vancomycin, rifampicin, gentamicin and ciprofloxacin.

In some embodiments, the bacterial infection is caused by methicillin-susceptible *S. aureus* (MSSA), methicillin-resistant *S. aureus* (MRSA), vancomycin-resistant *S. aureus* (VRSA), and coagulase negative staphylococci.

In some embodiments, the bacterial infection is selected from: skin and soft tissue infection (including acne), connective tissue infection, bone infection, bacteremia, abscess, joint or muscle infection, wound infection, endovascular infection, CNS infection, abdominal infection, blood stream infection, urinary tract infection, pelvic infection, invasive systemic infection, gastrointestinal infection, and dental infection.

In some embodiments, the bacterial infection is selected from: skin and soft tissue infection (including acne), septic arthritis, atopic dermatitis, sinusitis, food poisoning, abscess, pneumonia, meningitis, osteomyelitis, endocarditis, bacteremia, sepsis, and urinary tract infection.

In some embodiments, the therapeutically effective amount of the compound as described herein, or a pharmaceutically acceptable salt thereof, or a pharmaceutical composition as described herein, is administered to the subject by a route selected from: topical, enteral, and parenteral.

In some embodiments, the method further comprises administering to the subject a therapeutically effective amount of at least one additional therapeutic agent, or a pharmaceutically acceptable salt thereof.

In some embodiments, the additional therapeutic agent is an antibiotic is selected from: a quinolone, a β-lactam, a cephalosporin, a penicillin, a carbapenem, a lipopetide, an aminoglycoside, a glycopeptide, a macrolide, an ansamycin, a sulfonamide, a monobactam, oxazolidinone, lipopeptide, macrolide, and a cationic antimicrobial peptide (CAMP).

In some embodiments, the antibiotic is selected from: an aminoglycoside and cationic antimicrobial peptide (CAMP).

In some embodiments, the antibiotic is selected from: gentamicin and defensin 1, or a pharmaceutically acceptable salt thereof.

In some embodiments:

(i) the compound has formula:

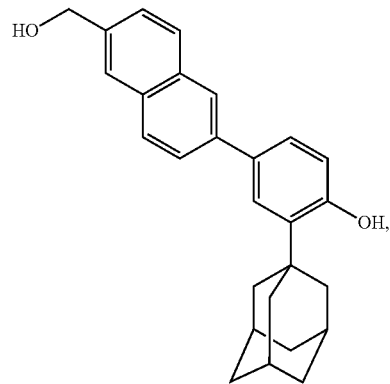 [SMILES: OCc1ccc2cc(-c3ccc(O)c(C45CC6CC(CC(C6)C4)C5)c3)ccc2c1]

or a pharmaceutically acceptable salt thereof; and (ii) the additional therapeutic agent is gentamicin, or a pharmaceutically acceptable salt thereof.

In some embodiments, the compound, or a pharmaceutically acceptable salt thereof, or a pharmaceutical composition of the fourth general aspect, and the at least one additional therapeutic agent, or a pharmaceutically acceptable salt thereof, and administered to the subject consecutively.

In some embodiments, the compound, or a pharmaceutically acceptable salt thereof, or a pharmaceutical composition of the fourth general aspect, and the at least one additional therapeutic agent, or a pharmaceutically acceptable salt thereof, and administered to the subject simultaneously.

In a seventh general aspect, the present disclosure provides a method of killing or inhibiting growth of a bacteria which is *P. acnes*, comprising contacting the bacteria with an effective amount of a compound of Formula (IV):

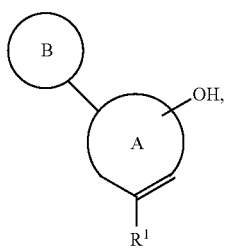

(IV)

or a pharmaceutically acceptable salt thereof, wherein:
R¹ is selected from any one of the following moieties:

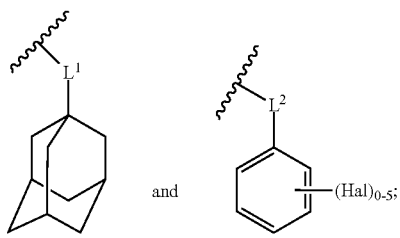

L¹ is $C_{1-3}$ alkylene, or L¹ is absent;
L² is $C_{1-3}$ alkylene;
each Hal is independently a halogen;
ring A is selected from the group consisting of phenyl and naphthyl, each of which is optionally substituted by 1, 2, or 3 OH groups; and
ring B is selected from the group consisting of phenyl and naphthyl, each of which is optionally substituted by 1, 2, 3, 4, 5, or 6 groups independently selected from OH, HO—$C_{1-3}$ alkylene, —C(=O)N(di-$C_{1-4}$ alkyl), —C(=O)NH($C_{1-4}$ alkyl), —C(=O)NH$_2$, —C(=O)—$C_{1-4}$ alkoxy, —C(=O)OH, and —(CH=CH)—C(=O)OH.

Certain implementations of the seventh general aspect are described below:

In some embodiments, the compound of Formula (IV) has any one of the following formulae:

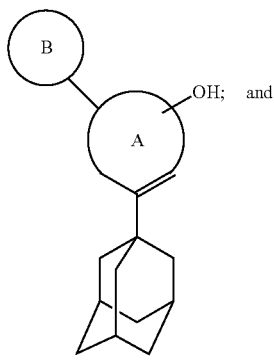 and

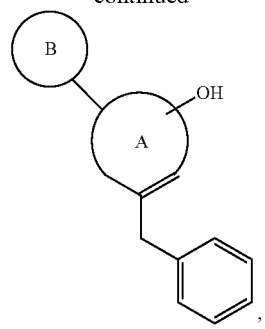

or a pharmaceutically acceptable salt thereof.

In some embodiments, ring A is phenyl and ring B is phenyl.

In some embodiments, ring A is phenyl and ring B is naphthyl.

In some embodiments, ring A is naphthyl and ring B is phenyl.

In some embodiments, the compound of Formula (IV) has any one of the following formulae:

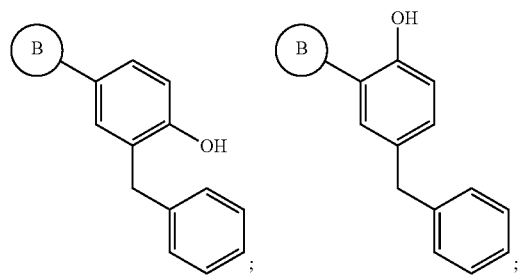

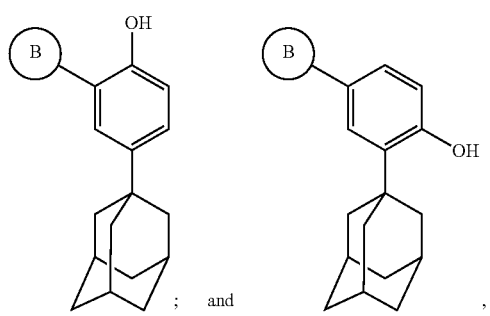

or a pharmaceutically acceptable salt thereof.

In some embodiments, ring B is phenyl.

In some embodiments, ring B is naphthyl.

In some embodiments, ring B is substituted with at least one group —C(=O)OH.

In some embodiments, ring B is substituted with at least one group HO—$C_{1-3}$ alkylene.

In some embodiments, ring B is optionally substituted with 1, 2, or 3 groups independently selected from OH, HO—$C_{1-3}$ alkylene, C(=O)NH($C_{1-4}$ alkyl), —C(=O)NH$_2$, —C(=O)—$C_{1-4}$ alkoxy, and —C(=O)OH.

In some embodiments, the compound of Formula (IV) is selected from any one of the following compounds:
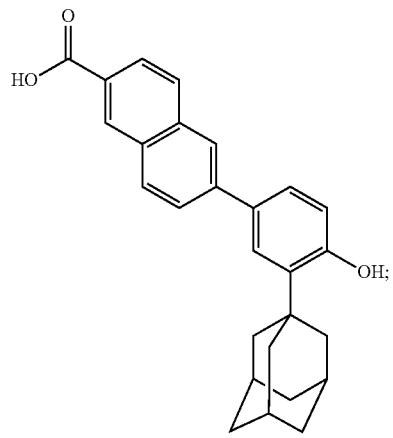
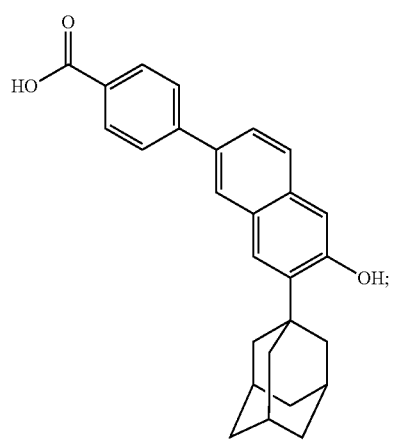
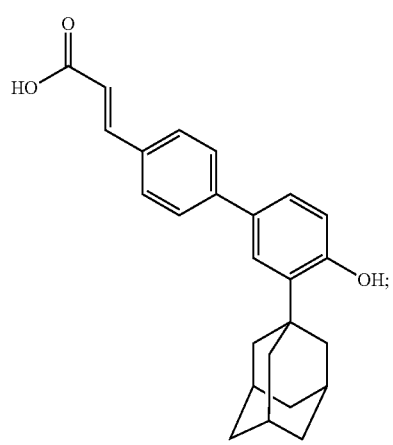
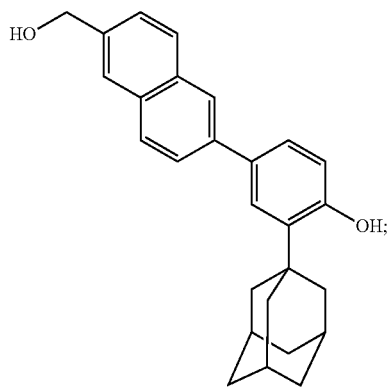 [SMILES: OCc1ccc2cc(-c3ccc(O)c(C45CC6CC(CC(C6)C4)C5)c3)ccc2c1]
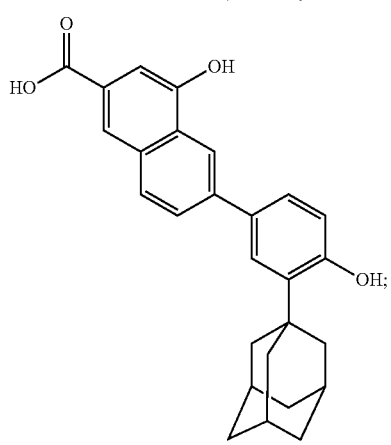
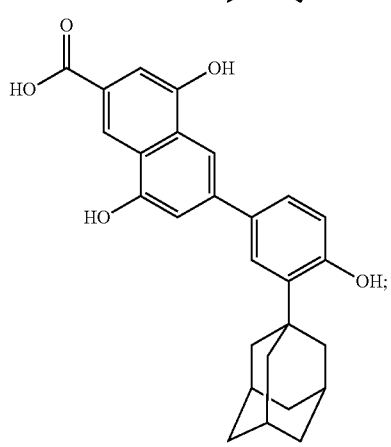
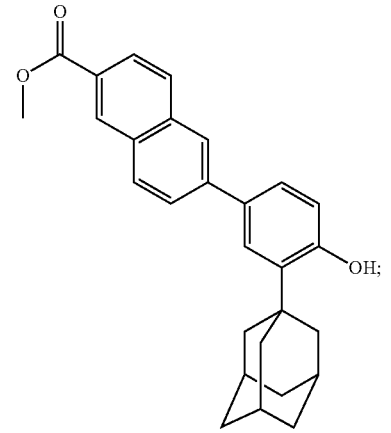

-continued
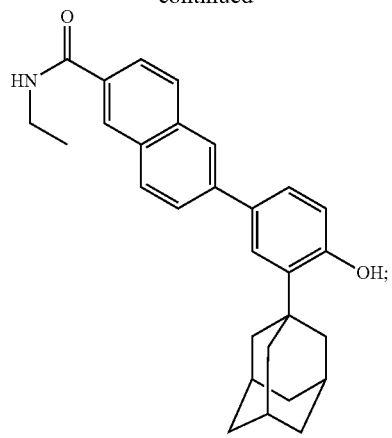
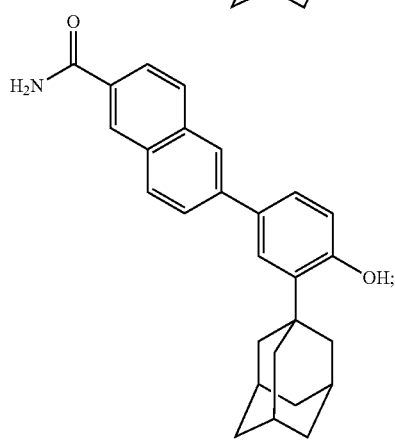
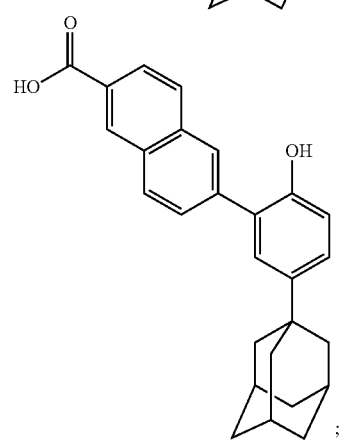
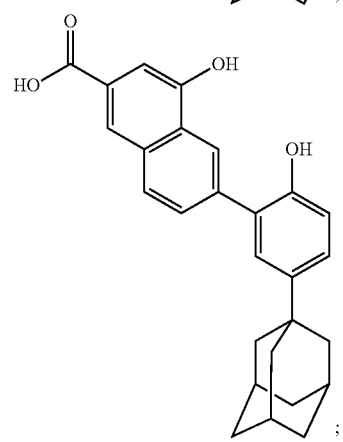
-continued
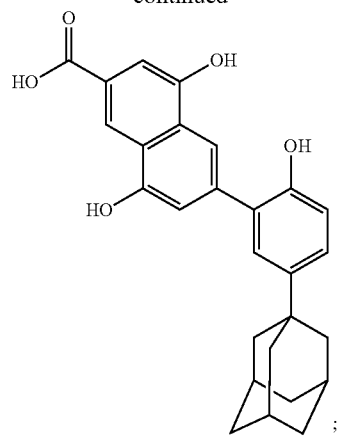
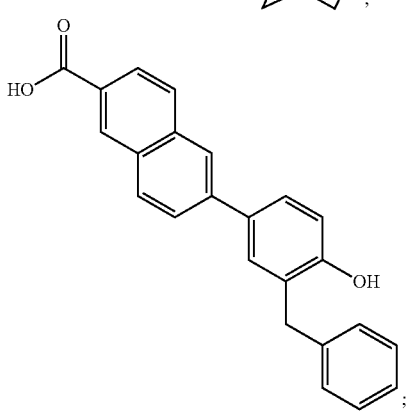
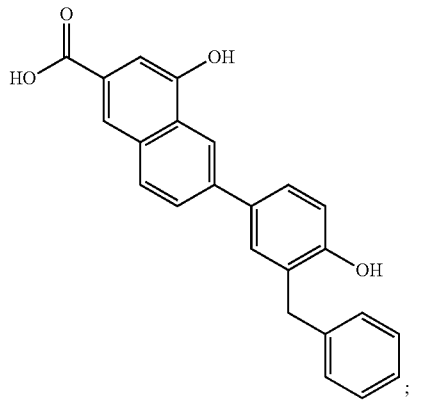
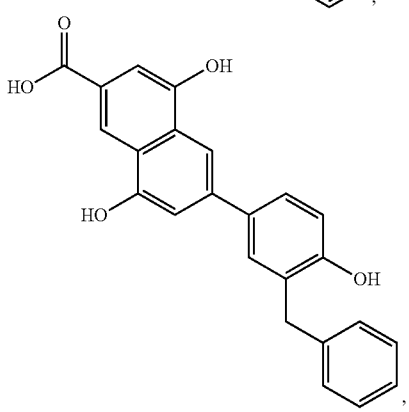
or a pharmaceutically acceptable salt thereof.
In some embodiments, the contacting disrupts the bacterial membrane of *P. acnes* bacteria.

In some embodiments, the bacteria is resistant to one or more antibiotic agents selected from methicillin, vancomycin, rifampicin, gentamicin and ciprofloxacin.

In an eighth general aspect, the present disclosure provides a method of treating a bacterial infection caused by bacteria which is *P. acnes*, comprising administering to a subject in need thereof a therapeutically effective amount of a compound of Formula (IV) as described herein for the seventh general aspect, of a pharmaceutically acceptable salt thereof.

Certain implementations of the eighth general aspect are described below:

In some embodiments, the bacterial infection is resistant to treatment with one or more antibiotic agents selected from methicillin, vancomycin, rifampicin, gentamicin and ciprofloxacin.

In some embodiments, the bacterial infection is selected from: skin and soft tissue infection (including acne), connective tissue infection, bone infection, and joint or muscle infection.

In some embodiments, the bacterial infection is selected from: skin acne and septic arthritis.

In some embodiments, the therapeutically effective amount of the compound of Formula (IV), or a pharmaceutically acceptable salt thereof, is administered to the subject by a route selected from: topical, enteral, and parenteral.

In some embodiments, administering the compound of Formula (IV), or a pharmaceutically acceptable salt thereof, by topical route includes administering the compound in a form of an aerosol spray, a cream, an emulsion, a foam, an oil, a gel, a lotion, a mousse, an ointment, or a patch.

In some embodiments, the method further comprises administering to the subject a therapeutically effective amount of at least one additional therapeutic agent, or a pharmaceutically acceptable salt thereof.

In some embodiments, the additional therapeutic agent is an antibiotic.

In some embodiments, the antibiotic is selected from: a quinolone, a β-lactam, a cephalosporin, a penicillin, a carbapenem, a lipopetide, an aminoglycoside, a glycopeptide, a macrolide, an ansamycin, a sulfonamide, a monobactam, oxazolidinone, lipopetide, macrolide, and a cationic antimicrobial peptide (CAMP).

In some embodiments, the antibiotic is selected from: an aminoglycoside and cationic antimicrobial peptide (CAMP).

In some embodiments, the antibiotic is selected from: gentamicin and defensin 1, or a pharmaceutically acceptable salt thereof.

In some embodiments:
(i) the compound of Formula (IV) is:

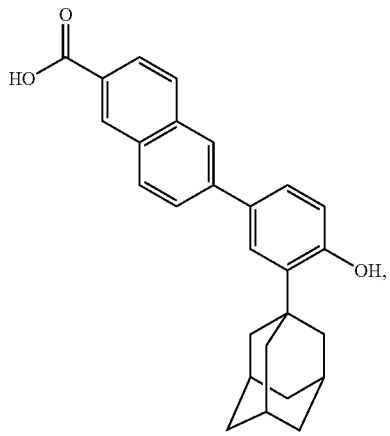 [SMILES: O=C(O)c1ccc2cc(-c3ccc(O)c(C45CC6CC(CC(C6)C4)C5)c3)ccc2c1]

or a pharmaceutically acceptable salt thereof; and (ii) the additional therapeutic agent is gentamicin, or a pharmaceutically acceptable salt thereof.

In some embodiments:
(i) the compound of Formula (IV) is:

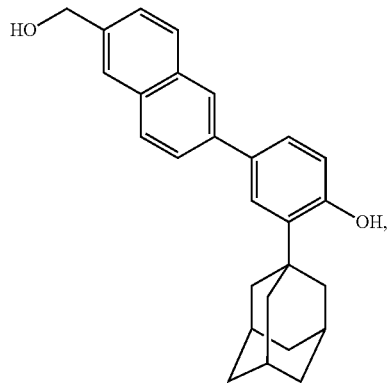 [SMILES: OCc1ccc2cc(-c3ccc(O)c(C45CC6CC(CC(C6)C4)C5)c3)ccc2c1]

or a pharmaceutically acceptable salt thereof; and
(ii) the additional therapeutic agent is gentamicin, or a pharmaceutically acceptable salt thereof.

In some embodiments, the compound of Formula (IV), or a pharmaceutically acceptable salt thereof, and the at least one additional therapeutic agent, or a pharmaceutically acceptable salt thereof, and administered to the subject consecutively.

In some embodiments, the compound of Formula (IV), or a pharmaceutically acceptable salt thereof, and the at least one additional therapeutic agent, or a pharmaceutically acceptable salt thereof, and administered to the subject simultaneously.

Unless otherwise defined, all technical and scientific terms used herein have the same meaning as commonly understood by one of ordinary skill in the art to which the present application belongs. Methods and materials are described herein for use in the present application; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the present application will be apparent from the following detailed description and figures, and from the claims.

DESCRIPTION OF DRAWINGS

FIG. 2. Compound 2 retains antimicrobial activity against MRSA persisters and has improved cytotoxicity. a, Chemical structure of Analog 2. b, Viability of *S. aureus* MW2 persisters treated with Analog 2 alone or in combination with gentamicin (Gm). Data points on the x-axis were below the level of detection (2×102 CFU/ml). c, Viability of normal human primary hepatocytes and human hepatoma (HepG2) cells treated with retinoids in serum-free media for 24 h based on the absorbance readings at 450 nm at 4 h after adding WST-1. The FDA-approved antineoplastic retinoid bexarotene was used as a control. b and c, Individual data points (n=3 biologically independent samples) are shown;

Figure 1:
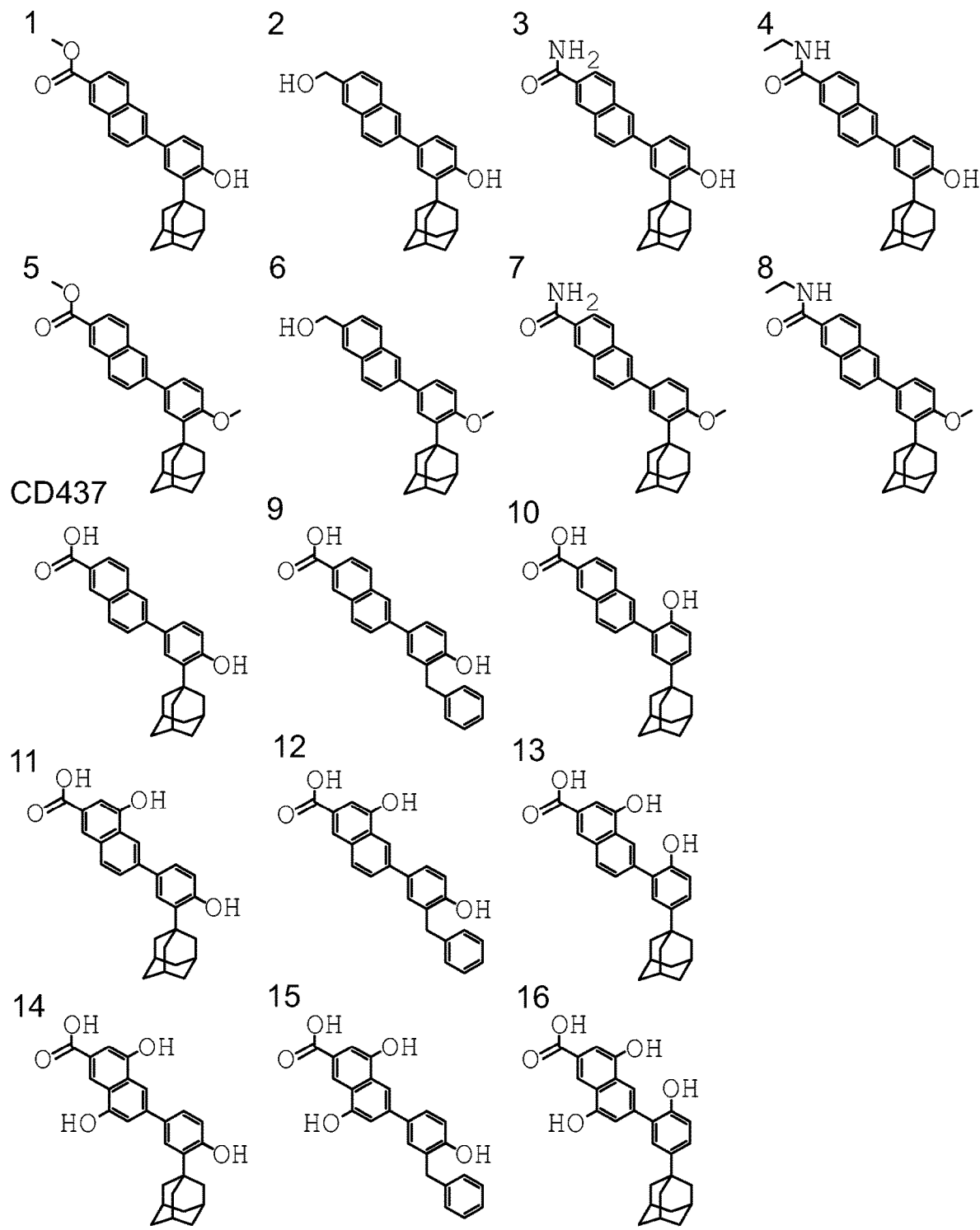
FIG. 1 depicts chemical structures of the exemplified compounds.

error bars represent means±s.d. d, Efficacy of Analog 2 alone or in combination with gentamicin in a deep-seated mouse thigh infection model. Each group of MW2-infected neutropenic mice (n=10 biologically independent animals) was treated with the indicated doses of Analog 2 (i.p.) alone or in combination with 30 mg/kg gentamicin (Gm, s.c.), a combination of 25 mg/kg vancomycin (Van, i.p.) and 30 mg/kg gentamicin (s.c.), or control (5% Kolliphor+5% ethanol, i.p.) every 12 h for 3 days beginning 24 h post-infection. At 12 h after the last treatment, mice were euthanized and their thighs were excised and homogenized. CFUs from each mouse thigh are plotted as individual points. Error bars represent means±s.d. Statistical differences between control and antibiotic treatment groups were analyzed by one-way ANOVA and post-hoc Tukey test (P=0.0002, *P<0.0001).

FIG. 3. Evaluation of cytotoxic potentials of retinoids in various cell lines. a, 2% human erythrocytes were treated with two-fold serially diluted concentrations of the retinoids for 1 h at 37° C. A sample treated with 1% Triton-X 100 was used as the control for 100% hemolysis. b, Normal rat, human primary hepatocytes, human hepatoma (HepG2) cells, normal human primary renal proximal tubule epithelial cells (RPTEC), or adult normal human epidermal keratinocytes (NHEK) were treated with a range of concentrations of the synthetic retinoids in chemically defined, serum-free media for 24 h. The FDA-approved antineoplastic retinoid bexarotene was used as a control. Cell viability was calculated based on absorbance readings at 450 nm at 4 h after adding WST-1. a and b, Individual data points (n=3 biologically independent samples) are shown; error bars represent means±s.d. c, Three synthetic retinoids and the positive control quinidine were tested for inhibition of the hERG potassium channel. Individual data points (n=4 biologically independent samples) are shown; error bars represent means±s.d. Data are fitted to a standard inhibition curve.

FIG. 4 Activity of exemplified compounds. a, The chemical structures of newly synthesized retinoid compounds. b, MICs and membrane permeability were measured with *S. aureus* strain MW2. Membrane permeability was evaluated spectrophotometrically by monitoring the uptake of SYTOX Green (Ex=485 nm, Em=525 nm) over time. Individual data points (n=2 biologically independent samples) and means are shown; error bars are not shown for clarity.

FIG. 5 Determination of Analogs 2 and 9's biological properties. a, Human erythrocytes and b, rat primary hepatocytes were treated with the Analogs 2 or 9 for 1 h and 24 h, respectively. c, MRSA MW2 persisters were treated with Analog 9. The data points on the x-axis are below the level of detection ($2 \times 10^2$ CFU/ml). a-c, Individual data points (n=3 biologically independent samples) are shown; error bars represent means±s.d. d, Representative configurations of MD simulations of Analog 2 interacting with lipid bilayers (108 PG lipids, 72 Lys-PG lipids, and 10 DPG lipids). Simulations were repeated 5 times with similar results. e, Free energy profiles of Analog 2, CD437, and Adarotene penetrating the membrane as a function of the distance between the center-of-mass (COM) distance to the lipid bilayer. The dot-dashed line marks the membrane surface, averaged from the COM location of phosphate groups in outer leaflet. Individual data points (n=3 independent simulations) are shown; error bars represent means±s.d. f, The plasma concentrations of Analog 2 after a single injection of Analog 2 (20 mg/kg, i.p., 3 mice per time point) were measured using LC-MS/MS. PK analysis was conducted using Phoenix WinNonlin software version 6.3. Individual data points (n=3 biologically independent animals) are shown; error bars represent means±s.d. The determined PK parameters are $T_{max}$ (the time taken to reach the maximum concentration) of 0.5 hr, $C_{max}$ (maximum concentration observed) of 16.14 µg/ml, $AUC_{last}$ (area under the curve to last time point) of 16.38 hr*µg/ml, $AUC_{inf}$ (area under the curve to infinite) of 16.54 hr*µg/ml, $T_{1/2}$ (Half-life) of 4.49 hr, CL (clearance) of 20.16 ml/min/kg. g, Six mice per group (n=6 biologically independent animals) were treated with control (5% Kolliphor+5% ethanol, i.p.), vancomycin (25 mg/kg, i.p.), or Analog 2 (10-80 mg/kg, i.p.) every 12 h for 3 days. At 12 h after the last treatment, alanine aminotransferase (ALT) and blood urea nitrogen (BUN) were analyzed. International Units per Liter (IU/L) of ALT and mg/dL of BUN for each mouse serum are plotted as individual points and error bars represent means±s.d. Control and antibiotic treatments were analyzed by one-way ANOVA and post-hoc Tukey test, which demonstrated a lack of significant differences (P>0.7 for all ALT and BUN samples).

Figure 6A:
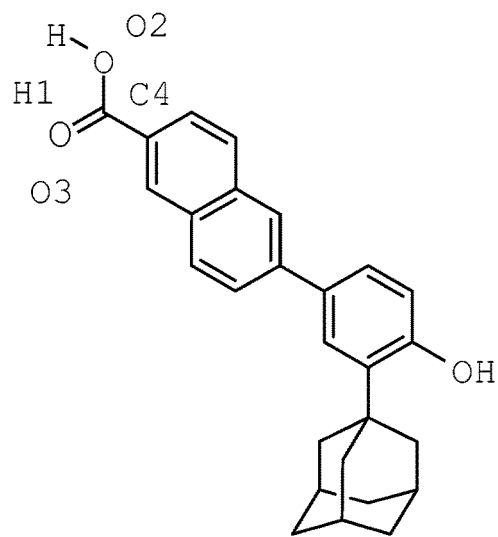
Figure 6A:
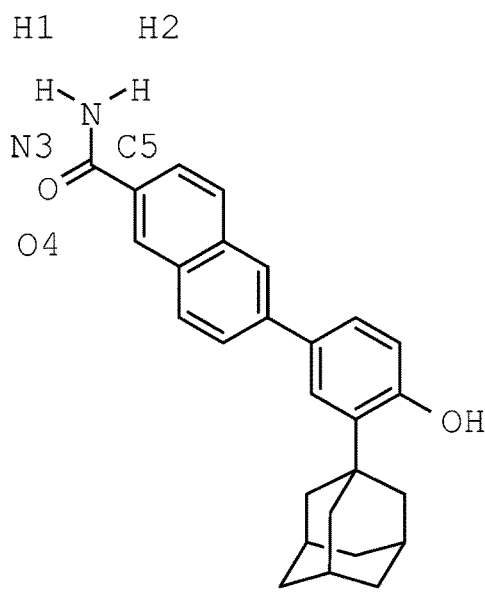

FIG. 6 The charges and the numbers of branch groups affects membrane activity of CD437-like retinoids. a, Comparison of partial atomic charges between CD437 and Analog 3. b, Representative configurations of MD simulations of Analogs 3, 11, and 14 interacting with lipid bilayers (7DOPC/3DOPG). The amide group in Analog 3 is repelled away from the membrane despite the attachment of the hydroxyl group. Simulations were repeated 5 times with similar results. Free energy profiles of c, Analog 3 penetrating 7DOPC/3DOPG lipid bilayers, d, CD437 penetrating differently charged lipid bilayers, e, Analogs 11 and 14 penetrating 7DOPC/3DOPG lipid bilayers as a function of the distance between the center-of-mass (COM) distance to the lipid bilayer. The dot-dashed line marks the membrane surface, averaged from the COM location of phosphate groups in outer leaflet. c-e, Individual data points (n=3 independent simulations) are shown; error bars represent means±s.d.

Figure 7:
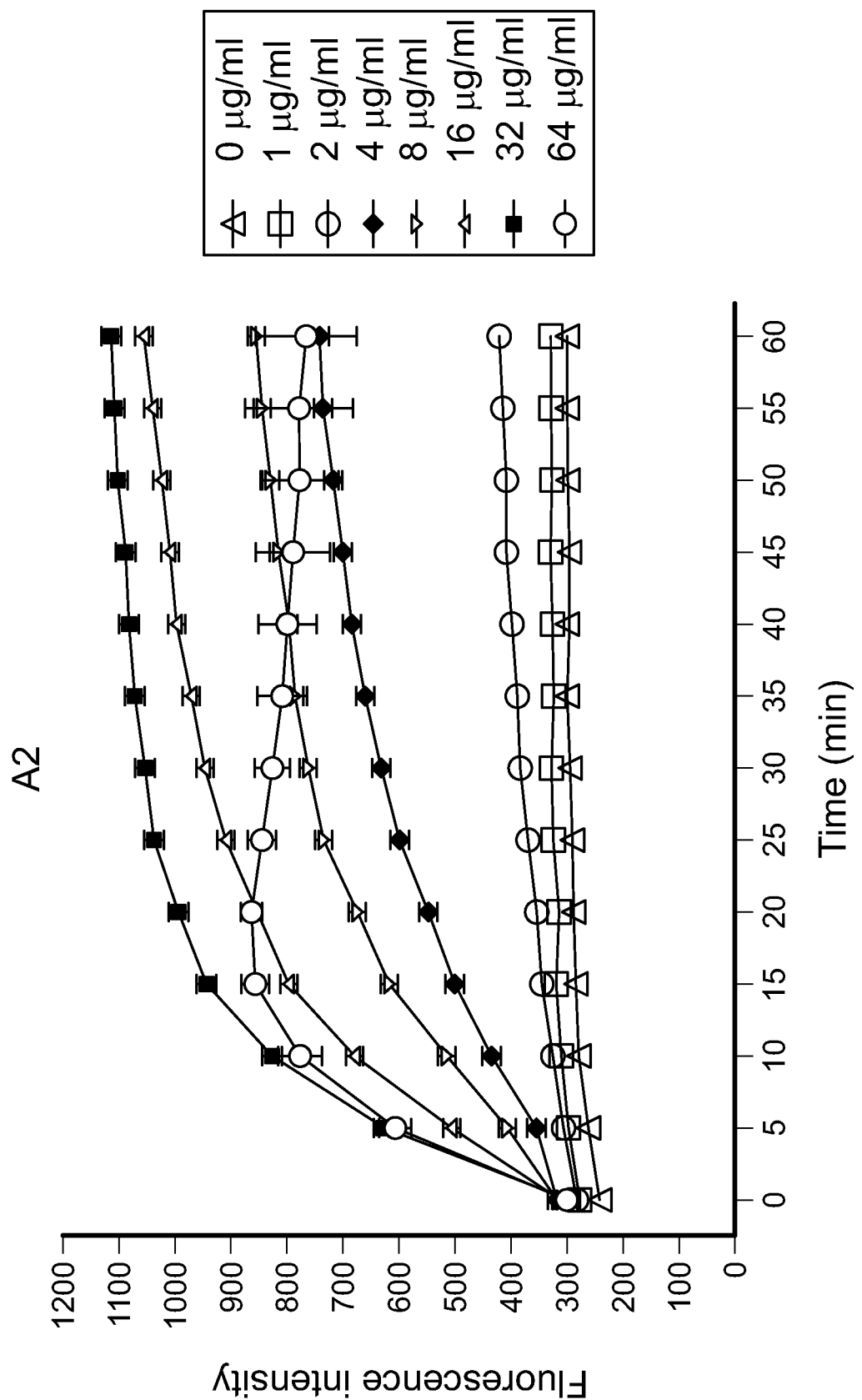

FIG. 7 is a line plot showing membrane permeability by compound 2 at various concentrations.

FIG. 8 is a table showing MIC of synthetic retinoids CD437, CD1530, adarotene, and compound 2 against *P. acnes* isolate ATCC6919.

FIG. 9 Anti-persister activity and toxicity of Analog 2 and 9. (a) MRSA persisters were treated with the indicated concentrations of Analog 2 or 9. Viability was measured by serial dilution and plating on TSA plates. The data points on the x-axis are below the level of detection ($2 \times 10^2$ CFU/ml). (b) 2% human erythrocytes were treated with two-fold serially diluted concentration of CD437, Analog 2 or 9 for 1 h at 37° C. A sample treated with 1% Triton-X 100 was used as the control for 100% hemolysis. (c) Rat or (d) human primary hepatocytes cultured in a collagen gel sandwich system were treated with a range of concentration of CD437, Analog 2, or 9 in chemically defined, serum-free media for 24 h. Cell viability was calculated based on the absorbance readings at 450 nm at 4 h after adding WST-1 using the following equation: % viability=$(Abs_{sample}-Abs_{blank})/(Abs_{non-treated}-Abs_{blank}) \times 100$. (a, b, c, d) Results are shown as means±s.d.; n=3.

Figure 10:
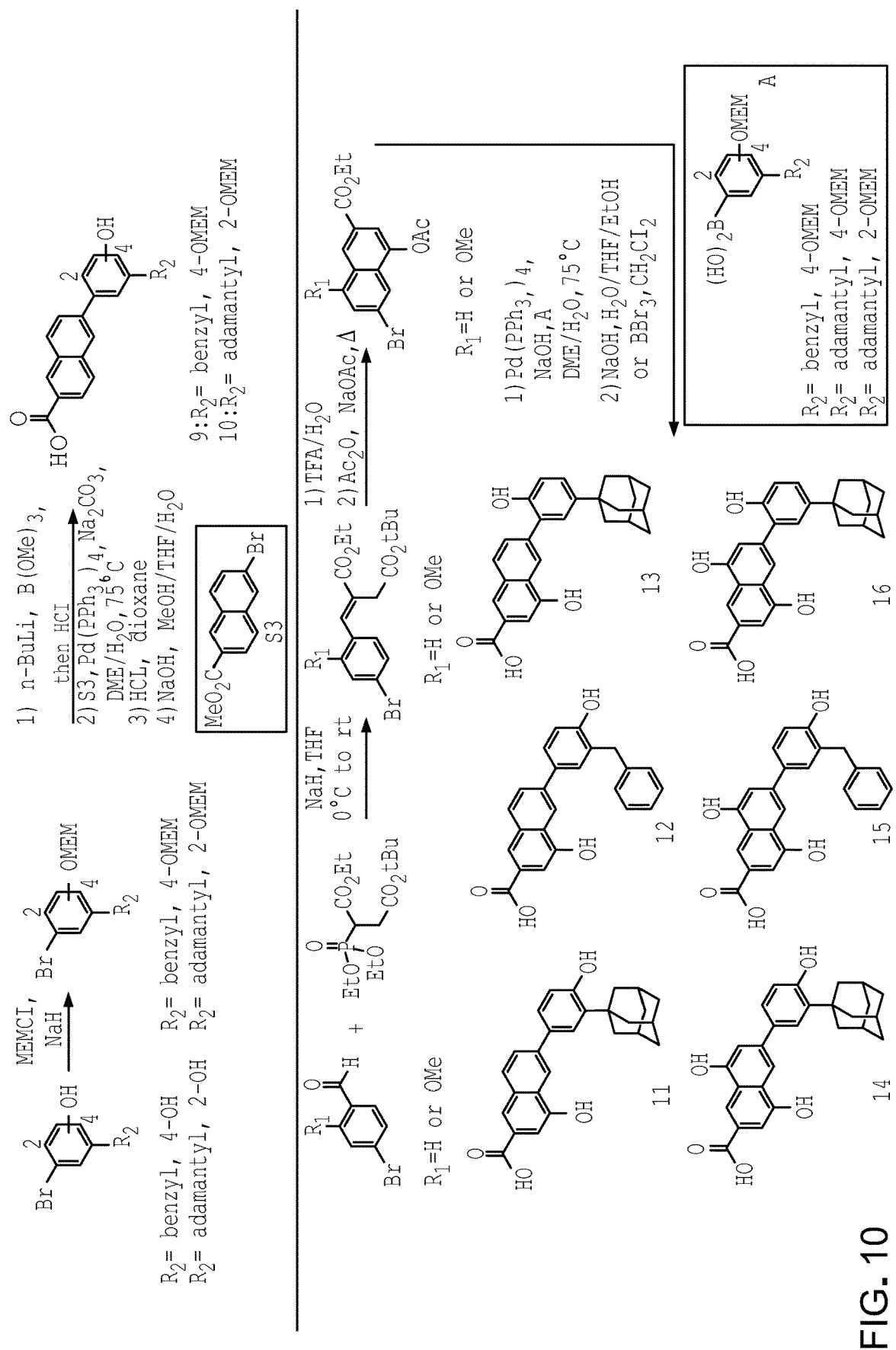

FIG. 10 is a synthetic scheme showing synthesis of compounds 9-16.

Figure 11:
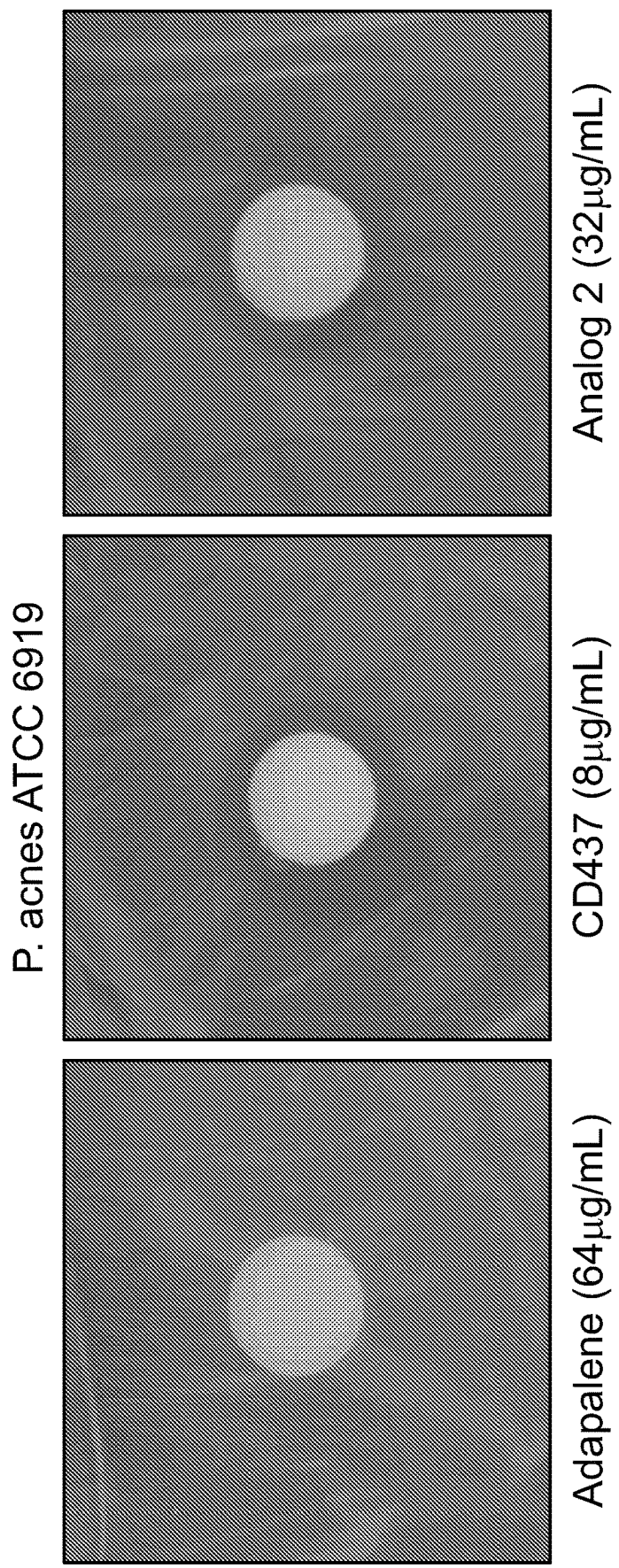

FIG. 11 is an image showing that retinoids CD437 and compound 2 (but not adapalene) inhibit the growth of *Cutibacterium (Propionibacterium) acnes*.

Figure 12:
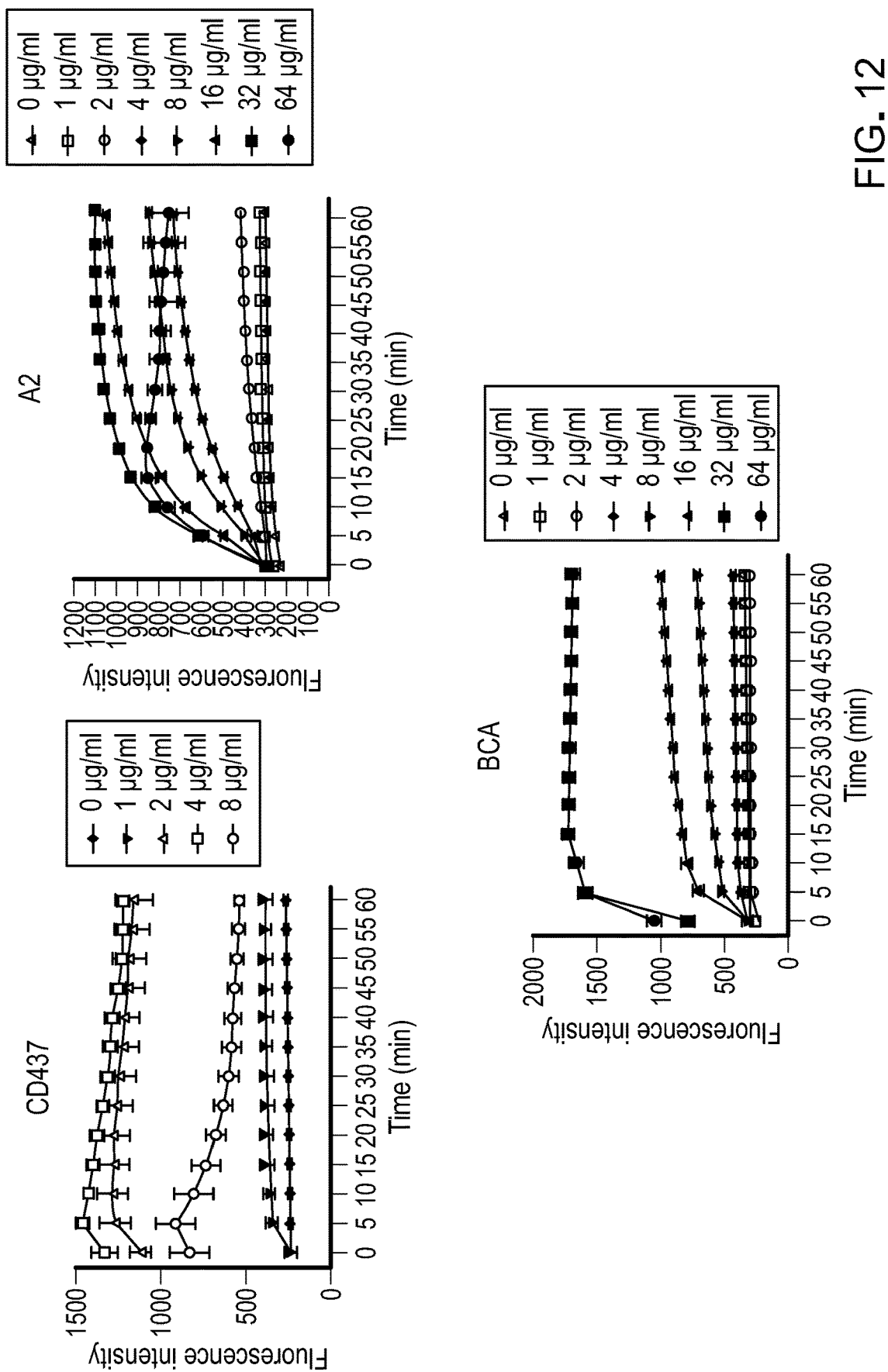

FIG. 12 contains line plots showing that the mode of action of CD437 and compound 2 is by increasing permeability of the bacterial membrane.

Figure 13:
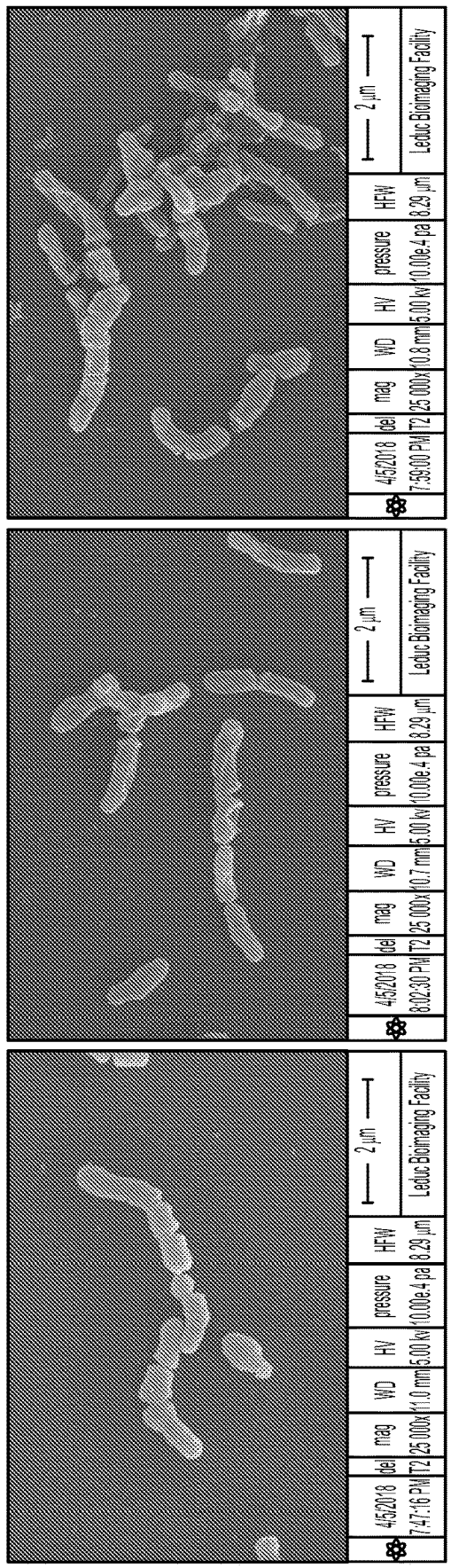

FIG. 13 is an image showing that the morphology of Cutibacterium (*Propionibacterium*) *acnes* bacteria treated with CD437 or compound 2 was altered and elongated, further confirming that the retinoids CD437 and compound 2 affect the membrane of the bacteria.

DETAILED DESCRIPTION

Introduction

The present application provides bacterial membrane-selective synthetic retinoid analogs that—when compared to the conventional antibiotics agents—advantageously retain potent antimicrobial activity (including activity against persisters) but show reduced cytotoxicity, improved pharmacokinetic profile, and low probability for developing resistance. Such exemplary antibacterial compounds, compositions containing these compounds and methods of making and using these compounds are described herein.

Antibacterial Compounds

In some embodiments, the present application provides a compound of Formula (I):

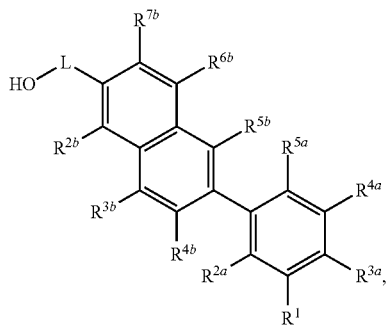

(I)

or a pharmaceutically acceptable salt thereof, wherein:
L is $C_{1-3}$ alkylene;
$R^1$ is selected from any one of the following moieties:

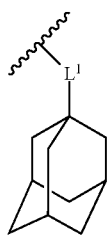 and 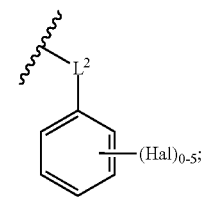

$L^1$ is $C_{1-3}$ alkylene, or $L^1$ is absent;
$L^2$ is $C_{1-3}$ alkylene;
each Hal is independently a halogen;
$R^{2a}$, $R^{3a}$, $R^{4a}$, and $R^{5a}$ are each independently selected from H and OH;
provided that at least one of $R^{2a}$, $R^{3a}$, $R^{4a}$, and $R^{5a}$ is OH; and
$R^{2b}$, $R^{3b}$, $R^{4b}$, $R^{5b}$, $R^{6b}$, and $R^{7b}$ are each independently selected from H, HO—$C_{1-3}$ alkylene, and —C(=O)OH.

In some embodiments, the compound of Formula (I) has formula:

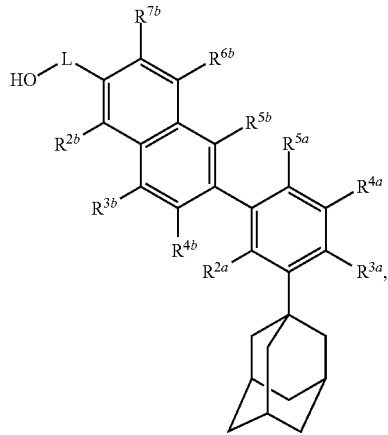

or a pharmaceutically acceptable salt thereof.

In some embodiments, the compound of Formula (I) has formula:

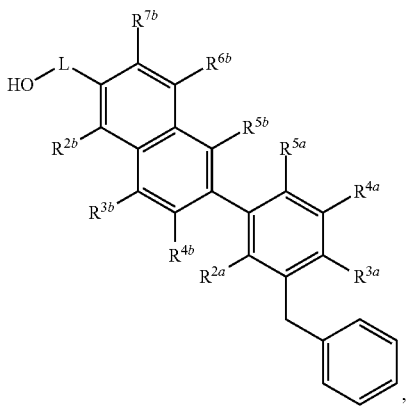

or a pharmaceutically acceptable salt thereof.

In some embodiments, the compound of Formula (I) has formula:

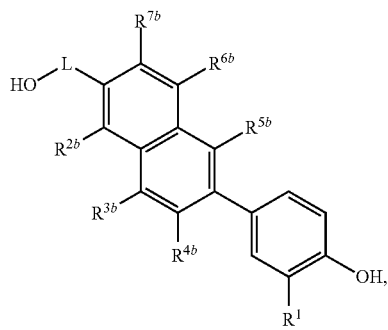

or a pharmaceutically acceptable salt thereof.

In some embodiments, the compound of Formula (I) has formula:

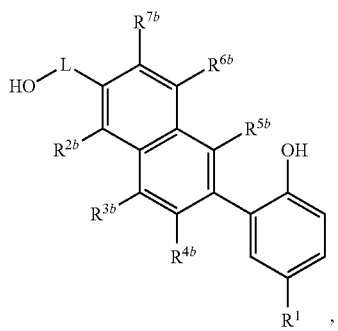

or a pharmaceutically acceptable salt thereof.

In some embodiments, $R^{2b}$, $R^{3b}$, $R^{4b}$, $R^{5b}$, $R^{6b}$, and $R^{7b}$ are each independently selected from H and —C(=O)OH.

In some embodiments, at least one of $R^{2b}$, $R^{3b}$, $R^{4b}$, $R^{5b}$, $R^{6b}$, and $R^{7b}$ is —C(=O)OH. In some embodiments, at least two of $R^{2b}$, $R^{3b}$, $R^{4b}$, $R^{5b}$, $R^{6b}$, and $R^{7b}$ is —C(=O)OH. In some embodiments, $R^{2b}$ is —C(=O)OH. In some embodiments, $R^{3b}$ is —C(=O)OH. In some embodiments, $R^{4b}$ is —C(=O)OH. In some embodiments, $R^{5b}$ is —C(=O)OH. In some embodiments, $R^{6b}$ is —C(=O)OH. In some embodiments, $R^{7b}$ is —C(=O)OH.

In some embodiments, at least one of $R^{2b}$, $R^{3b}$, $R^{4b}$, $R^{5b}$, $R^{6b}$, and $R^{7b}$ is HO—$C_{1-3}$ alkylene. In some embodiments, at least two of $R^{2b}$, $R^{3b}$, $R^{4b}$, $R^{5b}$, $R^{6b}$, and $R^{7b}$ is HO—$C_{1-3}$ alkylene. In some embodiments, $R^{2b}$ is HO—$C_{1-3}$ alkylene. In some embodiments, $R^{3b}$ is HO—$C_{1-3}$ alkylene. In some embodiments, $R^{4b}$ is HO—$C_{1-3}$ alkylene. In some embodiments, $R^{5b}$ is HO—$C_{1-3}$ alkylene. In some embodiments, $R^{6b}$ is HO—$C_{1-3}$ alkylene. In some embodiments, $R^{77}$ is HO—$C_{1-3}$ alkylene.

In some embodiments, each of $R^{2b}$, $R^{3b}$, $R^{4b}$, $R^{5b}$, $R^{6b}$, and $R^{7b}$ is H.

In some embodiments, L is methylene. In some embodiments, L is ethylene (1,2-ethylene or 1,2-ethylene). In some embodiments, L is propylene (e.g., 1,1-propylene, 1,2-propylene, or 1,3-propylene).

In some embodiments, $R^1$ is:

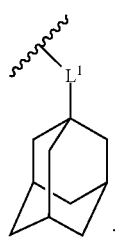

In some embodiments, $L^1$ is methylene. In some embodiments, $L^1$ is ethylene (1,2-ethylene or 1,2-ethylene). In some embodiments, $L^1$ is propylene (e.g., 1,1-propylene, 1,2-propylene, or 1,3-propylene). In some embodiments, $L^1$ is absent and $R^1$ has formula:

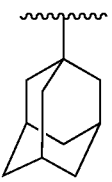

In some embodiments, $R^1$ is:

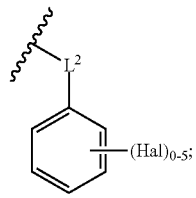

In some embodiments, $L^2$ is ethylene (1,2-ethylene or 1,2-ethylene). In some embodiments, $L^2$ is propylene (e.g., 1,1-propylene, 1,2-propylene, or 1,3-propylene). In some embodiments, $L^2$ is methylene and $R^1$ has formula:

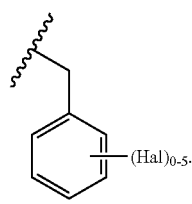

In some embodiments, each Hal is independently selected from: Cl, F, Br, and I. In some embodiments, at least one Hal is F. In some embodiments, at least one Hal is Cl.

In some embodiments, $R^1$ is selected from:

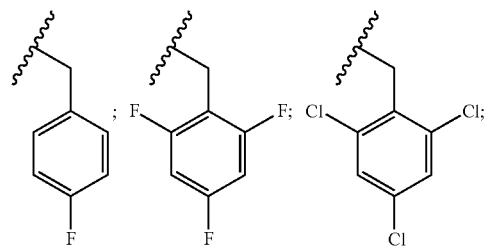

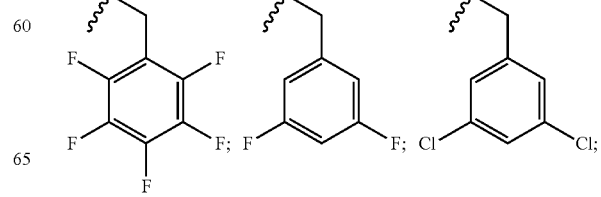

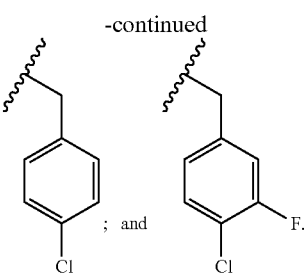

In some embodiments, at least one of $R^{2a}$, $R^{3a}$, $R^{4a}$, and $R^{5a}$ is OH. In some embodiments, $R^{2a}$ is OH. In some embodiments, $R^{3a}$ is OH. In some embodiments, $R^{4a}$ is OH. In some embodiments, $R^{5a}$ is OH.

In some embodiments, the compound of Formula (I) is:

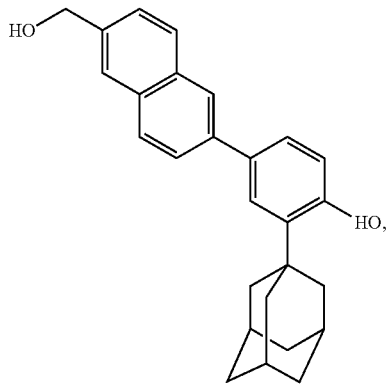 [SMILES: OCc1ccc2cc(-c3ccc(O)c(C45CC6CC(CC(C6)C4)C5)c3)ccc2c1]

or a pharmaceutically acceptable salt thereof.

In some embodiments, the present application provides a compound of Formula (II):

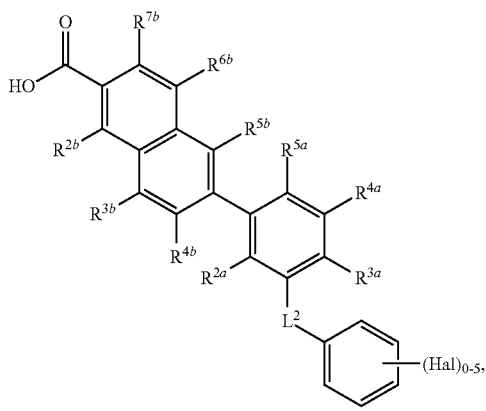

(II)

or a pharmaceutically acceptable salt thereof, wherein:
$L^2$ is $C_{1-3}$ alkylene;
each Hal is independently a halogen;
$R^{2a}$, $R^{3a}$, $R^{4a}$, and $R^{5a}$ are each independently selected from H and OH;
provided that at least one of $R^{2a}$, $R^{3a}$, $R^{4a}$, and $R^{5a}$ is OH; and
$R^{2b}$, $R^{3b}$, $R^{4b}$, $R^{5b}$, $R^{6b}$, and $R^{7b}$ are each independently selected from H, OH, HO—$C_{1-3}$ alkylene, and —C(=O)OH.

In some embodiments, the compound of Formula (II) has formula:

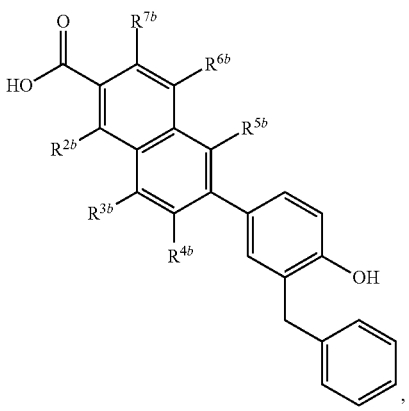

or a pharmaceutically acceptable salt thereof.

In some embodiments, the compound of Formula (II) has formula:

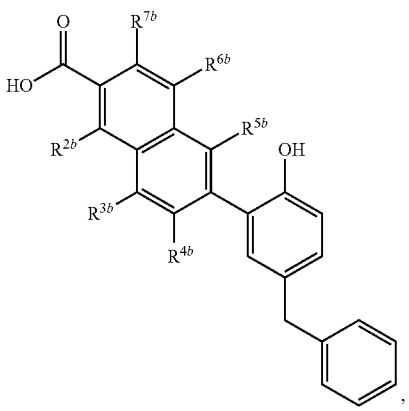

or pharmaceutically acceptable salt thereof.

In some embodiments, $L^2$ is ethylene (1,2-ethylene or 1,2-ethylene). In some embodiments, $L^2$ is propylene (e.g., 1,1-propylene, 1,2-propylene, or 1,3-propylene).

In some embodiments, $L^2$ is methylene and the moiety of formula:

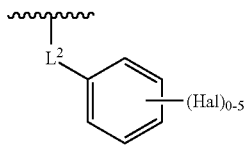

has formula:

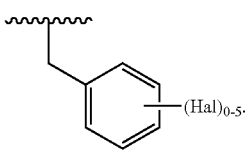

In some embodiments, each Hal is independently selected from: Cl, F, Br, and I. In some embodiments, at least one Hal is F. In some embodiments, at least one Hal is Cl.

In such embodiments, the moiety containing the L² group depicted above has any one of the following formulae:

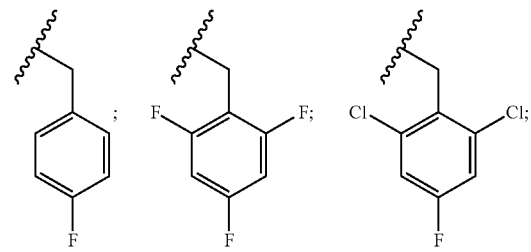

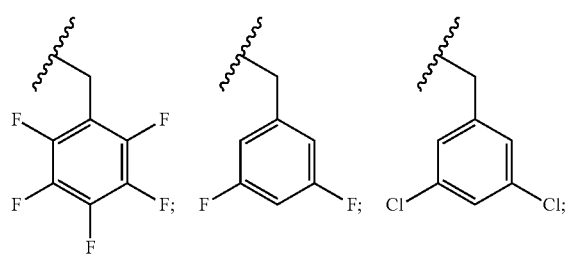

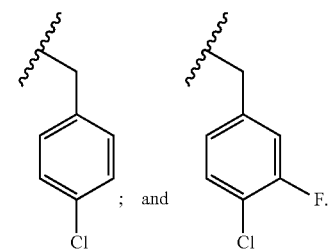

In some embodiments, at least one of $R^{2a}$, $R^{3a}$, $R^{4a}$, and $R^{5a}$ is OH. In some embodiments, $R^{2a}$ is OH. In some embodiments, $R^{3a}$ is OH. In some embodiments, $R^{4a}$ is OH. In some embodiments, $R^{5a}$ is OH.

In some embodiments, $R^{2b}$, $R^{3b}$, $R^{4b}$, $R^{5b}$, $R^{6b}$, and $R^{7b}$ are each H. In some embodiments, $R^{2b}$, $R^{3b}$, $R^{4b}$, $R^{5b}$, $R^{6b}$, and $R^{7b}$ are each independently selected from H, OH, and —C(=O)OH. In some embodiments, $R^{2b}$, $R^{3b}$, $R^{4b}$, $R^{5b}$, $R^{6b}$, and $R^{7b}$ are each independently selected from H and OH. In some embodiments, $R^{2b}$, $R^{3b}$, $R^{4b}$, $R^{5b}$, $R^{6b}$, and $R^{7b}$ are each independently selected from H and —C(=O)OH. In some embodiments, $R^{2b}$, $R^{3b}$, $R^{4b}$, $R^{5b}$, $R^{6b}$, and $R^{7b}$ are each independently selected from H and HO—$C_{1-3}$ alkylene.

In some embodiments, at least one of $R^{2b}$, $R^{3b}$, $R^{4b}$, $R^{5b}$, $R^{6b}$, and $R^{7b}$ is —C(=O)OH. In some embodiments, at least two of $R^{2b}$, $R^{3b}$, $R^{4b}$, $R^{5b}$, $R^{6b}$, and $R^{7b}$ is —C(=O)OH. In some embodiments, $R^{2b}$ is —C(=O)OH. In some embodiments, $R^{3b}$ is —C(=O)OH. In some embodiments, $R^{4b}$ is —C(=O)OH. In some embodiments, $R^{5b}$ is —C(=O)OH. In some embodiments, $R^{6b}$ is —C(=O)OH. In some embodiments, $R^{7b}$ is —C(=O)OH.

In some embodiments, at least one of $R^{2b}$, $R^{3b}$, $R^{4b}$, $R^{5b}$, $R^{6b}$, and $R^{7b}$ is HO—$C_{1-3}$ alkylene. In some embodiments, at least two of $R^{2b}$, $R^{3b}$, $R^{4b}$, $R^{5b}$, $R^{6b}$, and $R^{7b}$ is HO—$C_{1-3}$ alkylene. In some embodiments, $R^{2b}$ is HO—$C_{1-3}$ alkylene. In some embodiments, $R^{3b}$ is HO—$C_{1-3}$ alkylene. In some embodiments, $R^{4b}$ is HO—$C_{1-3}$ alkylene. In some embodiments, $R^{5b}$ is HO—$C_{1-3}$ alkylene. In some embodiments, $R^{6b}$ is HO—$C_{1-3}$ alkylene. In some embodiments, $R^{7b}$ is HO—$C_{1-3}$ alkylene.

In some embodiments, at least one of $R^{2b}$, $R^{3b}$, $R^{4b}$, $R^{5b}$, $R^{6b}$, and $R^{7b}$ is OH. In some embodiments, at least two of $R^{2b}$, $R^{3b}$, $R^{4b}$, $R^{5b}$, $R^{6b}$, and $R^{7b}$ is OH. In some embodiments, $R^{2b}$ is OH. In some embodiments, $R^{3b}$ is OH. In some embodiments, $R^{4b}$ is OH. In some embodiments, $R^{5b}$ is OH. In some embodiments, $R^{6b}$ is OH. In some embodiments, $R^{7b}$ is OH.

In some embodiments, the compound of Formula (II) is selected from:

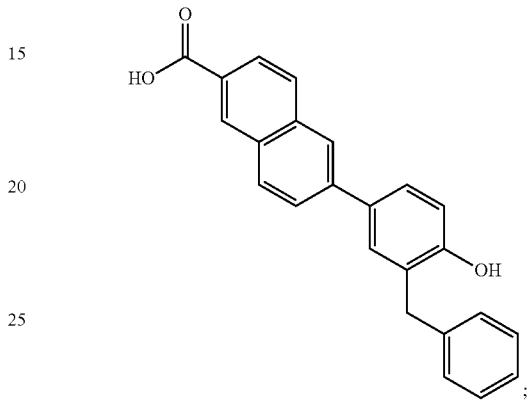

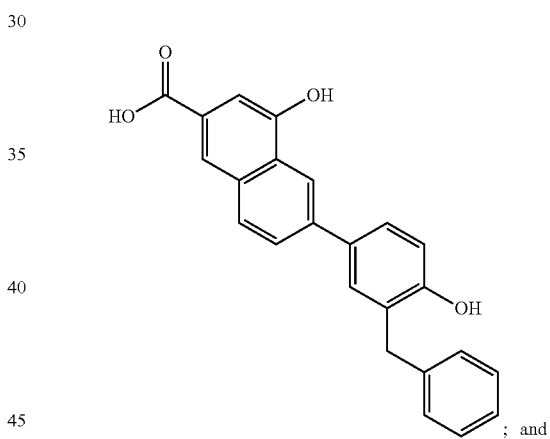

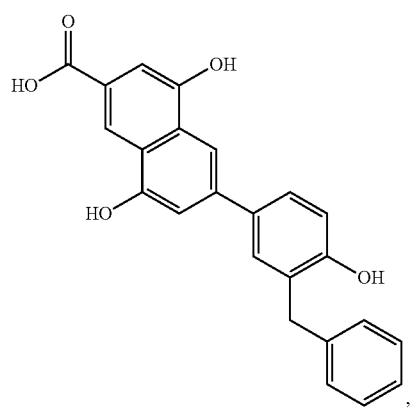

or a pharmaceutically acceptable salt thereof.

In some embodiments, the present disclosure provides a compound of Formula (III):

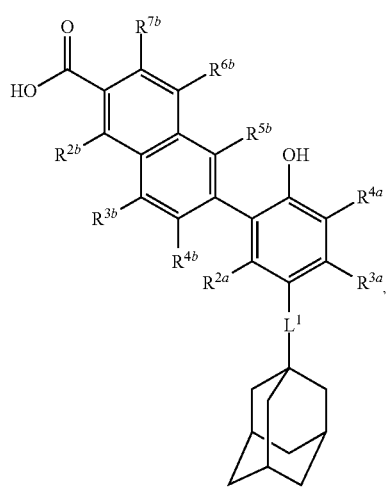

or a pharmaceutically acceptable salt thereof, wherein:
$L^1$ is $C_{1-3}$ alkylene, or $L^1$ is absent;
$R^{2a}$, $R^{3a}$, and $R^{4a}$ are each independently selected from H and OH; and
$R^{2b}$, $R^{3b}$, $R^{4b}$, $R^{5b}$, $R^{6b}$, and $R^{7b}$ are each independently selected from H, OH, HO—$C_{1-3}$ alkylene, and —C(=O)OH.

In some embodiments, the compound of Formula (III) has formula:

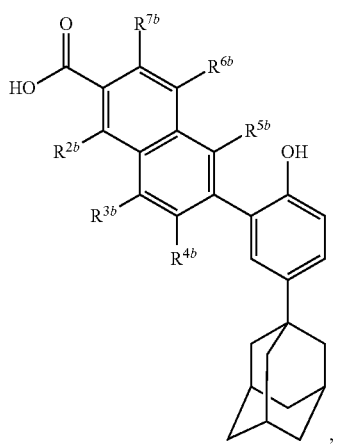

or a pharmaceutically acceptable salt thereof.

In some embodiments, $L^1$ is methylene. In some embodiments, $L^1$ is ethylene (1,2-ethylene or 1,2-ethylene). In some embodiments, $L^1$ is propylene (e.g., 1,1-propylene, 1,2-propylene, or 1,3-propylene). In some embodiments, $L^1$ is absent.

In some embodiments, at least one of $R^{2a}$, $R^{3a}$, and $R^{4a}$ is OH. In some embodiments, $R^{2a}$ is OH. In some embodiments, $R^{3a}$ is OH. In some embodiments, $R^{4a}$ is OH. In some embodiments, $R^{2a}$, $R^{3a}$, and $R^{4a}$ are each H. In some embodiments, $R^{2a}$ is H. In some embodiments, $R^{3a}$ is H. In some embodiments, $R^{2a}$ is H.

In some embodiments, $R^{2b}$, $R^{3b}$, $R^{4b}$, $R^{5b}$, $R^{6b}$, and $R^{7b}$ are each H. In some embodiments, $R^{2b}$, $R^{3b}$, $R^{4b}$, $R^{5b}$, $R^{6b}$, and $R^{7b}$ are each independently selected from H, OH, and —C(=O)OH. In some embodiments, $R^{2b}$, $R^{3b}$, $R^{4b}$, $R^{5b}$, $R^{6b}$, and $R^{7b}$ are each independently selected from H and OH. In some embodiments, $R^{2b}$, $R^{3b}$, $R^{4b}$, $R^{5b}$, $R^{6b}$, and $R^{7b}$ are each independently selected from H and —C(=O)OH. In some embodiments, $R^{2b}$, $R^{3b}$, $R^{4b}$, $R^{5b}$, $R^{6b}$, and $R^{7b}$ are each independently selected from H and HO—$C_{1-3}$ alkylene. In some embodiments, $R^{2b}$, $R^{3b}$, $R^{4b}$, $R^{5b}$, $R^{6b}$, and $R^{7b}$ are each independently selected from OH and HO—$C_{1-3}$ alkylene.

In some embodiments, at least one of $R^{2b}$, $R^{3b}$, $R^{4b}$, $R^{5b}$, $R^{6b}$, and $R^{7b}$ is —C(=O)OH. In some embodiments, at least two of $R^{2b}$, $R^{3b}$, $R^{4b}$, $R^{5b}$, $R^{6b}$, and $R^{7b}$ is —C(=O)OH. In some embodiments, $R^{2b}$ is —C(=O)OH. In some embodiments, $R^{3b}$ is —C(=O)OH. In some embodiments, $R^{4b}$ is —C(=O)OH. In some embodiments, $R^{5b}$ is —C(=O)OH. In some embodiments, $R^{6b}$ is —C(=O)OH. In some embodiments, $R^{7b}$ is —C(=O)OH.

In some embodiments, at least one of $R^{2b}$, $R^{3b}$, $R^{4b}$, $R^{5b}$, $R^{6b}$, and $R^{7b}$ is HO—$C_{1-3}$ alkylene. In some embodiments, at least two of $R^{2b}$, $R^{3b}$, $R^{4b}$, $R^{5b}$, $R^{6b}$, and $R^{7b}$ is HO—$C_{1-3}$ alkylene. In some embodiments, $R^{2b}$ is HO—$C_{1-3}$ alkylene. In some embodiments, $R^{3b}$ is HO—$C_{1-3}$ alkylene. In some embodiments, $R^{4b}$ is HO—$C_{1-3}$ alkylene. In some embodiments, $R^{5b}$ is HO—$C_{1-3}$ alkylene. In some embodiments, $R^{6b}$ is HO—$C_{1-3}$ alkylene. In some embodiments, $R^{7b}$ is HO—$C_{1-3}$ alkylene.

In some embodiments, at least one of $R^{2b}$, $R^{3b}$, $R^{4b}$, $R^{5b}$, $R^{6b}$, and $R^{7b}$ is OH. In some embodiments, at least two of $R^{2b}$, $R^{3b}$, $R^{4b}$, $R^{5b}$, $R^{6b}$, and $R^{7b}$ is OH. In some embodiments, $R^{2b}$ is OH. In some embodiments, $R^{3b}$ is OH. In some embodiments, $R^{4b}$ is OH. In some embodiments, $R^{5b}$ is OH. In some embodiments, $R^{6b}$ is OH. In some embodiments, $R^{7b}$ is OH.

In some embodiments, the compound of Formula (III) is selected from:

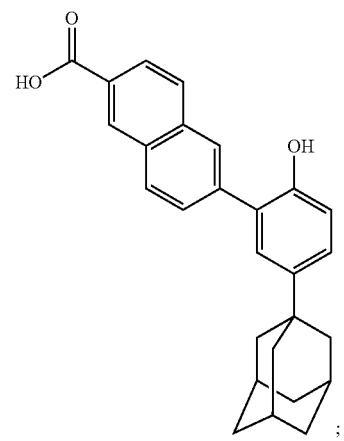

;

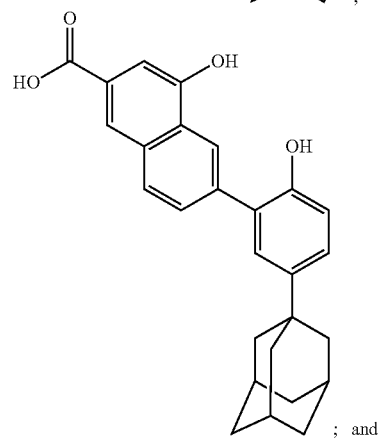

; and

-continued

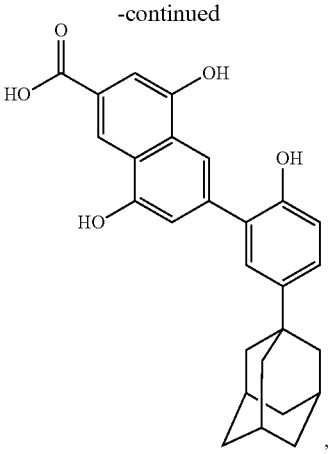

, or pharmaceutically acceptable salt thereof.

In some embodiments, the present disclosure provides a a compound of Formula (IV):

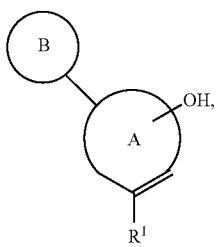
(IV)

or a pharmaceutically acceptable salt thereof, wherein:

$R^1$ is selected from any one of the following moieties:

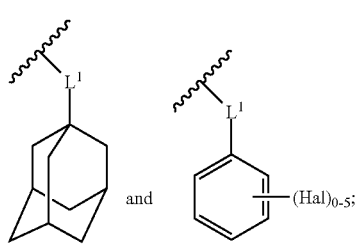

$L^1$ is $C_{1-3}$ alkylene, or $L^1$ is absent;
$L^2$ is $C_{1-3}$ alkylene;
each Hal is independently a halogen;
ring A is selected from the group consisting of phenyl and naphthyl, each of which is optionally substituted by 1, 2, or 3 OH groups; and ring B is selected from the group consisting of phenyl and naphthyl, each of which is optionally substituted by 1, 2, 3, 4, 5, or 6 groups independently selected from OH, HO—$C_{1-3}$ alkylene, —C(=O)N(di-$C_{1-4}$ alkyl), —C(=O)NH($C_{1-4}$ alkyl), —C(=O)NH$_2$, —C(=O)—$C_{1-4}$ alkoxy, —C(=O)OH, and —(CH=CH)—C(=O)OH.

In some embodiments, $R^1$ is:

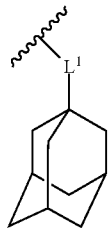

In some embodiments, $L^1$ is methylene. In some embodiments, $L^1$ is ethylene (1,2-ethylene or 1,2-ethylene). In some embodiments, $L^1$ is propylene (e.g., 1,1-propylene, 1,2-propylene, or 1,3-propylene). In some embodiments, $L^1$ is absent and $R^1$ has formula:

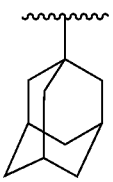

In some embodiments, $R^1$ is:

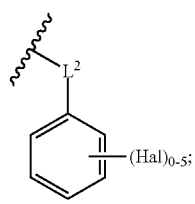

In some embodiments, $L^2$ is ethylene (1,2-ethylene or 1,2-ethylene). In some embodiments, $L^2$ is propylene (e.g., 1,1-propylene, 1,2-propylene, or 1,3-propylene). In some embodiments, $L^2$ is methylene and $R^1$ has formula:

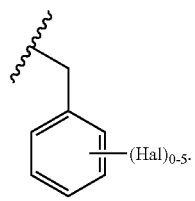

In some embodiments, each Hal is independently selected from: Cl, F, Br, and I. In some embodiments, at least one Hal is F. In some embodiments, at least one Hal is Cl.

In some embodiments, $R^1$ is selected from:

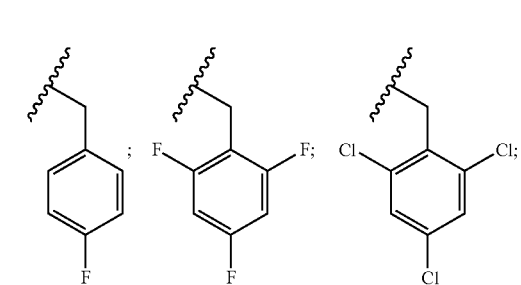

-continued

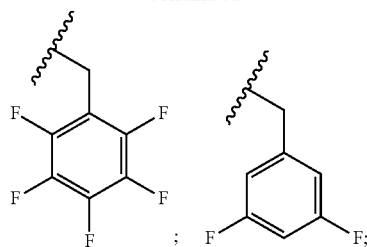

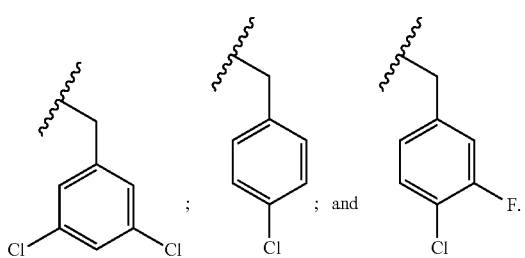

In some embodiments, the compound of Formula (IV) has formula:

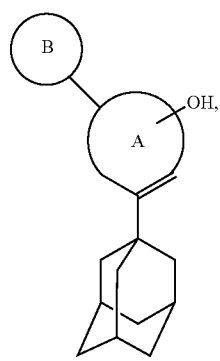

or a pharmaceutically acceptable salt thereof.

In some embodiments, the compound of Formula (IV) has formula:

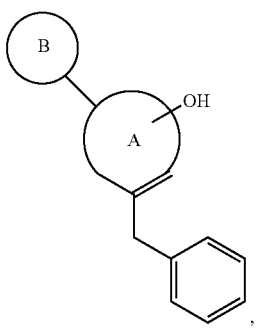

or a pharmaceutically acceptable salt thereof.

In some embodiments, the compound of Formula (IV) has formula:

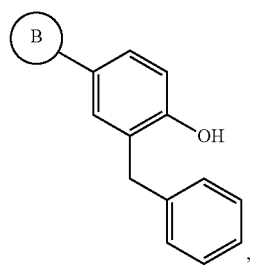

or a pharmaceutically acceptable salt thereof.

In some embodiments, the compound of Formula (IV) has formula:

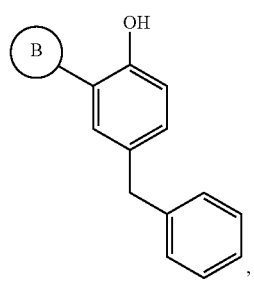

or a pharmaceutically acceptable salt thereof.

In some embodiments, the compound of Formula (IV) has formula:

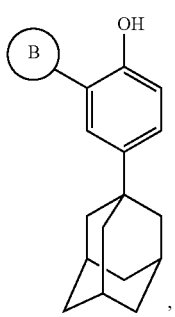

or a pharmaceutically acceptable salt thereof.

In some embodiments, the compound of Formula (IV) has formula:

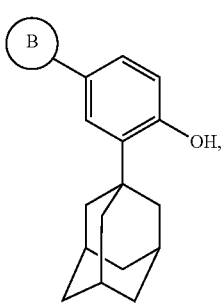

or a pharmaceutically acceptable salt thereof.

In some embodiments, ring A is phenyl.

In some embodiments, ring A is naphthyl.

In some embodiments, ring B is phenyl.

In some embodiments, ring B is naphthyl.

In some embodiments, ring A is phenyl and ring B is phenyl.

In some embodiments, ring A is phenyl and ring B is naphthyl.

In some embodiments, ring A is naphthyl and ring B is phenyl.

In some embodiments, ring B is optionally substituted with 1, 2, or 3 groups independently selected from OH, HO—$C_{1-3}$ alkylene, C(=O)NH($C_{1-4}$ alkyl), —C(=O)NH$_2$, —C(=O)—$C_{1-4}$ alkoxy, and —C(=O)OH. In some embodiments, ring B is optionally substituted with 1, 2, or 3 groups independently selected from OH, HO—$C_{1-3}$ alkylene, and —C(=O)OH. In some embodiments, ring B is optionally substituted with 1, 2, or 3 groups independently selected from HO—$C_{1-3}$ alkylene, and —C(=O)OH.

In some embodiments, ring B is substituted with at least one group —C(=O)OH.

In some embodiments, ring B is substituted with at least one group HO—$C_{1-3}$ alkylene.

In some embodiments, ring A is optionally substituted by one OH group.

In some embodiments, the compound of Formula (IV) is selected from any one of the following compounds:

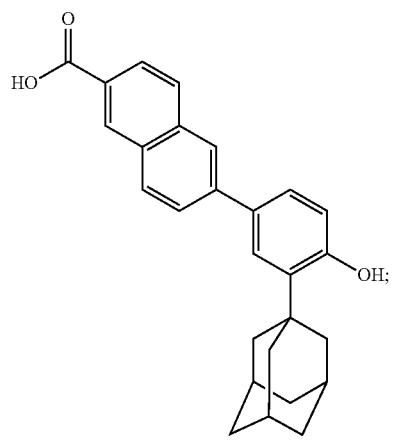

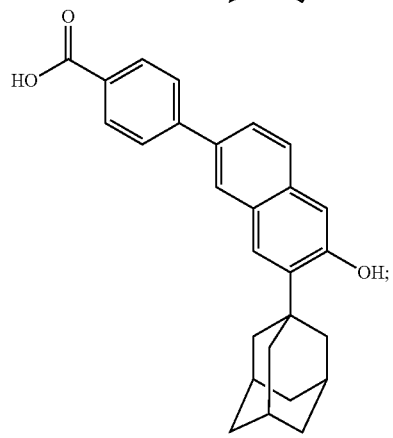

-continued

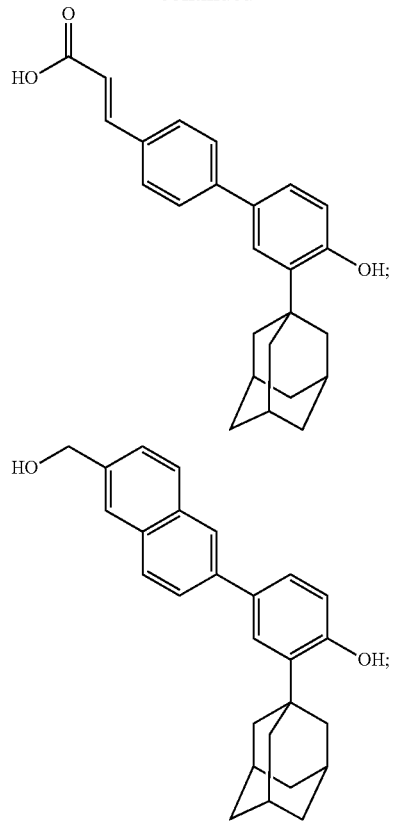

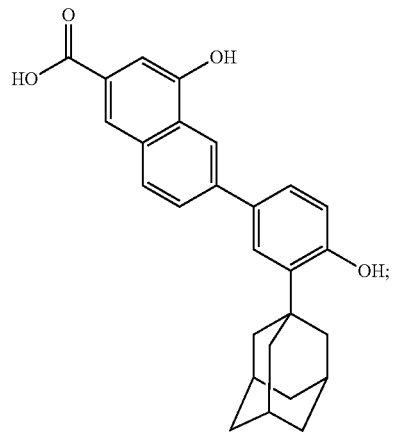

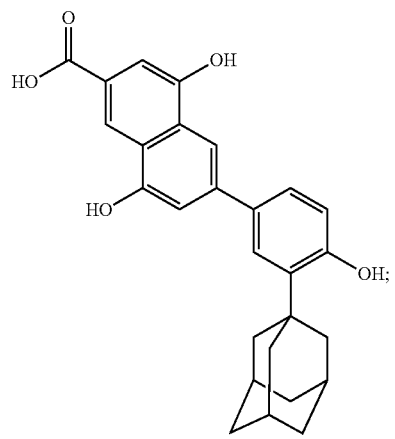

37
-continued
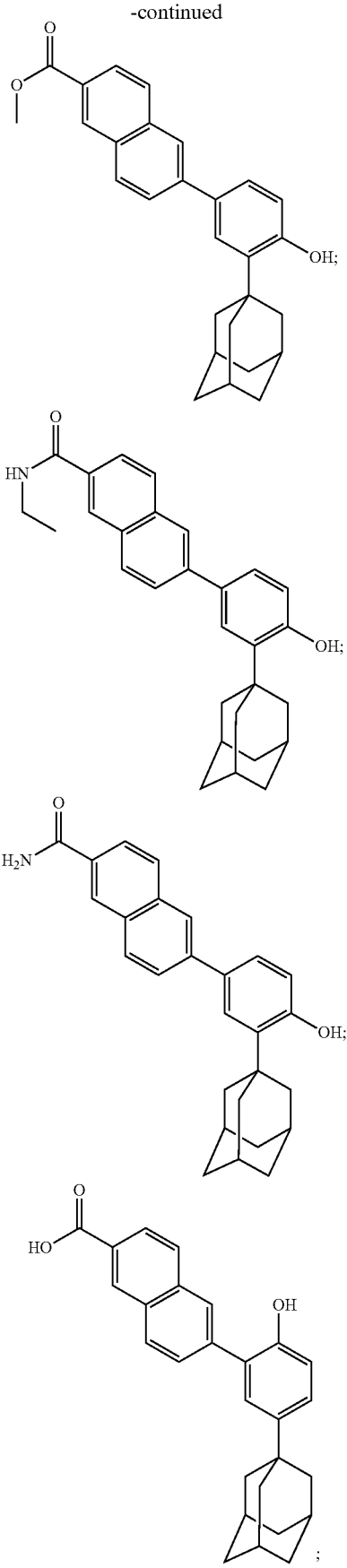
38
-continued
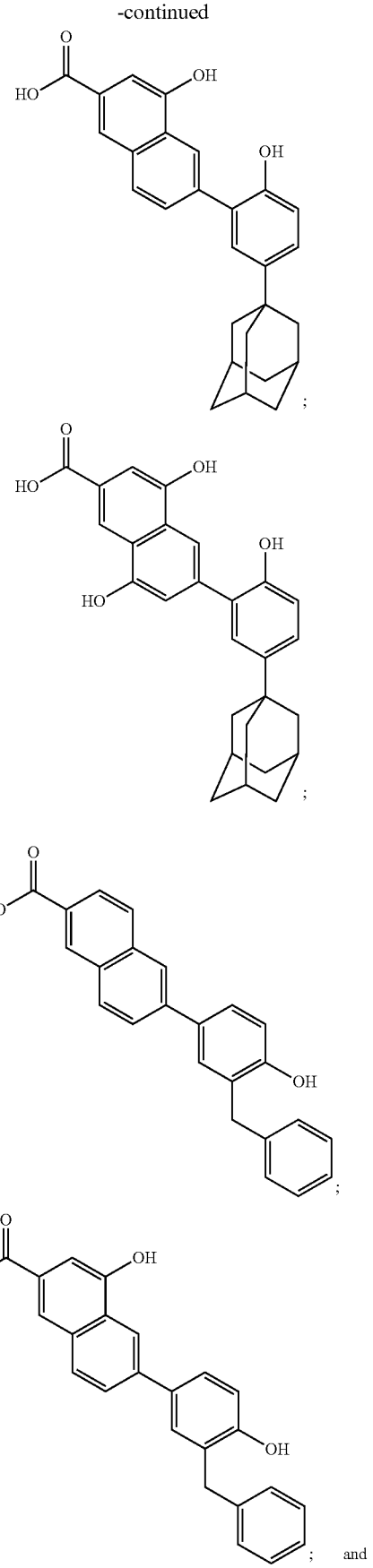
; and

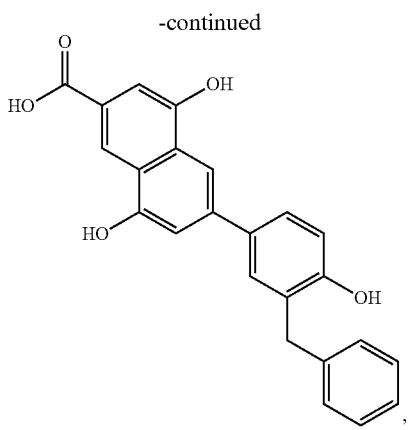

or a pharmaceutically acceptable salt thereof.

In some embodiments, a salt (e.g., pharmaceutically acceptable salt) of a compound of Formulae I, II, III or IV is formed between an acid and a basic group of the compound, such as an amino functional group, or a base and an acidic group of the compound, such as a carboxyl functional group. According to another embodiment, the compound is a pharmaceutically acceptable acid addition salt.

In some embodiments, acids commonly employed to form pharmaceutically acceptable salts of the compounds of Formulae I, II, III or IV include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

In some embodiments, bases commonly employed to form pharmaceutically acceptable salts of the compounds of Formulae I, II, III or IV include hydroxides of alkali metals, including sodium, potassium, and lithium; hydroxides of alkaline earth metals such as calcium and magnesium; hydroxides of other metals, such as aluminum and zinc; ammonia, organic amines such as unsubstituted or hydroxyl-substituted mono-, di-, or tri-alkylamines, dicyclohexylamine; tributyl amine; pyridine; N-methyl, N-ethylamine; diethylamine; triethylamine; mono-, bis-, or tris-(2-OH—(C1-C6)-alkylamine), such as N,N-dimethyl-N-(2-hydroxyethyl)amine or tri-(2-hydroxyethyl)amine; N-methyl-D-glucamine; morpholine; thiomorpholine; piperidine; pyrrolidine; and amino acids such as arginine, lysine, and the like.

In some embodiments, the compounds of Formulae I, II, III or IV, or pharmaceutically acceptable salts thereof, are substantially isolated.

Methods of Making of Antibacterial Compounds

Compounds of Formulae I, II, III or IV, including salts thereof, can be prepared using known organic synthesis techniques and can be synthesized according to any of numerous possible synthetic routes. In some cases, compounds as provided herein are commercially available.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing the compounds provided herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of the compounds provided herein can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, $4^{th}$ Ed., Wiley & Sons, Inc., New York (2006).

In one example, compounds of Formula IV can be synthesized according to the methods and procedures described, for example, in U.S. Pat. Nos. 6,127,415, 5,602,104, 8,101, 793, and 4,200,738; or compounds of Formula IV can be readily prepared according to numerous methods and procedures available to one of ordinary skill in the art. Such methods and procedures can be found, for example, in Smith et al., *March's Advanced Organic Chemistry: Reactions,*

*Mechanisms, and Structure*, 6th Ed. (Wiley, 2007). Suitable starting materials and intermediates are readily available from various commercial sources. The compounds of any of the formulae disclosed herein may also be prepare using methods analogous to those described in Example 1 and shown in FIG. 10.

Methods of Use

Inhibition of Bacterial Pathogens

In some embodiments, the present application is directed to a method of killing or inhibiting growth of bacteria, the method comprising contacting the bacteria with an effective amount of a compound of Formulae I, II, III, or IV, or a pharmaceutically acceptable salt thereof, as described herein. In some embodiments, the compound kills the bacteria by disrupting the bacterial membrane.

In some embodiments, the minimal inhibitory concentration (MIC) of a compound of any one of Formulae I, II, III, or IV for killing or inhibiting growth of bacteria (e.g., any one of bacteria described herein) is from about 0.1 µg/ml to about 4 µg/ml, from about 0.1 µg/ml to about 3 µg/ml, from about 0.1 µg/ml to about 4 µg/ml, from about 2 µg/ml, from about 0.25 µg/ml to about 4 µg/ml, from about 0.5 g/ml to about 3 µg/ml, from about 0.5 µg/ml to about 2 µg/ml, or from about 1 g/ml to about 2 µg/ml. In some embodiments, the minimal inhibitory concentration (MIC) of a compound of any one of Formulae I, II, III, or IV for killing or inhibiting growth of bacteria is about 0.25 µg/ml, about 0.5 µg/ml, about 1 µg/ml, about 1.5 g/ml, about 2 µg/ml, about 3 µg/ml, or about 4 µg/ml.

In some embodiments, the bacteria (e.g., any one of bacteria described herein) is resistant to one or more of other antibiotic agents (e.g., antibiotic agents disclosed herein). In some embodiments, the bacteria is at least 2-fold, 4-fold, 8-fold, 10-fold, 24-fold, 48-fold, 100-fold, 256-fold, 512-fold or 1000-fold resistant to one or more of other antibiotic agents. In some embodiments, the bacteria is multi-drug resistant (MDR). In some embodiments, any one of bacteria described herein is resistant to methicillin, vancomycin, rifampicin, linezolid, daptomycin, gentamicin and/or ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, linezolid, daptomycin, gentamicin and/or ciprofloxacin. In some embodiments, any one of bacteria described herein is resistant to an antibiotic selected from methicillin, vancomycin, rifampicin, gentamicin and ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, gentamicin and ciprofloxacin. In some embodiments, any one of bacteria described herein is resistant to methicillin, vancomycin, rifampicin, gentamicin and ciprofloxacin. In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to methicillin, vancomycin, rifampicin, gentamicin and ciprofloxacin.

In some embodiments, the bacteria is not resistant to a compound of Formulae I, II, III, or IV. In some embodiments, the bacteria is at most 1.5-fold resistant to a compound of Formulae I, II, III, or IV. In some embodiments, the bacteria is at most 2-fold resistant to a compound of Formulae I, II, III, or IV.

In some embodiments, any one of bacteria described herein is resistant to one or more of other antibiotic agents and is not resistant to a compound of Formulae I, II, III, or IV.

In some embodiments, any one of bacteria described herein is at least 2-fold, at least 4-fold, at least 8-fold, at least 10-fold, at least 24-fold, at least 48-fold, at least 100-fold, at least 256-fold, at least 512-fold, or at least 1000-fold resistant to one or more of other antibiotic agents and at most 1.5-fold or at most 2-fold resistant to a compound of Formulae I, II, III, or IV.

In some embodiments, the bacteria is Gram-positive bacteria.

In some embodiments, the bacteria is a member of a genus selected from the group consisting of *Staphylococcus* (including coagulase negative and coagulase positive), *Streptococcus*, *Peptococcus*, *Enterococcus*, and *Bacillus*.

In some embodiments, the bacteria is a member of *Staphylococcus* genus and the species of bacteria is selected from the group consisting of *S. aureus*, methicillin-susceptible *S. aureus* (MSSA), coagulase negative staphylococci, methicillin-resistant *S. aureus* (MRSA), vancomycin-resistant *S. aureus* (VRSA), *S. arlettae*, *S. agnetis*, *S. auricularis*, *S. capitis*, *S. caprae*, *S. carnosus*, *S. caseolyticus*, *S. chromogenes*, *S. cohnii*, *S. condimenti*, *S. delphini*, *S. devriesei*, *S. epidermidis*, *S. equorum*, *S. felis*, *S. fleurettii*, *S. gallinarum*, *S. haemolyticus*, *S. hominis*, *S. hyicus*, *S. intermedius*, *S. kloosii*, *S. leei*, *S. lentus*, *S. lugdunensis*, *S. lutrae*, *S. massiliensis*, *S. microti*, *S. muscae*, *S. nepalensis*, *S. pasteuri*, *S. pettenkoferi*, *S. piscifermentans*, *S. pseudintermedius*, *S. pseudolugdunensis*, *S. pulvereri*, *S. rostri*, *S. saccharolyticus*, *S. saprophyticus*, *S. schleiferi*, *S. sciuri*, *S. simiae*, *S. simulans*, *S. stepanovicii*, *S. succinus*, *S. vitulinus*, *S. warneri*, and *S. xylosus*.

In some embodiments, the bacteria is *S. aureus* which is at least 2-fold, at least 4-fold, at least 8-fold, at least 10-fold, at least 24-fold, at least 48-fold, at least 100-fold, at least 256-fold, at least 512-fold, or at least 1000-fold resistant to an antibiotic selected from methicillin, vancomycin, rifampicin, linezolid, daptomycin, gentamicin and ciprofloxacin.

In some embodiments, the bacteria is a member of Peptococcus genus and the species of bacteria is *P. magnus*.

In some embodiments, the bacteria is a member of *Streptococcus* genus and the species of bacteria is selected from the group consisting of *S. agalactiae*, *S. anginosus*, *S. bovis*, *S. canis*, *S. constellatus*, *S. dysgalactiae*, *S. equinus*, *S. iniae*, *S. intermedius*, *S. milleri*, *S. mitis*, *S. mutans*, *S. oralis*, *S. parasanguinis*, *S. peroris*, *S. pneumoniae*, *S. pseudopneumoniae*, *S. pyogenes*, *S. ratti*, *S. salivarius*, *S. tigurinus*, *S. thermophilus*, *S. sanguinis*, *S. sobrinus*, *S. suis*, *S. uberis*, *S. vestibularis*, *S. viridans*, and *S. zooepidemicus*.

In some embodiments, the bacteria is a member of *Enterococcus* genus and the species of bacteria is selected from the group consisting of *E. avium*, *E. durans*, *E. faecalis*, *E. gallinarum*, *E. haemoperoxidus*, *E. hirae*, *E. malodoratus*, *E. moraviensis*, *E. mundtii*, *E. pseudoavium*, *E. raffinosus*, *E. solitaries*, and *E. faecium*.

In some embodiments, the bacteria is a member of *Propionibacterium* genus. In such embodiments, the bacteria is *P. acnes*.

In some embodiments, the bacteria is Gram-negative bacteria.

In some embodiments, the bacteria is a member of a family selected from the group consisting of Enterobacteriaceae, Helicobacteraceae, Campylobacteraceae, Neisseriaceae, Pseudomonadaceae, Moraxellaceae, Xanthomonadaceae, Pasteurellaceae, and Legionellaceae.

In some embodiments, the bacteria is a member of a genus selected from the group consisting of *Citrobacter, Enterobacter, Escherichia, Klebsiella, Pantoea, Proteus, Salmonella, Serratia, Shigella, Yersinia, Helicobacter, Wolinella, Campylobacter, Arcobacter, Neisseria, Francisella, Pseudomonas, Acinetobacter, Moraxella, Stenotrophomonas, Haemophilus, Pasteurella*, and *Legionella*.

In some embodiments, the bacteria is a member of *Citrobacter* genus and the species of bacteria is selected from the group consisting of *C. amalonaticus, C. braakii, C. diversus, C. farmer, C. freundii, C. gillenii, C. koseri, C. murliniae, C. rodentium, C. sedlakii, C. werkmanii*, and *C. youngae*.

In some embodiments, the bacteria is a member of *Enterobacter* genus and the species of bacteria is selected from the group consisting of *E. aerogenes, E. amnigenus, E. agglomerans, E. arachidis, E. asburiae, E. cancerogenous, E. cloacae, E. cowanii, E. dissolvens, E. gergoviae, E. helveticus, E. hormaechei, E. intermedius, E. kobei, E. ludwigii, E. mori, E. nimipressuralis, E. oryzae, E. pulveris, E. pyrinus, E. radicincitans, E. taylorae, E. turicensis, E. sakazakii*, and *E.* spp.

In some embodiments, the bacteria is a member of *Escherichia* genus and the species of bacteria is selected from the group consisting of *E. albertii, E. blattae, E. coli, E. fergusonii, E. hermannii*, and *E. vulneris*.

In some embodiments, the bacteria is a member of *Klebsiella* genus and the species of bacteria is selected from the group consisting of *K. granulomatis, K. oxytoca, K. pneumoniae, K. terrigena*, and *K. planticola*.

In some embodiments, the bacteria is a member of *Pantoea* genus and the species of bacteria is selected from the group consisting of *P. agglomerans, P. ananatis, P. citrea, P. dispersa, P. punctata, P. stewartii, P. terrea*, and *P. vagans*.

In some embodiments, the bacteria is a member of *Proteus* genus and the species of bacteria is selected from the group consisting of *P. hauseri, P. mirabilis, P. myxofaciens, P. penneri*, and *P. vulgaris*.

In some embodiments, the bacteria is a member of *Salmonella* genus and the species of bacteria is selected from the group consisting of *S. bongori*, and *S. enterica*.

In some embodiments, the bacteria is a member of *Serratia* genus and the species of bacteria is selected from the group consisting of *S. entomophila, S. ficaria, S. fonticola, S. grimesii, S. liquefaciens, S. marcescens, S. odorifera, S. plymuthica, S. proteamaculans, S. quinivorans, S. rubidaea*, and *S. symbiotica*.

In some embodiments, the bacteria is a member of *Shigella* genus and the species of bacteria is selected from the group consisting of *S. boydii, S. dysenteriae, S. flexneri*, and *S. sonnei*.

In some embodiments, the bacteria is a member of *Yersinia* genus and the species of bacteria is selected from the group consisting of *Y. pestis, Y. pseudotuberculosis*, and *Y. enterocolitica*.

In some embodiments, the bacteria is a member of *Helicobacter* genus and the species of bacteria is selected from the group consisting of *H. acinonychis, H. anseris, H. aurati, H. baculiformis, H. bilis, H. bizzozeronii, H. brantae, H. canadensis, H. canis, H. cetorum, H. cholecystus, H. cinaedi, H. cynogastricus, H. equorum, H. felis, H. fennelliae, H. ganmani, H. heilmannii, H. hepaticus, H. mesocricetorum, H. macacae, H. marmotae, H. mastomyrinus, H. mesocricetorum, H. muridarum, H. mustelae, H. pametensis, H. pullorum, H. pylori, H. rappini, H. rodentium, H. salomonis, H. suis, H. trogontum, H. typhlonius*, and *H. winghamensis*.

In some embodiments, the bacteria is a member of *Campylobacter* genus and the species of bacteria is selected from the group consisting of *C. avium, C. butzleri, C. canadensis, C. cinaedi, C. coli, C. concisus, C. corcagiensis, C. cryaerophilus, C. cuniculorum, C. curvus, C. fennelliae, C. fetus, C. gracilis, C. helveticus, C. hominis, C. hyoilei, C. hyointestinalis, C. insulaenigrae, C. jejuni, C. lanienae, C. lari, C. mucosalis, C. mustelae, C. nitrofigilis, C. peloridis, C. pylori, C. rectus, C. showae, C. sputorum, C. subantarcticus, C. upsaliensis, C. ureolyticus*, and *C. volucris*.

In some embodiments, the bacteria is a member of *Arcobacter* genus and the species of bacteria is selected from the group consisting of *A. bivalviorum, A. butzleri, A. cibarius, A. cryaerophilus, A. defluvii, A. ellisii, A. halophilus, A. marinus, A. molluscorum, A. mytili, A. nitrofigilis, A. skirrowii, A. thereius, A. trophiarum*, and *A. venerupis*.

In some embodiments, the bacteria is a member of *Neisseria* genus and the species of bacteria is selected from the group consisting of *N. bacilliformis, N. cinerea, N. denitrificans, N. elongata, N. flavescens, N. gonorrhoeae, N. lactamica, N. macacae, N. meningitidis, N. mucosa, N. pharyngis, N. polysaccharea, N. sicca, N. subflava*, and *N. weaver*.

In some embodiments, the bacteria is a member of *Francisella* genus and the species of bacteria is selected from the group consisting of *F. tularensis, F. novicida, F. hispaniensis, W. persica, F. noatunensis, F. philomiragia, F. halioticida, F. endociliophora*, and *F. guangzhouensis*.

In some embodiments, the bacteria is a member of *Pseudomonas* genus and the species of bacteria is selected from the group consisting of *P. aeruginosa, P. oryzihabitans*, and *P. plecoglossicida*.

In some embodiments, the bacteria is a member of *Acinetobacter* genus and the species of bacteria is *A. baumannii*.

In some embodiments, the bacteria is a member of *Moraxella* genus and the species of bacteria is selected from the group consisting of *M. catarrhalis, M. lacunata*, and *M. bovis*.

In some embodiments, the bacteria is a member of *Stenotrophomonas* genus and the species of bacteria is *S. maltophilia*.

In some embodiments, the bacteria is a member of *Haemophilus* genus and the species of bacteria is selected from the group consisting of *H. aegyptius, H. aphrophilus, H. avium, H. ducreyi, H. felis, H. haemolyticus, H. influenzae, H. parainfluenzae, H. paracuniculus, H. parahaemolyticus, H. pittmaniae, Haemophilus segnis*, and *H. somnus*.

In some embodiments, the bacteria is a member of *Pasteurella* genus and the species of bacteria is selected from the group consisting of *P. multocida, P. stomatis, P. dagmatis, P. canis, P. bettyae*, and *P. anatis*.

In some embodiments, the bacteria is a member of *Legionella* genus and the species of bacteria is selected from the group consisting of *L. pneumophila, L. anisa, L. bozemanae, L. cincinnatiensis, L. gormanii, L. jordani, L. longbeachae, L. maceachernii, L. micdadei, L. sainthelensi, L. wadsworthii*, and *L. waltersii*.

In some embodiments, the bacteria is a member of *Mycobacterium* genus and the species of bacteria is selected from a group consisting of *M. tuberculosis* and *M. smegmatic*.

In some embodiments, the bacteria is a member of a genus selected from: *Acinetobacter, Burkholderia, Acinetobacter, Burkholderia, Klebsiella, Pseudomonas*, and *Escherichia*. In such embodiments, the bacteria is a member of a species selected from: *K. pneumoniae, P. aeruginosa*, Enterobacteriaceae, and *E. coli*.

Treating Bacterial Infections

In some embodiments, the present application is also directed to a method of treating a bacterial infection in a subject, the method comprising administering to the subject in need thereof a therapeutically effective amount of a compound of Formulae I, II, III, or IV, or a pharmaceutically acceptable salt thereof, as described herein. In some embodiments, the bacterial infection is resistant to treatment by one or more other antibiotic agents (e.g., any one of antibiotic agents described herein).

In some embodiments, the bacterial infection is caused by any one of the bacteria described herein (e.g., *P. acnes*, or MRSA). In some embodiments, the bacterial infection is resistant to treatment with one or more of the antibiotic agents described herein (e.g., bacterial infection is resistant to treatment with methicillin, vancomycin, rifampicin, gentamicin and/or ciprofloxacin). In these embodiments, the bacterial infection is characterized as persistent to treatment with one or more available antibiotic agents.

In some embodiments, the bacterial infection is a skin infection. In some aspects of these embodiments, the skin infection is selected from the group consisting of acne, pimples, impetigo, boils, cellulitis, folliculitis, carbuncles, scalded skin syndrome, skin abscesses, atopic dermatitis, and typhoid fever. In some embodiments, the bacterial infection is skin infection caused by *P. acnes*. In such embodiments, the skin infection is acne. In some embodiments, the bacterial infection is a skin and soft tissue infection (e.g., acne).

In some embodiments, the bacterial infection is a respiratory infection. In some aspects of these embodiments, the respiratory infection is selected from the group consisting of upper respiratory tract infection, bronchopneumonia, atypical pneumonia, tuberculosis, *Mycobacterium tuberculosis*, pneumonia, anaerobic pleuropulmonary infection, ventilator-associated pneumonia, aspiration pneumonia, lung abscess, bronchitis, chronic obstructive pulmonary disease, obstructive pulmonary disease, Pontiac fever, and legionellosis.

In some embodiments, the bacterial infection is a wound infection. In some aspects of these embodiments, the wound infection is a postsurgical wound infection. In some embodiments, the bacterial infection is a blood stream infection. In some aspects of these embodiments, the blood stream infection is bacteremia or sepsis. In some embodiments, the bacterial infection is a pelvic infection. In some aspects of the embodiments, the pelvic infection is bacterial vaginosis.

In some embodiments, the bacterial infection is a gastrointestinal infection. In some aspects of these embodiments, the gastrointestinal infection is selected from the group consisting of peptic ulcer, chronic gastritis, duodenitis, gastroenteritis, diarrhea, dysentery, diphtheria, food poisoning and foodborne illness.

In some embodiments, the bacterial infection is a bone, joint or muscle infection. In some aspects of these embodiments, the bone, joint or muscle infection is selected from the group consisting of tetanus, secondary meningitis, meningitis, neonatal meningitis, sinusitis, laryngitis, arthritis, septic arthritis, Bartholin gland abscess, chancroid, osteomyelitis, endocarditis, mediastinitis, pericarditis, peritonitis, otitis media, blepharoconjunctivitis, keratoconjunctivitis, and conjunctivitis.

In some embodiments, the bacterial infection is selected from the group consisting of a dental infection, a zoonotic infection, an invasive systemic infection, a urinary tract infection, an abdominal infection, a CNS infection, an endovascular infection, and a nosocomial infection. In some embodiments, the bacterial infection is selected from the group consisting of syphilis, leprosy, abscesses, sepsis, empyema, and tularemia.

In some embodiments, the bacterial infection is associated with implanted devices (e.g., catheter, ballon catheter, stent, pacer etc). In some embodiments, the bacterial infection is osteomyelitis, endocarditis, or an infection associated with an implanted device, which is caused by a *S. aureus* persister.

In some embodiments, the bacterial infection is a connective tissue infection, or a joint or muscle infection. In some embodiments, the connective tissue or joint infection is caused by *P. acnes*. In such embodiments, the joint infection is an infection of a shoulder, a knee, a hip, or an elbow. In some embodiments, the bacterial infection is septic arthritis (e.g., septic arthritis caused by *P. acnes* or septic arthritis caused by *S. aureus*).

In some embodiments, any one of the bacterial infections described herein is caused by *S. aureus* (e.g., MRSA). In other embodiments, any one of the bacterial infections described herein is caused by *P. acnes*.

Cleaning Compositions

In some embodiments, any one of compounds of any one of Formulae I, II, III, and IV, or a salt thereof, may be used for killing bacteria on a surface (e.g., for disinfecting or sanitizing a surface). The surface may be metallic, plastic, ceramic, or wooden, for example, the surface is a floor, a table, a kitchen counter, a cutting board, or a medical instrument. Hence, any one of the compounds of the present application may be used in a commercial setting for general disinfecting, e.g., in medical and food industries. For these purposes, the compound may be provided in a cleaning composition comprising an acceptable carrier. The carrier(s) are "acceptable" in the sense of being compatible with the other ingredients of the cleaning composition. Acceptable carriers that may be used in a cleaning composition of the present application include, but are not limited to, alcohols, water, surfactants, emollients, stabilizers, thickeners, viscosifiers, and fragrances.

Compositions, Formulations, and Routes of Administration

In some embodiments, the present application also provides pharmaceutical compositions comprising an effective amount of a compound of any one of Formulae I, II, III, and IV, or a pharmaceutically acceptable salt thereof; and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament.

Pharmaceutically acceptable carriers, adjuvants and vehicles that may be used in the pharmaceutical compositions of the present application include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol, and wool fat.

If required, the solubility and bioavailability of the compounds of the present application in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of the present application optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the present application include those suitable for oral, rectal, nasal, topical (including buccal and sublingual), vaginal or parenteral (including subcutaneous, intramuscular, intravenous and intradermal) administration. In certain embodiments, the compound of the formulae herein is administered transdermally (e.g., using a transdermal patch or iontophoretic techniques). Other formulations may conveniently be presented in unit dosage form, e.g., tablets, sustained release capsules, and in liposomes, and may be prepared by any methods well known in the art of pharmacy. See, for example, Remington: The Science and Practice of Pharmacy, Lippincott Williams & Wilkins, Baltimore, Md. (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In some embodiments, the compound any one of Formulae I, II, III, and IV, or a pharmaceutically acceptable salt thereof, is administered orally. Compositions of the present application suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added.

Compositions suitable for oral administration include lozenges comprising the ingredients in a flavored basis, usually sucrose and acacia or tragacanth; and pastilles comprising the active ingredient in an inert basis such as gelatin and glycerin, or sucrose and acacia.

Compositions suitable for parenteral administration include aqueous and non-aqueous sterile injection solutions which may contain antioxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Such injection solutions may be in the form, for example, of a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of the present application may be administered in the form of suppositories for rectal administration. These compositions can be prepared by mixing a compound of the present application with a suitable non-irritating excipient which is solid at room temperature but liquid at the rectal temperature and therefore will melt in the rectum to release the active components. Such materials include, but are not limited to, cocoa butter, beeswax, and polyethylene glycols.

The pharmaceutical compositions of the present application may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art. See, for example, U.S. Pat. No. 6,803,031.

Topical administration of the pharmaceutical compositions of the present application is especially useful when the desired treatment involves areas or organs readily accessible by topical application (e.g., skin and soft tissues).

The topical compositions of the present disclosure can be prepared and used in the form of an aerosol spray, cream, emulsion, solid, liquid, dispersion, foam, oil, gel, hydrogel, lotion, mousse, ointment, powder, patch, pomade, solution, pump spray, stick, towelette, soap, or other forms commonly employed in the art of topical administration and/or cosmetic and skin care formulation. The topical compositions can be in an emulsion form, as a cream or a paste.

In some embodiments, the topical composition comprises a combination of a compound of any one of Formulae I, II, III, and IV, or a pharmaceutically acceptable salt thereof, and one or more additional ingredients, carriers, excipients, or diluents including, but not limited to, absorbents, anti-irritants, anti-acne agents, preservatives, antioxidants, coloring agents/pigments, emollients (moisturizers), emulsifiers, film-forming/holding agents, fragrances, leave-on exfoliants, prescription drugs, preservatives, scrub agents, silicones, skin-identical/repairing agents, slip agents, sunscreen actives, surfactants/detergent cleansing agents, penetration enhancers, and thickeners.

Lists of ingredients, which are well known in the art, are disclosed, for example, in "Cosmetics: Science and Technology," edited by M. S. Balsam and E. Sagarin, 2nd Edition, 1972, Wiley Pub. Co.; "The Chemistry and Manufacture of Cosmetics" by M. G. DeNavasse; and "Harry's Cosmeticology," J. B. Wilkinson et al., 7th Edition, 1982, Chem. Pub. Co.; the disclosures of each of the above being incorporated herein by reference in their entirety. In some embodiments, diluents, carriers, and excipients may include, but are not limited to, polyethylene glycols (such as PEG200, PEG300, PEG400, PEG540, PEG600, PEG1450 or mixtures thereof) and coconut oils (such as propylene glycol dicaprate, coco-caprylate/caprate, propylene glycol dicaprylate/dicaprate, caprylic/capric triglyceride, caprylic/capric/lauric triglyceride, caprylic/capric/linoleic triglyceride, tricaprin, tricaprylin, glyceryl trioleate, neopentyl glycol dicaprylate/dicaprate, caprylic/capric/palmitic/stearic triglceride, or mixtures thereof). In some embodiments, suitable carriers include, but are not limited to, mineral oil, sorbitan monostearate, polysorbate 60, cetyl esters wax, cetearyl alcohol, 2-octyldodecanol, benzyl alcohol, and water. In some embodiments, preservatives may include, but are not limited to, 1,2-hexanediol, benzoic acid, benzothonium chloride, borax, bronopol, butylparaben, caprylyl glycol, chlorophene, chloroxylenol, chlorphenesin, dehydroacetic acid, diazolidinyl urea, DMDM hydantoin, ethylhexylglycerin, ethylparaben, formaldehyde-releasing preservative, Germaben II, hoelen, imidazolidinyl urea, iodopropynyl butylcarbamate, isobutylparaben, methylchloroisothiazolinone, methyldibromo glutaronitrile, Methylisothiazolinone, methylparaben, o-cymen-5-ol, phenoxyethanol, phenoxyisopropanol, phytosphingosine, polyaminopropyl biguanide, potassium sorbate, propylparaben, quaternium-15, sodium benzoate, sodium citrate, sodium dehydroacetate, sodium hexametaphosphate, sodium hydroxymethylglycinate, sodium lactobionate, sodium metabisulfite, sodium sulfite, sorbic acid, and styrax benzoin. In some embodiments, slip agents may include, but are not limited to, amodimethicone, bis-PEG-18 methyl ether dimethyl silane, bis-phenylpropyl dimethicone, butylene glycol, cetyl dimethicone, cetyl dimethicone copolyol, cetyl PEG/PPG-10/1-dimethicone, cyclohexasiloxane, cyclomethicone, cyclopentasiloxane, cyclotetrasiloxane, decylene glycol, diisostearoyl trimethylolpropane siloxy silicate, dimethicone, dimethicone copolyol, dimethicone crosspolymer, dimethiconol, dipropylene glycol, hexylene glycol, hydrolyzed silk, isododecane, methicone, methyl trimethicone, methylsilanol mannuronate, methylsilanol PEG-7 glyceryl cocoate, PEG-10 dimethicone, PEG-10 dimethicone/vinyl dimethicone crosspolymer, PEG-12 dimethicone, PEG/PPG-18/18 dimethicone, PEG/PPG-20/15 dimethicone, pentylene glycol, phenyl trimethicone, polymethylsilsesquioxane, PPG-3 benzyl ether myristate, silica dimethyl silylate, silk powder, siloxane, simethicone, sorbitol, stearyl dimethicone, stearyl methicone, triethoxycaprylylsilane, trimethylsiloxysilicate, xylitol, and zinc stearate. In some embodiments, sunscreen actives may include, but are not limited to, avobenzone, benzephenone-3, benzophenones, bumetrizole, butyl methoxydibenzoylmethane, ecamsule, ensulizole, ethylhexyl methoxycinnamate, homosalate, menthyl anthranilate, meradmiate, Mexoryl SX, octinoxate, octisalate, octocrylene, octyl methoxycinnamate, octyl salicylate, oxybenzone, padimate O, para-aminobenzoic acid (PABA), Parsol 1789, terephthalylidine dicamphor sulfonic acid, Tinosorb M, Tinosorb S, and titanium dioxide. In some embodiments, emulsifiers, surfactants, and detergents may include, but are not limited to, ammonium laureth sulfate, ammonium lauryl sulfate, arachidyl glucoside, behenic acid, bis-PEG-18 methyl ether dimethyl silane, $C_{20-40}$ pareth-40, cocamidopropyl betaine, cocamidopropyl dimethylamine, cocamidopropyl hydroxysultaine, coco-glucoside, coconut oil, decyl glucoside, dicetyl phosphate, dihydrocholeth-30, disodium cocoamphodiacetate, disodium cocoyl glutamate, disodium lauraminopropionate, glyceryl behanate, hydrogenated vegetable glycerides citrate, isohexadecane, isostearamide DEA, lauramphocarboxyglycinate, laureth-23, laureth-4, laureth-7, lauryl PEG-9 polydimethylsiloxyethyl dimethicone, lauryl alcohol, lauryl glucoside, magnesium laureth sulfate, magnesium oleth sulfate, myristic acid, nonoxynols, oleic acid, oleth 10, palm kernel acid, palmitic acid, PEG-60 almond glycerides, PEG-75 shea butter glycerides, PEG 90M, PEG-10 dimethicone, PEG-10 dimethicone/vinyl dimethicone crosspolymer, PEG-10 rapeseed sterol, PEG-100 stearate, PEG-12 dimethicone, PEG-120 methyl glucose dioleate, PEG-20 methyl glucose sesquistearate, PEG-40 stearate, PEG-60 hydrogenated castor oil, PEG-7 glyceryl cocoate, PEG-8, PEG-80 sorbitan laurate, PEG/PPG-17/6 copolymer (polyethylene glycol/polypropylene glycol-17/6 copolymer), PEG/PPG-18/18 dimethicone, PEG/PPG-20/15 dimethicone, poloxamer 184, Poloxamer 407, poloxamers, polyglyceryl-3 beeswax, polyglyceryl-4 isostearate, polyglyceryl-6 isostearate, polysorbate 20, polysorbate 60, polysorbate 80, potassium cetyl phosphate, potassium hydroxide, potassium myristate, PPG-12 buteth-16, PPG-26-Buteth-26, *Salvia officinalis, Saponaria officinalis* extract, soapwort, sodium $C_{14-16}$ olefin sulfonate, sodium cetearyl sulfate, sodium cocoamphoacetate, sodium cocoate, sodium cocoyl glutamate, sodium cocoyl isethionate, sodium dilauramidoglutamide lysine, sodium hexametaphosphate, sodium hydroxide, sodium laureth sulfate, sodium laureth-13 carboxylate, sodium lauroamphoacetate, sodium lauroyl lactylate, sodium lauroyl sarcosinate, sodium lauryl glucose carboxylate, sodium lauryl sulfate, sodium methyl cocoyl taurate, sodium methyl taurate, sodium myreth sulfate, sodium palm kernelate, sodium palmate, sodium PEG-7 olive oil carboxylate, sodium trideceth sulfate, steareth-20, TEA-lauryl sulfate (triethanolamine-lauryl sulfate), and tribehenin PEG-20 esters.

Application of the subject therapeutics may be local, so as to be administered at the site of interest (e.g., infected area of skin, or an infected joint or other connective tissue). Various techniques can be used for providing the subject compositions at the site of interest, such as injection, use of catheters, trocars, projectiles, pluronic gel, stents, sustained drug release polymers or other device which provides for internal access.

Thus, according to yet another embodiment, the compounds of the present application may be incorporated into compositions for coating an implantable medical device, such as prostheses, artificial valves, vascular grafts, stents, or catheters. Suitable coatings and the general preparation of coated implantable devices are known in the art and are exemplified in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition. Coatings for invasive devices are to be included within the definition of pharmaceutically acceptable carrier, adjuvant or vehicle, as those terms are used herein.

According to another embodiment, the present application provides a method of coating an implantable medical device comprising the step of contacting said device with the coating composition described above. It will be obvious to those skilled in the art that the coating of the device will occur prior to implantation into a mammal.

According to another embodiment, the present application provides a method of impregnating an implantable drug release device comprising the step of contacting said drug release device with a compound or composition of the present application. Implantable drug release devices include, but are not limited to, biodegradable polymer capsules or bullets, non-degradable, diffusible polymer capsules and biodegradable polymer wafers.

According to another embodiment, the present application provides an implantable medical device coated with a compound or a composition comprising a compound of the present application, such that said compound is therapeutically active.

Where an organ or tissue is accessible because of removal from the subject, such organ or tissue may be bathed in a medium containing a composition of the present application, a composition of the present application may be painted onto the organ, or a composition of the present application may be applied in any other convenient way.

In the pharmaceutical compositions of the present application, a compound of any one of Formulae I, II, III, and IV, or a pharmaceutically available salt thereof, is present in an effective amount (e.g., a therapeutically effective amount).

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y, 1970, 537.

In some embodiments, an effective amount of a compound of any one of Formulae I, II, III, and IV, or a pharmaceutically acceptable salt thereof, can range, for example, from about 1 mg to about 200 mg, from about 1 to about 100 mg, from about 1 to about 50 mg, from about 1 mg to about 30 mg, from about 1 mg to about 15 mg, from about 10 mg to about 2000 mg, from about 10 mg to about 1900 mg, from about 10 mg to about 1800 mg, from about 10 mg to about 1700 mg, from about 10 mg to about 1600 mg, from about 10 mg to about 1500 mg, from about 10 mg to about 1400 mg, from about 10 mg to about 1300 mg, from about 10 mg to about 1200 mg, from about 10 mg to about 1100 mg, from about 10 mg to about 1000 mg, from 10 mg about to about 900 mg, from about 10 mg to about 800 mg, from about 10 mg to about 700 mg, from about 10 mg to about 600 mg, from about 10 mg to about 500 mg, from about 10 mg to about 400 mg, from about 10 mg to about 300 mg, from about 10 mg to about 200 mg, from about 10 mg to about 100 mg, and from about 10 mg to about 50 mg. In some embodiments, an effective amount of a compound of any one of Formulae I, II, III, and IV, or a pharmaceutically acceptable salt thereof, is 1 mg, 2 mg, 3 mg, 4 mg, 5 mg, 6 mg, 7 mg, 8 mg, 9 mg, or 10 mg. In some aspects of these embodiments, the composition containing an effective amount of a compound of any one of Formulae I, II, III, and IV, or a pharmaceutically acceptable salt thereof, is administered once daily. In some aspects of these embodiments, the composition containing an effective amount of a compound of any one of Formulae I, II, III, and IV, or a pharmaceutically acceptable salt thereof, is administered twice daily. In some aspects of these embodiments, the composition containing an effective amount of a compound of any one of Formulae I, II, III, and IV, or a pharmaceutically acceptable salt thereof, is administered thrice daily.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

Combination Therapies

In some embodiments, a composition of the present application further comprises one or more additional therapeutic agents. The additional therapeutic agent may be selected from any compound or therapeutic agent known to have or that demonstrates advantageous properties when administered with a compound of any one of Formulae I, II, III, or IV.

In some embodiments, a pharmaceutical composition comprising a compound of Formulae I, II, III, and IV, or a pharmaceutically acceptable salt thereof, also optionally contains at least one additional therapeutic agent, or a pharmaceutically acceptable salt thereof. In these embodiments, the additional therapeutic agent in the composition is any one of the antibiotics described herein (e.g., gentamicin or defensin 1). The second therapeutic agent may be present in the composition in a therapeutically effective amount. For pharmaceutical compositions that comprise an additional therapeutic agent, or for methods that comprise using an additional therapeutic agent, an effective amount of the additional therapeutic agent is between about 20% and 100% of the dosage normally utilized in a monotherapy regime using just that agent. Preferably, an effective amount is between about 70% and 100% of the normal monotherapeutic dose. The normal monotherapeutic dosages of these additional therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are incorporated herein by reference in their entirety. In some embodiments, when the additional therapeutic agent is gentamicin, the effective amount of gentamicin is lower than the amount that causes nephrotoxicity in a subject.

In some embodiments, the pharmaceutical composition comprises:

(i) a compound of formula:

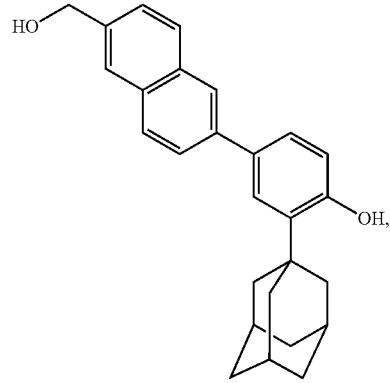 [SMILES: OCc1ccc2cc(-c3ccc(O)c(C45CC6CC(CC(C6)C4)C5)c3)ccc2c1]

or a pharmaceutically acceptable salt thereof (e.g., in a therapeutically effective amount);

(ii) antibiotic (e.g., gentamicin), or a pharmaceutically acceptable salt thereof (e.g., in a therapeutically effective amount); and (iii) a pharmaceutically acceptable carrier. In some aspects of these embodiments, the pharmaceutical composition is suitable for parenteral administration (e.g., a lyophilized powder or a sterile injection solution). In other aspects of these embodiments, the pharmaceutical composition is suitable for topical application (e.g., an aerosol spray, a cream, an emulsion, a foam, an oil, a gel, a lotion, a mousse, an ointment, or a patch).

In some embodiments, a method of treating a subject in need thereof as disclosed herein comprises administering to the subject one or more additional therapeutic agents. The additional therapeutic agent may be administered to the subject in a separate pharmaceutical composition or dosage form (e.g., any one of the compositions, formulation, routes and dosage forms described herein). In these embodiments, a compound of any one of Formula I, II, III and IV, or a pharmaceutically acceptable salt thereof, can be used in combination with an antibiotic.

In some embodiments, a compound of any one of Formula I, II, III and IV, or a pharmaceutically acceptable salt thereof, can be used in combination with a cationic antimicrobial peptide (CAMP). In some aspects of these embodiments, the cationic antimicrobial peptide is a defensin peptide (e.g., defensin 1 such as beta-defensin 1 or alpha-defensin 1), or cecropin, andropin, moricin, ceratotoxin, melittin, magainin, dermaseptin, bombinin, brevinin (e.g., brevinin-1), esculentin, buforin II (e.g., from amphibians), CAP18 (e.g., from rabbits), LL37 (e.g., from humans), abaecin, apidaecins (e.g., from honeybees), prophenin (e.g., from pigs), indolicidin (e.g., from cattle), brevinins, protegrin (e.g., from pig), tachyplesins (e.g., from horseshoe crabs), or drosomycin (e.g., from fruit flies).

In some embodiments, the antibiotic is selected from the quinolone class of antibiotic compounds. In some aspects of these embodiments, the antibiotic is selected from the group consisting of levofloxacin, norfloxacin, ofloxacin, ciprofloxacin, perfloxacin, lomefloxacin, fleroxacin, sparfloxacin, grepafloxacin, trovafloxacin, clinafloxacin, gemifloxacin, enoxacin, sitafloxacin, nadifloxacin, tosulfloxacin, cinnoxacin, rosoxacin, miloxacin, moxifloxacin, gatifloxacin, cinnoxacin, enoxacin, fleroxacin, lomafloxacin, lomefloxacin, miloxacin, nalidixic acid, nadifloxacin, oxolinic acid, pefloxacin, pirimidic acid, pipemidic acid, rosoxacin, rufloxacin, temafloxacin, tosufloxacin, trovafloxacin, and besifloxacin.

In some embodiments, the antibiotic is selected from a β-lactam, a monobactam, oxazolidinone, and lipopeptide.

In some embodiments, the antibiotic is selected from the cephalosporin class of antibiotic compounds. In some aspects of these embodiments, the antibiotic is selected from the group consisting of cefazolin, cefuroxime, ceftazidime, cephalexin, cephaloridine, cefamandole, cefsulodin, cefonicid, cefoperazine, cefoprozil, and ceftriaxone.

In some embodiments, the antibiotic is selected from the penicillin class of antibiotic compounds. In some aspects of these embodiments, the antibiotic is selected from the group consisting of penicillin G, penicillin V, procaine penicillin, and benzathine penicillin, ampicillin, and amoxicillin, benzylpenicillin, phenoxymethylpenicillin, oxacillin, methicillin, dicloxacillin, flucloxacillin, temocillin, azlocillin, carbenicillin, ricarcillin, mezlocillin, piperacillin, apalcillin, hetacillin, bacampicillin, sulbenicillin, mecicilam, pevmecillinam, ciclacillin, talapicillin, aspoxicillin, cloxacillin, nafcillin, and pivampicillin.

In some embodiments, the antibiotic is selected from the carbapenem class of antibiotic compounds. In some aspects of these embodiments, the antibiotic is selected from the group consisting of thienamycin, tomopenem, lenapenem, tebipenem, razupenem, imipenem, meropenem, ertapenem, doripenem, panipenem (betamipron), and biapenem.

In some embodiments, the antibiotic is selected from the lipopeptide class of antibiotic compounds. In some aspects of these embodiments, the antibiotic is selected from the group consisting of polymyxin B, colistin (polymyxin E), and daptomycin.

In some embodiments, the antibiotic is selected from the aminoglycoside class of antibiotic compounds. In some aspects of these embodiments, the antibiotic is selected from the group consisting of gentamicin, amikacin, tobramycin, debekacin, kanamycin, neomycin, netilmicin, paromomycin, sisomycin, spectinomycin, and streptomycin.

In some embodiments, the antibiotic is selected from the glycopeptide class of antibiotic compounds. In some aspects of these embodiments, the antibiotic is selected from the group consisting of vancomycin, teicoplanin, telavancin, ramoplanin, daptomycin, decaplanin, and bleomycin.

In some embodiments, the antibiotic is selected from the macrolide class of antibiotic compounds. In some aspects of these embodiments, the antibiotic is selected from the group consisting of azithromycin, clarithromycin, erythromycin, fidaxomicin, telithromycin, carbomycin A, josamycin, kitasamycin, midecamycin/midecamycinacetate, oleandomycin, solithromycin, spiramycin, troleandomycin, tylosin/tylocine, roxithromycin, dirithromycin, troleandomycin, spectinomycin, methymycin, neomethymycin, erythronolid, megalomycin, picromycin, narbomycin, oleandomycin, triacetyl-oleandomycin, laukamycin, kujimycin A, albocyclin and cineromycin B.

In some embodiments, the antibiotic is selected from the ansamycin class of antibiotic compounds. In some aspects of these embodiments, the antibiotic is selected from the group consisting of streptovaricin, geldanamycin, herbimycin, rifamycin, rifampin, rifabutin, rifapentine and rifamixin.

In some embodiments, the antibiotic is selected from the sulfonamide class of antibiotic compounds. In some aspects of these embodiments, the antibiotic is selected from the group consisting of sulfanilamide, sulfacetarnide, sulfapyridine, sulfathiazole, sulfadiazine, sulfamerazine, sulfadimidine, sulfasomidine, sulfasalazine, mafenide, sulfamethoxazole, sulfamethoxypyridazine, sulfadimethoxine, sulfasymazine, sulfadoxine, sulfametopyrazine, sulfaguanidine, succinylsulfathiazole and phthalylsulfathiazole.

In some embodiments, the antibiotic is selected from the group consisting of quinolones, fluoroquinolones, β-lactams, cephalosporins, penicillins, carbapenems, lipopeptide antibiotics, glycopeptides, macrolides, ansamycins, sulfonamides, and combinations of two or more thereof.

In some embodiments, the present application provides separate dosage forms of a compound of any one of Formulae I, II, III, and IV, or a pharmaceutically acceptable salt thereof, and one or more of any of the above-described second therapeutic agents. The separate dosage forms may be administered together consecutively (e.g., within less than 24 hours of one another) or simultaneously (e.g., administered to the patient within 5 minutes of one another).

Some of the second therapeutic agents referenced above will act synergistically with the compounds of the present application. In some embodiments, some of the second therapeutic agents referenced above will show additive effect. When this occurs, it will allow the effective dosage of the second therapeutic agent and/or the compound of the present application to be reduced from that required in a monotherapy. This has the advantage of minimizing toxic side effects of either the second therapeutic agent of a compound of the present application, synergistic improvements in efficacy, improved ease of administration or use and/or reduced overall expense of compound preparation or formulation.

Definitions

At various places in the present specification, substituents of compounds of the present application are disclosed in groups or in ranges. It is specifically intended that various embodiments of the present application include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "alkylene" means a bivalent branched, or straight chain chemical group containing only carbon and hydrogen, such as methylene, ethylene, n-propylene, iso-propylene, n-butylene, iso-butylene, sec-butylene, tert-butylene, n-pentylene, iso-pentylene, sec-pentylene and neo-pentylene. Alkylene groups can either be unsubstituted or substituted with one or more substituents. Alkylene groups can be saturated or unsaturated (e.g., containing —C=C— or —C≡C— subunits), at one or several positions. In some embodiments, alkylene groups include 1 to 9 carbon atoms (for example, 1 to 6 carbon atoms, 1 to 4 carbon atoms, or 1 to 2 carbon atoms).

As used herein, the term "$C_{n-m}$ alkoxy", employed alone or in combination with other terms, refers to a group of formula —O-alkyl, wherein the alkyl group has n to m carbons. Example alkoxy groups include, but are not limited to, methoxy, ethoxy, propoxy (e.g., n-propoxy and iso-propoxy), butoxy (e.g., n-butoxy and tert-butoxy), and the like. In some embodiments, the alkyl group has 1 to 6, 1 to 4, or 1 to 3 carbon atoms.

As used herein, "halo" or "halogen" refers to F, Cl, Br, or I. In some embodiments, a halo is F, Cl, or Br. In other embodiments, halo is F, Cl, or I. In other embodiments, halo is F, I, or Br.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms. Examples of alkylamino groups include, but are not limited to, N-methylamino, N-ethylamino, N-propylamino (e.g., N-(n-propyl) amino and N-isopropylamino), N-butylamino (e.g., N-(n-butyl)amino and N-(tert-butyl)amino), and the like.

As used herein, the term "di $C_{n-m}$ alkylamino" refers to a group of formula —N(alkyl)$_2$, wherein each alkyl group independently has n to m carbon atoms. In some embodiments, each alkyl group has 1 to 6, 1 to 4, or 1 to 3 carbon atoms. Examples of dialkylamino groups include, but are not limited to, N,N-methylehtylamino, N,N-diethylamino, N,N-propylethylamino, N,N-butylisopropylamino, and the like.

As used herein, the term "HO—$C_{1-3}$ alkylene" refers to a group of formula —($C_{1-3}$ alkylene)-OH.

As used herein, the term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

As used herein, the term "tautomer" refers to compounds which are capable of existing in a state of equilibrium between two isomeric forms. Such compounds may differ in the bond connecting two atoms or groups and the position of these atoms or groups in the compound.

As used herein, the term "isomer" refers to structural, geometric and stereo isomers. As the compound of the present application may have one or more chiral centers, it is capable of existing in enantiomeric forms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "individual", "patient", or "subject" used interchangeably, refers to any animal, including mammals, preferably mice, rats, other rodents, rabbits, dogs, cats, swine, cattle, sheep, horses, or primates, and most preferably humans.

As used herein, the phrase "effective amount" or "therapeutically effective amount" refers to the amount of active compound or pharmaceutical agent that elicits the biological or medicinal response in a tissue, system, animal, individual or human that is being sought by a researcher, veterinarian, medical doctor or other clinician.

As used herein the term "treating" or "treatment" refers to 1) inhibiting the disease; for example, inhibiting a disease, condition or disorder in an individual who is experiencing or displaying the pathology or symptomatology of the disease, condition or disorder (i.e., arresting further development of the pathology and/or symptomatology), or 2) ameliorating the disease; for example, ameliorating a disease, condition or disorder in an individual who is experiencing or displaying the pathology or symptomatology of the disease, condition or disorder (i.e., reversing the pathology and/or symptomatology).

As used herein, the terms "resistant" and "persistent" (or "persister") refer to bacterial strains that exhibit a high level of tolerance to one or more antibiotics. In some embodiments, the bacterial strain is resistant when the MIC of the bacterial strain is at least 2× (2-fold) of the MIC for the non-resistant strain. The x-fold resistant bacterial strain may be determined by the following steps: (i) MIC is determined for a non-resistant bacterial strain; (ii) the non-resistant bacterial strain is treated in a multi-well plate with an antibiotic at 2×, 5×, 10× etc, of the minimal inhibitory concentration (MIC); (iii) bacterial culture treated with the highest concentration that permitted bacterial growth is taken for serial passage for 100 days; and (iv) MIC of the bacterial culture after 100 days of serial passage is determined. If MIC of the bacterial culture after 100 days of serial passage is at least 2× of the MIC of the non-resistant strain, then the bacterial culture is at least 2× resistant to the antibiotic.

As used herein, the term "pharmaceutical carrier", or "pharmaceutically acceptable carrier" refers to a pharmaceutically acceptable solvent, suspending agent or vehicle for delivering the compound of the present application to the subject. The carrier may be liquid or solid and is selected with the planned manner of administration in mind. Each carrier must be pharmaceutically "acceptable" in the sense of being compatible with other ingredients of the composition and non-injurious to the subject.

As used herein, "topical use", "topical route" and "topically applying" means directly laying on or spreading on the skin, hair, mucous membrane (e.g., oral or vaginal mucous membrane), or nail, e.g., by use of the hands or an applicator such as a wipe or a patch.

The term "topical composition" as used herein refers to any composition suitable for the topical application to mammalian keratinous tissue such as in particular to human skin. In particular, the topical compositions according to the present disclosure are cosmetic compositions that can be topically applied to mammalian keratinous tissue, particularly to human skin.

EXAMPLES

General Methods.

Bacterial Strains, Growth Conditions and Persister Isolation.

Methicillin-resistant *S. aureus* (MRSA) strain MW2 BAA-1707, the VanA-type vancomycin-resistant *S. aureus* strain VRS 1, 11 clinical *S. aureus* isolates 8 clinical *Enterococcus faecium* isolates (including VanB-type VRE isolates, C68 and WB312, and a VanA-type VRE isolate WC 196), *Klebsiella pneumoniae* WGLW2 (BEI Resources, Manassas, Va., USA), *Acinetobacter baumannii* ATCC 17978, *Pseudomonas aeruginosa* PA14, and *Enterobacter aerogenes* ATCC 13048 were used to test antimicrobial activity. *S. aureus* and *E. faecium* strains were grown in tryptic soy broth (TSB) (BD, Franklin Lakes, N.J., USA) or brain-heart infusion (BHI) broth (BD, Franklin Lakes, N.J., USA), respectively at 37° C. *K. pneumoniae, A. baumannii, P aeruginosa*, and *E. aerogenes* were grown in Luria Bertani (LB) broth (BD, Franklin Lakes, N.J., USA).

Antimicrobial Agents and Chemicals.

Vancomycin, oxacillin, gentamicin, ciprofloxacin, rifampicin, tetracycline, and adapalene were purchased from Sigma-Aldrich (St Louis, Mo., USA). CD437, CD1530, linezolid, and daptomycin were purchased from R&D Systems (Minneapolis, Minn., USA), and adarotene was purchased from MedChem Express (Monmouth Junction, N.J., USA). 10 mg/ml stocks of all compounds were made in DMSO or ddH$_2$O. For assays with daptomycin, media or buffer were supplemented with 50 µg/ml CaCl$_2$.

Minimal Inhibitory Concentration (MIC) Assay.

The MICs of antibiotics were determined by the standard micro-dilution method recommended by the Clinical and Laboratory Standards Institute. The assay was conducted in triplicate.

Killing Kinetics Assay.

An overnight culture of *S. aureus* MW2 was diluted 1:10,000 in 25 ml fresh TSB in a 250 ml flask. In order to obtain exponential-phase cells, the diluted cell suspension was incubated at 37° C., with shaking at 225 rpm for 4 h until the OD$_{600\ nm}$ was 0.4 (~2×10$^7$ CFU/ml). 1 ml of the exponential phase cell culture was added to the wells of a 96-well assay block (Corning Costar 3960, Corning, N.Y., USA) containing 1 ml of pre-warmed TSB with twice the desired concentrations of compounds. The assay block was sealed with a gas-permeable Breathe-Easy membrane and incubated at 37° C. shaking at 225 rpm. At specific times, 400 µl samples were removed and washed once with PBS to remove the antibiotic. The samples were serially diluted 10$^5$ fold with PBS and spot-plated onto TSA plates. After incubating the plates overnight (~18 h) at 37° C., the colonies were counted to enumerate the number of cells. These experiments were conducted in triplicate. To determine bacterial lysis, 5 ml of exponential-phase MW2 culture (OD$_{600\ nm}$ ~0.4) was treated with 10×MIC of CD437, CD1530, or benzalkonium chloride (BAC) for 4 h. Anti-infective detergent BAC was used as a positive control to cause bacterial lysis. Every hour, 1 ml of each sample was added to an optical cuvette with a 1 cm path length. OD$_{600\ nm}$ was measured using an Eppendorf BioPhotometer plus (Eppendorf, Hamburg, Germany). The experiments were conducted in triplicate.

Persister Killing Assay.

As has been previously demonstrated, stationary-phase cells of *S. aureus* can be used to model persister cells, and we have shown previously that MW2 and the 11 clinical *S. aureus* isolates (BF 1-BF 11) become persisters that when grown to stationary phase are tolerant to conventional antibiotics such as gentamicin, ciprofloxacin and vancomycin. Persistency of stationary-phase *S. aureus* VRS 1 was evaluated by treating with 100×MIC daptomycin and 100×MIC linezolid, because the strain is resistant to vancomycin, gentamicin, ciprofloxacin, and rifampicin. We prepared persister cells of the 13 *S. aureus* strains by growing cultures overnight to stationary phase at 37° C. at 225 rpm. The overnight cultures were washed three times with PBS and diluted to ~5×10$^7$ pCFU/ml with the same buffer. 2 ml of the persister suspension containing appropriate concentrations of antibiotics was added to the wells of a 96-well assay block (Corning Costar 3960) and incubated at 37° C., with shaking at 225 rpm. At specific times, 400 µl samples were removed and washed once with PBS to remove the antibiotic. The samples were serially diluted 10$^5$ fold with PBS and spot-plated onto TSA plates. After incubating the plates overnight (~18 h) at 37° C., the colonies were counted to enumerate the number of cells. These experiments were conducted in triplicate.

Biofilm Persister Killing Assay.

An overnight culture of *S. aureus* MW2 was diluted 1:200 with TSB supplemented with 0.2% glucose and 3% NaCl[23]. A 13 mm diameter Millipore mixed cellulose ester membrane (GSWP01300, EMD Millipore, Billerica, Mass., USA) was placed at the bottom of each well of a 12-well plate (Falcon 353043, Corning, N.Y., USA). 1 mL of the diluted culture was added to each well and incubated statically at 37° C. for 24 h. The membranes were washed 3-times with PBS and transferred to a fresh 12-well plate. 1 mL of PBS containing the desired concentration of antibiotics or the synthetic retinoids was added to each well, and then the plate was incubated statically at 37° C. for 24 h. The membranes were washed 3 times with PBS, placed in 2-ml microcentrifuge tubes containing 1 mL PBS, and sonicated in an ultrasonic bath (Fisher Scientific FS 30) for 10 min. The sonicated samples were serially diluted and spot-plated on TSA plates. After incubating the plates overnight (~18 h) at 37° C., the colonies were counted to enumerate the number of cells. The experiment was conducted in triplicate.

SYTOX Green Membrane Permeability Assay.

Black, clear-bottom, 96-well plates (Corning no. 3904, Corning, N.Y., USA) were filled with 50 µl of phosphate buffered saline (PBS)/well containing the indicated concentration of antibiotics. Exponential-phase *S. aureus* MW2 cells prepared as described in the Killing kinetics assay were washed 3 times with the same volume of PBS. The washed cells were adjusted to $OD_{600}$=0.4 (~2×10$^7$ CFU/ml) with PBS. For persister membrane permeability study, overnight stationary-phase *S. aureus* MW2 cells were washed 3 times with PBS and then adjusted to ~10$^8$ CFU/ml. SYTOX Green (Molecular Probes, Waltham, Mass., USA) was added to 10 ml of the diluted bacterial suspension to a final concentration of 5 µM and incubated for 30 min at room temperature in the dark. 50 µl of the bacteria/SYTOX Green mixture was added to each well of the 96-well plates containing antibiotics and fluorescence was measured at room temperature using a spectrophotometer (SpectraMax M2, Molecular Devices, Sunnyvale, Calif., USA), with excitation and emission wavelengths of 485 nm and 525 nm, respectively. All experiments were conducted in duplicate or triplicate.

Transmission Electron Microscopy.

*S. aureus* MW2 was grown to the exponential phase ($OD_{600}$=~0.4) at 37° C. Bacterial cultures were then treated with 10×MIC of CD437, CD1530 or 0.1% DMSO (control) at 37° C. for 30 minutes. 1 ml of the retinoid treated cells was fixed with the same volume of a 2× fixative, a mixture of 5% glutaraldehyde, 2.5% paraformaldehyde and 0.06% picric acid in 0.2 M sodium cacodylate buffer (pH 7.4). After spinning down, a pellet of cells were incubated for at least 2 h at room temperature and then stored at 4° C. Fixed cells were washed in 0.1 M cacodylate buffer and post-fixed with 1% Osmium tetroxide ($OsO_4$)/1.5% Potassium ferrocyanide ($KFeCN_6$) for 1 h, washed twice in water, once in maleate buffer (MB), and incubated in 1% uranyl acetate in MB for 1 h. Cells were then washed twice in water and subsequently dehydrated in an alcohol gradient series (10 min each; 50%, 70%, 90%, 2×10 min 100%). The cells were then put in propyleneoxide for 1 h and infiltrated overnight in a 1:1 mixture of propyleneoxide and Spurr's low viscosity resin (Electron Microscopy sciences, Hatfield, Pa.). The cells were embedded in Spurr's resin and polymerized at 60° C. for 48 h. Ultrathin sections (about 60 nm) were cut on a Reichert Ultracut-S microtome (Leica Microsystem, Wetzlar, Germany), picked up onto copper grids, and stained with lead citrate. Micrographs of the cells were taken using a JEOL 1200EX transmission electron microscope (Harvard Medical School EM facility).

Preparation of Giant Unilamellar Vesicles (GUVs) and Observation of Effects of Compounds on GUVs.

GUVs were prepared by the electroformation method described previously. Dioleoyl-glycero-phosphocholine (DOPC), Dioleoyl-glycero-phosphoglycerol (DOPG) and Dioleoyl-glycero-phosphoethanolamine-N-lissamine rhodamine B sulfonyl (18:1 Liss Rhod PE) were purchased from Avanti Polar Lipids (Alabaster, Ala., USA). 4 mM of a lipid mixture consisting of DOPC/DOPG/18:1 Liss Rhod PE (7:3:0.005) was dissolved in chloroform, and 40 µl of this mixture was then spread onto indium tin oxide (ITO)-coated slides (50×75×1.1 mm, Delta Technologies, Loveland, Colo., USA). In order to remove chloroform, the ITO slides were dried in a vacuum chamber for 2 h. To make an elecroformation chamber, a 2 mm thick Teflon spacer was inserted between the lipid-applied surfaces of two ITO slides. 2 ml of 100 mM sucrose was added into the electroformation chamber, followed by sealing with binder clips. The swelling of the lipid bilayers was facilitated by applying an electric AC-field (10 Hz). The field strength was gradually increased from 0 to 0.5 kV/m for 30 min, and then was maintained constantly for 30 min. GUVs were detached from surfaces by reducing the AC-field from 10 Hz to 5 Hz for 20 min. The GUV suspension was diluted (1:30) in a 100 mM glucose solution. 49 µl of the diluted GUV suspension (~100 vesicles) was transferred to a black, clear-bottom 384-well plate (Corning no. 3712, Corning, N.Y., USA). The plate was left in the dark at room temperature for 30 min until all GUVs settled on the bottom of the plates. After adding 1 µl of compound solution to a well (final compound concentration: 10×MIC or 1×MIC), the GUVs were observed and imaged with an optical microscope equipped with a fluorescence contrast and a digital camera (40× or 63× objectives, Axio Observer. Al & AxioCam MRm, Zeiss, Germany). Images and videos are representative of three independent experiments.

All-Atom Molecular Dynamics (MD) Simulations.

All-atom MD simulations based on the GROMACS package (version 4.6.7) were performed to investigate the interactions between selected retinoids (CD437, CD1530, adarotene, adapalene, other analogs, and glucuronided metabolites) and a simulated plasma membrane of *S. aureus*. The Gromos54a7 force field with Automated Topology Builder was employed for the partial atomic charges and the non-bonded and bonded parameters of the retinoid molecules in the simulations. Two membrane models of different lipid compositions were adopted to represent the plasma membrane of *S. aureus*. One was a mixed lipid bilayer composed of 88 neutral-charged DOPC and 40 negatively-charged DOPG lipids (~7:3 ratio) with dimensions of 5.96 nm×5.96 nm. This mixture of lipids is widely used to mimic anionic bacterial membranes and to investigate the mechanisms of action of membrane-active antimicrobials, such as daptomycin and antimicrobial peptides on *S. aureus* membranes. Lipid bilayers at different lipid ratios of 6:4 (80 DOPC and 48 DOPG lipids) and 5:5 (64 DOPC and 64 DOPG lipids) were also constructed to study the effects of membrane surface charges on the antimicrobial activity of retinoids. The DOPC and DOPG lipids were modeled with Berger's lipid force field, which is an extensively validated all-atom lipid model for membrane-related simulations. The other membrane model was a mixed lipid bilayer composed of 108 PG lipids, 72 Lys-PG lipids, and 10 DPG (Cardiolipin) lipids with dimensions of 8.50 nm×7.36 nm, which was used previously to more specifically mimic *S. aureus* membranes. Repetitions of simulations with these two different membrane compositions were performed to verify the robustness of results and mechanisms. Sodium ions were added into the simulation system to neutralize the negative charge of membranes. For enhanced computational efficiency, water molecules were represented by a polarization corrected simple point-charge SPC/E model. A geometric combining rule of Lennard-Jones potential was adopted for non-bonded interactions of retinoid molecules with lipids, ions and water. The fast smooth particle-mesh Ewald was used to calculate the long-rang electrostatic interactions. The system was modeled as an NPT ensemble, with periodic boundary conditions in all directions, under constant pressure P (1 atm) and constant temperature T (300 K). The simulation box had an initial height of 12.3 nm, which was large enough to prevent the membrane and retinoid molecules from interacting with their periodic images. The time step was fixed at 2 fs. After a 500 ns initial equilibration of solvated lipid systems, the retinoid molecules were introduced into the water phase above the membrane. After 100 ns of re-equilibration, the retinoid molecules were released and their interactions with the membrane including attachment, penetration and equilibrium configurations were further simulated for 500-1000 ns. The free energy profiles for the translocations of retinoid molecules were calculated by steered molecular dynamics, umbrella sampling, and weighted histogram analysis method, with the output giving the transfer energies and energy barriers that describe the feasibility (favorability and rate, respectively) of membrane penetration. The energy profile of penetration is a theoretical representation of an energetic pathway, as the retinoids are translocated into membrane, with two independent parameters: transfer energy and energy barrier. The transfer energy of penetration, which is defined as the energy conversion of two equilibrium states from outside to inside the membrane, describes the direction of translocation. The negative value of transfer energy that represents the energy decrease for penetration indicates that the embedment of retinoids inside the membrane is energetically favorable. The energy barrier is calculated as the height of the peak along the pathway relative to the equilibrium state outside the membrane. The energy barrier is the least energy the retinoids must possess to cross over the membrane surface which governs the rate of penetration. A lower energy barrier corresponds to a faster and easier penetration. The thermal energy $k_BT$ was used as the unit of energy in the simulations with the T corresponding to the room temperature (300 K). In equilibrium, the probability of a system being in the state with energy E is proportional to $e^{-E/k_BT}$. By using the $k_BT$ as the measurement, the system stability could be explicitly compared at different equilibrium states. To visualize the membrane attachment and penetration, the retinoids and sodium ions are depicted as large spheres, and phospholipids are represented as chains. The atoms in retinoids, phospholipids and sodium ions are colored as follows: hydrogen, white; oxygen, red; nitrogen, dark blue; carbon, cyan; phosphorus, orange; sodium, lavender. Water molecules are set to be transparent for clarity. The outer blue lines in the MD videos indicate the period boundaries of the simulation boxes.

Human Blood Hemolysis.

Hemolytic activity of retinoids on human erythrocytes was evaluated using a previously described method with modifications. 10% human erythrocytes were purchased from Rockland Immunochemicals (Limerick, Pa., USA). The erythrocytes were diluted to 4% with PBS, and 100 μl was added to 100 μl of two-fold serial dilutions of compounds in PBS, 0.2% DMSO (negative control), or 2% Triton-X 100 (positive control) in a 96-well plate. The plate was incubated at 37° C. for 1 h and then centrifuged at 500×g for 5 min. 100 μl of the supernatant was transferred to a fresh 96-well plate and absorbance of supernatants was measured at 540 nm. Percent hemolysis was calculated using the following equation: ($A_{540nm}$ of compound treated sample−$A_{540nm}$ of 0.1% DMSO treated sample)/($A_{540nm}$ of 1% Triton X-100 treated sample−$A_{540nm}$ of 0.1% DMSO treated sample)×100. $HC_{50}$ (concentration of compound causing 50% hemolysis) was determined using SigmaPlot 10.0 (Systat Software Inc., San Jose, Calif., USA).

Cytotoxicity.

Cryopreserved rat and human primary hepatocytes were purchased from the Cell Resource Core at Massachusetts General Hospital (Boston, Mass., USA). The hepatocytes were cultured in a collagen sandwiched configuration in 24-well plates, as described previously. Briefly, 4×10⁵ live cells were seeded in 24-well plates coated with rat tail collagen type I. Plates were incubated in a humidified 5% $CO_2$ incubator at 37° C. for 4 h to allow cells to attach to the collagen gel. The cells were washed and then cultured in 0.5 ml standard hepatocyte culture medium consisting of pre-warmed Dulbecco's modified Eagle's medium (DMEM) media supplemented with 10% FBS, 0.5 U/ml insulin, 14 ng/ml glucagon, 20 ng/ml EGF, 7.5 μg/ml hydrocortisone and 200 U/ml penicillin-streptomycin. The cell cultures were incubated in a humidified 5% $CO_2$ incubator at 37° C. At 24 h after seeding the cells, a top layer of collagen gel was deposited on the hepatocytes attached to the bottom collagen layer and incubated for additional 24 h.

Human hepatoma, HepG2 (ATCC HB-8065) cells were maintained in DMEM containing 10% fetal bovine serum and antibiotics penicillin-streptomycin (100 units/ml). Normal human primary renal proximal tubular epithelial cells (RPTEC, Lonza catalog # CC-2553, Walkersville, Md., USA) and adult normal human epidermal keratinocytes (NHEK, Lonza catalog #192627) were maintained in renal cell growth media with growth supplements (REGM, Lonza catalog # CC-3190) and in keratinocyte growth media 2 with growth supplements (KGM-2, Lonza catalog # CC-3107), respectively in a humidified 5% $CO_2$ incubator at 37° C.

For cytotoxicity tests, HepG2, RPTEC, and NHEK were cultured at 70-80% confluence in tissue culture treated 96-well plates in a volume of 100 l/well corresponding culture media. To test cytotoxicity in the absence of serum, all cells were washed twice with PBS and then once with the serum-free corresponding culture media. The cells were then treated with a range of concentrations of retinoids in the serum-free culture media for 24 h. For the last 4 h of the 24 h period, 50 μl and 10 μl of WST-1 (Roche, Mannheim, Germany) were added in each well of the 24-well and the 96-well plates, respectively. WST-1 reduction was measured at 450 nm. The percent fluorescence relative to that of the no-treatment control was calculated. The assay was done in triplicate.

Evaluation of Human Ether-a-go-go-Related Gene (hERG) Potassium Channel Inhibition Potential.

The inhibitory potential of CD437, CD1530, and adarotene on the cardiac voltage-gated potassium channel hERG was evaluated by Cyprotex (Watertown, Mass., USA). Electrophysiology measurements were conducted using an IonWorks™ HT instrument (Molecular Devices Corporation, Sunnyvale, Calif., USA) and 384-well planar PatChPlate™ (Molecular Devices Corporation). Briefly, Chinese hamster ovary (CHO) cells expressing the hERG potassium channel were dispensed into 384-well planar arrays, and hERG tail currents were measured by whole-cell voltage clamping. A range of concentrations (0.008 μM to 25 μM) of each retinoid were then added to the cells, and a second recording of the hERG current was made. The percent change in the hERG current was calculated. Quinidine, an established hERG inhibitor was used as a positive control, and 0.25% DMSO was used as a negative control.

Antibiotic Synergy Test.

The checkerboard method was used for determining synergy of the synthetic retinoids with conventional antibiotics. Briefly, 2-fold serial dilutions of each retinoid were combined with 2-fold serial dilutions of each conventional antibiotic, creating an 8×8 matrix in a 96-well microtiter plate. The fractional inhibitory concentration index (FICI) was calculated as follows: FICI=MIC of compound A in combination/MIC of compound A alone+MIC of compound B in combination/MIC of compound B alone. The interaction between two compounds was defined, as follows: synergy if FICI≤0.5, no interaction if 0.5<FICI≤4, antagonism if FICI>4.

Pharmacokinetic Analysis.

Pharmacokinetic experiments were conducted by SAI Life Sciences Ltd. (Pune, India) in accordance with guidelines provided by the Committee for the Purpose of Control and Supervision of Experiments on Animals (CPCSEA). The Institutional Animal Ethics Committee (IAEC) approved the experimental protocol. In brief, healthy female CD1 mice (6 weeks old) weighing between 20 to 25 g were procured from Hylasco (Hyderabad, India). Analog 2 was dissolved in a 1:1 solution of Kolliphor EL (Sigma-Aldrich, St Louis, Mo., USA) and ethanol and then diluted 1:10 in saline to a final concentration of 2 mg/ml. Groups of mice (n=3) were treated with 20 mg/kg Analog 2 (i.p.). Blood samples were collected as terminal a bleed under light isoflurane anesthesia through a cardiac puncture such that samples were obtained at pre-dose, 0.08, 0.25, 0.5, 1, 2, 4, 8 & 24 h. Immediately after collection, plasma was harvested by centrifugation and stored at −70° C. until analysis. All samples were processed for analysis by protein precipitation using acetonitrile and analyzed with fit-for-purpose LC/MS/MS method (LLOQ=4.90 ng/mL for plasma). Pharmacokinetic parameters were calculated using the non-compartmental analysis tool of Phoenix WinNonlin (Version 6.3). No statistical methods were used to predetermine samples size. The experiments were not randomized, and investigators were not blinded to allocation during experiments and outcome assessment. Outliers were determined based on Grubb's test using GraphPad Prism 7 (GraphPad Software, La Jolla, Calif., USA).

Maximum Tolerated Dose.

Six-week-old female CD1 ICR outbred mice (20-25 g) were obtained from Charles River Laboratories (Wilmington, Mass., USA). Analog 2 was dissolved in a 1:1 solution of Kolliphor EL (Sigma-Aldrich, St Louis, Mo., USA) and ethanol and then diluted 1:10 in saline to a final concentration of 4 mg/ml. Groups of mice (n=6) were treated with 10, 20, 40, 80 mg/kg Analog 2 i.p. or vancomycin (25 mg/kg) every 12 h for 3 days. Control mice were injected with 400 µl of 10% Kolliphor EL/ethanol in saline i.p. every 12 h for 3 days. Mice were closely monitored until they were euthanized at 72 h from the first infection. After euthanizing mice, blood was collected by cardiac puncture. All samples were stored at 4° C. until for analysis. Serum was analyzed for alanine aminotransferase and urea nitrogen content with commercially available kits, following the manufacturer's protocol (Pointe Scientific, Canton, Mich., USA). No statistical methods were used to predetermine samples size. The experiments were not randomized, and investigators were not blinded to allocation during experiments and outcome assessment. This study and all experimental protocols were approved by the Rhode Island Hospital Institutional Animal Care and Use Committee (RIH IACUC) and conducted in accordance with the Animal Welfare Act and National Institutes of Health guidelines for animal care and use. Statistical significance among each group was analyzed by one-way ANOVA with post-hoc Tukey test using PASW Statistics 18 (SPSS Inc. Chicago, Ill., USA) and GraphPad Prism 7 (GraphPad Software, La Jolla, Calif., USA).

Deep-Seated Mouse Thigh Infection Model for Evaluating Drug Efficacy.

A previously described protocol to mimic a chronic, deep-tissue infection was used with modifications. Six-week-old female CD1 ICR outbred mice (20-25 g) were obtained from Charles River Laboratories (Wilmington, Mass., USA). To make mice neutropenic, 150 mg/kg and 100 mg/kg of cyclophosphamide were administered via i.p. injection at 4 days and 1 day before infection, respectively. On the day of infection, ~$10^5$ cells of stationary-phase S. aureus MW2 suspended in 50 µl of saline were injected to the right thigh of each mouse. To test the efficacy of CD437, the compound was dissolved in a 1:1 solution of Kolliphor EL (Sigma-Aldrich, St Louis, Mo., USA) and ethanol and then diluted 1:10 in saline to a final concentration of 20 mg/kg. Because CD437 shows in vivo efficacy in the mouse xenograft cancer models at 10-30 mg/kg up to 3 weeks without showing detectable toxicity, we tested it at 20 mg/kg in the MRSA mouse deep-seated thigh infection model. At 24 h post-infection, groups of mice (n=10) were treated with 30 mg/kg gentamicin subcutaneously (s.c.), 25 mg/kg vancomycin i.p., 20 mg/kg CD437 i.p., or a combination of 20 mg/kg CD437 i.p. and 30 mg/kg gentamicin s.c. every 12 h for 3 days. Control mice were injected with 200 µl of 10% Kolliphor EL/ethanol in saline i.p. every 12 h for 3 days. For testing the efficacy of Analog 2, the compound was dissolved in a 1:1 solution of Kolliphor EL (Sigma-Aldrich, St Louis, Mo., USA) and ethanol and then diluted 1:10 in saline to a final concentration of 4 mg/ml. Groups of mice (n=10) were treated with 40 or 80 mg/kg Analog 2 i.p. or in combination with 30 mg/kg gentamicin s.c., or a combination of 25 mg/kg vancomycin i.p. and 30 mg/kg gentamicin s.c. every 12 h for 3 days. Control mice were injected with 400 µl of 10% Kolliphor EL/ethanol in saline i.p. every 12 h for 3 days. After euthanizing mice at 96 h post-infection, blood was collected by cardiac puncture and the infected thighs were aseptically excised. All samples were stored at 4° C. until use. Serum was analyzed for alanine aminotransferase and urea nitrogen content with commercially available kits, following the manufacturer's protocol (Pointe Scientific, Canton, Mich., USA). Thigh tissue was homogenized in PBS and the number of MRSA in homogenates was enumerated by serial dilution and spot-plating on TSA plates. The bacterial burden was recorded as CFU/g tissue. A sample size of 10 mice per group was calculated for a single-tailed power analysis using a standard deviation based on our historical data and the literature in consultation with the Rhode Island Hospital Biostatistics Core. The experiments were not randomized, and investigators were not blinded to allocation during experiments and outcome assessment. This study and all experimental protocols were approved by the Rhode Island Hospital Institutional Animal Care and Use Committee (RIH IACUC) and conducted in accordance with the Animal Welfare Act and National Institutes of Health guidelines for animal care and use. Statistical significance among each group was analyzed by one-way ANOVA with post-hoc Tukey test using PASW Statistics 18 (SPSS Inc. Chicago, Ill., USA) and GraphPad Prism 7 (GraphPad Software, La Jolla, Calif., USA).

Synthesis of CD437 Analogs.

NMR spectra were recorded using the following spectrometers: Bruker Avance 500 (500 MHz-$^1$H/125 MHz-$^{13}$C) or Bruker Avance 400 (400 MHz-$^1$H/100 MHz-$^{13}$C). Chemical shifts are quoted in ppm relative to tetramethylsilane and with the indicated solvent as an internal reference. The following abbreviations are used to describe signal multiplicities: s (singlet), d (doublet), t (triplet), q (quartet), m (multiplet), br (broad), dd (doublet of doublets), dt (doublet of triplets), etc. Accurate mass spectra were recorded on an Agilent 6520 Accurate-Mass Q-TOF LC/MS, infrared spectra were obtained using a Thermo Nicolet Nexus 670 FTIR spectrophotometer.

Non-aqueous reactions were performed under an atmosphere of argon, in flame-dried glassware, with HPLC-grade solvents purified on a Pure Process Technology solvent purification system. Brine refers to a saturated aqueous solution of sodium chloride, sat. NaHCO$_3$ refers to a saturated aqueous solution of sodium bicarbonate, sat. NH$_4$Cl refers to a saturated aqueous solution of ammonium chloride, etc "Column chromatography", unless otherwise indicated, refers to purification in a gradient of increasing EtOAc concentration in hexanes on a Biotage® flash chromatography purification system. All chemicals were used as received from Oakwood, TCI America, Sigma-Aldrich, Alfa Aesar, or AK Scientific.

Example 1—Synthesis of Compounds

Compounds 9-16 may synthesized, for example, as outline in FIG. 10.

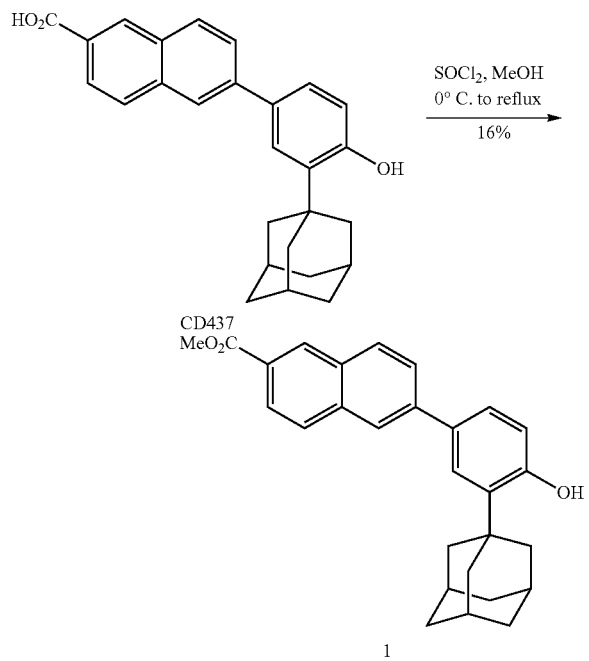

Methyl 6-(3-(adamantan-1-yl)-4-hydroxyphenyl)-2-naphthoate (1)

To a solution of CD437 (20 mg, 0.047 mmol) in MeOH (0.5 mL) was added SOCl$_2$ (0.01 mL, 0.12 mmol) at 0° C., the reaction was heated to reflux and stirred for 2 hours. The reaction was cooled to room temperature and concentrated. The yellow solid was purified by HPLC, yielding the title compound as a white solid (3.1 mg, 16% yield). $^1$H NMR (500 MHz, DMSO) δ 9.60 (s, 1H), 8.62 (s, 1H), 8.22-8.12 (m, 2H), 8.08 (d, J=8.8 Hz, 1H), 7.97 (dd, J=8.6, 1.7 Hz, 1H), 7.88 (dd, J=8.6, 1.8 Hz, 1H), 7.55-7.46 (m, 2H), 6.92 (d, J=8.2 Hz, 1H), 3.92 (s, 3H), 2.17 (s, 6H), 2.07 (s, 3H), 1.76 (s, 6H); $^{13}$C NMR (125 MHz, DMSO) δ 166.39, 156.55, 140.89, 136.09, 135.66, 130.68, 130.27, 129.91, 129.83, 128.50, 126.24, 126.06, 125.44, 125.26, 125.03, 123.65, 117.02, 52.19, 36.64, 36.37, 28.41; HRMS Accurate mass (ES+): Found 413.2115, C$_{28}$H$_{29}$O$_3$ (M+H+) requires 413.2117.

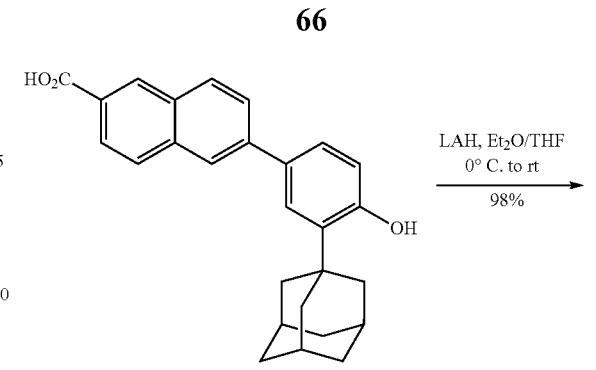

2-(adamantan-1-yl)-4-(6-(hydroxymethyl)naphthalen-2-yl)phenol (2)

Lithium aluminum hydride (LAH) (44 mg, 1.154 mmol) was added to a solution of CD437 (230 mg, 0.577 mmol) in 2:1 Et$_2$O:THF (15 mL) at 0° C. The reaction was warmed to room temperature and stirred for 2 hours. The reaction was cooled to 0° C. and H$_2$O (10 mL) was added slowly followed by 2M NaOH (10 mL). The resulting slurry was filtered over Celite and washed with EtOAc. The aqueous layer was extracted with EtOAc 3× and the combined organics were washed with water and brine, dried over Na$_2$SO$_4$, filtered, and concentrated; yielding the title compound as a white solid (217 mg, 98% yield). $^1$H NMR (500 MHz, DMSO) δ 8.03 (s, 1H), 7.90 (t, J=8.9 Hz, 2H), 7.79 (s, 1H), 7.73 (dd, J=8.5, 1.8 Hz, 1H), 7.47-7.38 (m, 3H), 6.96 (d, J=8.2 Hz, 1H), 4.66 (s, 2H), 2.17 (s, 6H), 2.06 (s, 3H), 1.76 (s, 6H); $^{13}$C NMR (150 MHz, CDCl3) δ 154.33, 139.11, 138.11, 136.91, 133.67, 133.44, 132.30, 128.66, 128.39, 126.51, 126.14, 125.75, 125.69, 125.42, 124.97, 117.42, 65.73, 40.72, 37.20, 29.19; HRMS Accurate mass (ES+): Found 385.2177, C$_{27}$H$_{29}$O$_2$(M+H+) requires 385.2168.

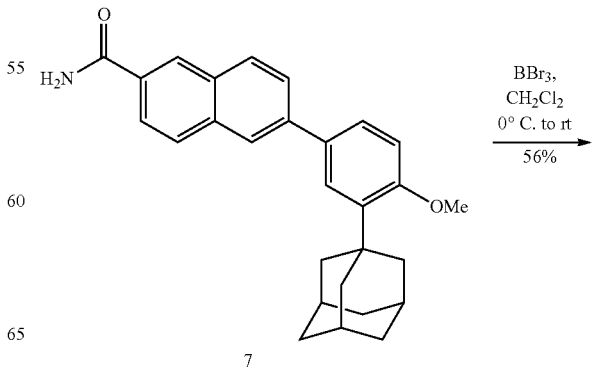

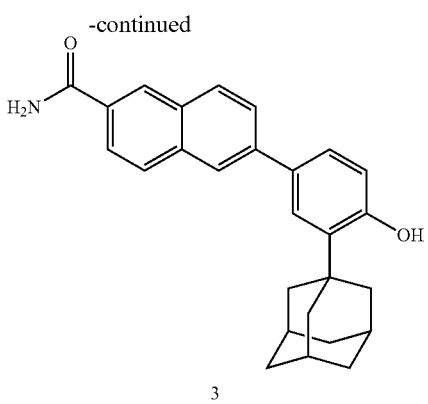

3

6-(3-(adamantan-1-yl)-4-hydroxyphenyl)-2-naphthamide (3)

To a solution of amide 7 (25 mg, 0.061 mmol) in CH$_2$Cl$_2$ (2 mL) at 0° C. was added BBr$_3$ (1M in CH$_2$Cl$_2$, 0.06 mL, 0.06 mmol), the reaction was warmed to room temperature and stirred overnight. The reaction was cooled to 0° C. and quenched with water and allowed to stir for 15 minutes, then extracted with EtOAc 3×. The combined organic layers were washed with water and brine, dried over Na$_2$SO$_4$, filtered, concentrated, and purified by HPLC, yielding the title compound as a white solid (13 mg, 56% yield). $^1$H NMR (500 MHz, DMSO) δ 9.68 (br s, 1H), 8.47 (s, 1H), 8.12 (d, J=9.5 Hz, 2H), 8.02 (d, J=8.6 Hz, 2H), 7.94 (dd, J=8.6, 1.7 Hz, 1H), 7.84 (dd, J=8.6, 1.8 Hz, 1H), 7.54-7.40 (m, 1H), 7.44 (br s, 1H) 6.92 (d, J=8.2 Hz, 1H), 2.17 (s, 6H), 2.07 (s, 3H), 1.76 (s, 6H); $^{13}$C NMR (125 MHz, DMSO) δ 168.36, 156.84, 140.29, 136.44, 135.14, 131.45, 131.15, 130.47, 129.75, 128.28, 127.95, 126.13, 125.71, 125.52, 125.06, 123.99, 117.43, 37.06, 36.77, 28.83; HRMS Accurate mass (ES+): Found 398.2127, C$_{27}$H$_{28}$NO$_2$ (M+H+) requires 398.2120.

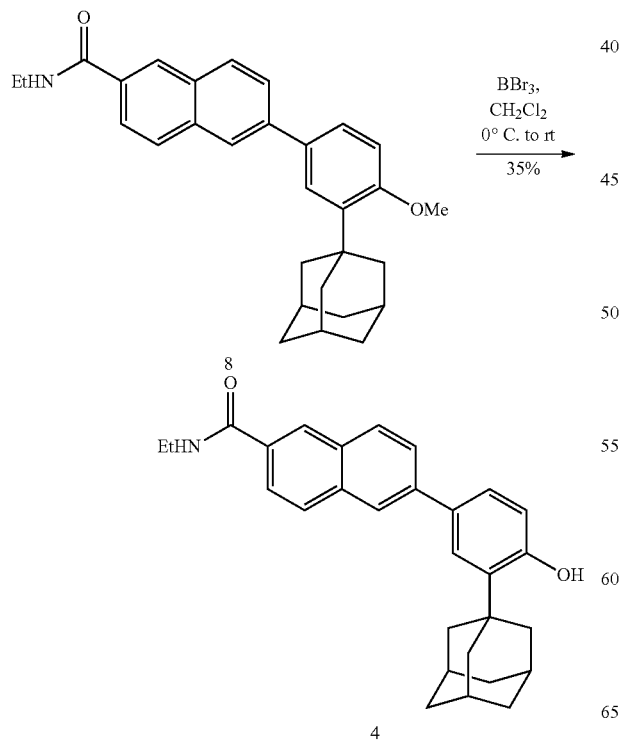

6-(3-(adamantan-1-yl)-4-hydroxyphenyl)-N-ethyl-2-naphthamide (4)

To a solution of amide 8 (25 mg, 0.061 mmol) in CH$_2$Cl$_2$ (2 mL) at 0° C. was added BBr$_3$ (1M in CH$_2$Cl$_2$, 0.12 mL, 0.122 mmol). The reaction was warmed to room temperature and stirred overnight. The reaction was cooled to 0° C. then quenched with water and allowed to stir for 15 minutes, then extracted with EtOAc 3×. The combined organic layers were washed with water and brine, dried over Na$_2$SO$_4$, filtered, concentrated, and purified by HPLC, yielding the title compound as a white solid (5.3 mg, 35% yield). 1H NMR (500 MHz, CDCl$_3$) δ 8.29 (s, 1H), 8.06 (br s, 1H), 7.98 (s, 1H), 7.93 (dd, J=12.3, 8.7 Hz, 2H), 7.82 (dd, J=8.5, 1.8 Hz, 1H), 7.77 (dd, J=8.5, 1.8 Hz, 1H), 7.58 (d, J=2.3 Hz, 1H), 7.41 (dd, J=8.1, 2.3 Hz, 1H), 6.81 (d, J=8.1 Hz, 1H), 3.59 (qd, J=7.3, 5.6 Hz, 2H), 2.22 (s, 6H), 2.12 (s, 3H), 1.81 (s, 6H), 1.32 (t, J=7.3 Hz, 3H); $^{13}$C NMR (125 MHz, CDCl$_3$) δ 168.03, 154.86, 140.92, 137.04, 135.28, 133.01, 131.51, 131.41, 129.39, 128.71, 127.29, 126.74, 126.54, 125.81, 124.82, 123.94, 117.51, 40.70, 37.20, 37.06, 29.19, 15.08; HRMS Accurate mass (ES+): Found 448.2247, C$_{29}$H$_{31}$NO$_2$Na (M+Na+) requires 448.2252.

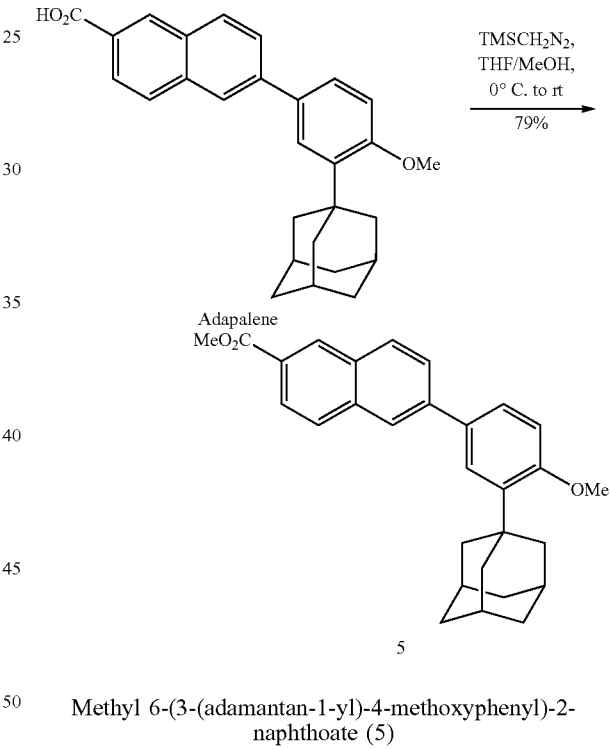

Methyl 6-(3-(adamantan-1-yl)-4-methoxyphenyl)-2-naphthoate (5)

To a solution of adapalene (50 mg, 0.121 mmol) in 4:1 THF/MeOH (0.4 mL) at 0° C. was added TMSCH$_2$N$_2$ (0.15 mL, 0.290 mmol) and the reaction was warmed to room temperature over 1 hour. The reaction mixture was concentrated, 1N HCl was added, and was extracted with EtOAc 3×. The combined organic layers were washed with water and brine, dried over Na$_2$SO$_4$, filtered, and concentrated; yielding the title compound as a white solid (41 mg, 79% yield). $^1$H NMR (500 MHz, CDCl$_3$) δ 8.61 (s, 1H), 8.07 (dd, J=8.6, 1.7 Hz, 1H), 8.03-7.96 (m, 2H), 7.92 (d, J=8.6 Hz, 1H), 7.80 (dd, J=8.5, 1.8 Hz, 1H), 7.60 (d, J=2.4 Hz, 1H), 7.55 (dd, J=8.4, 2.4 Hz, 1H), 7.00 (d, J=8.5 Hz, 1H), 3.99 (s, 3H), 3.91 (s, 3H), 2.19 (s, 6H), 2.10 (s, 3H), 1.80 (s, 6H); $^{13}$C NMR (125 MHz, CDCl$_3$) δ 167.44, 159.03, 141.51, 139.11, 136.06, 132.67, 131.35, 130.95, 129.82, 128.33, 127.02, 126.59, 126.09, 125.84, 125.68, 124.84, 112.21, 55.27, 52.31, 40.72, 37.25, 29.23; HRMS Accurate mass (ES+): Found 427.2268, $C_{29}H_{31}O_3$ (M+H+) requires 427.2273.

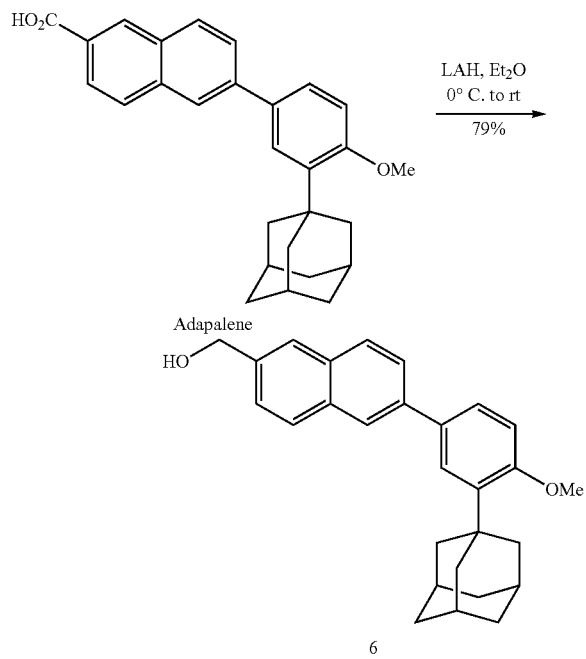

(6-(3-(adamantan-1-yl)-4-methoxyphenyl)naphthalen-2-yl)methanol (6)

To a solution of lithium aluminum hydride (LAH) (5.05 mg, 0.133 mmol) in Et$_2$O (1 mL) at 0° C. was added adapalene (50 mg, 0.121 mmol) in Et$_2$O (0.5 mL). The reaction was warmed to room temperature and stirred for 2 hours. The reaction was cooled to 0° C. and H$_2$O (1 mL) was added slowly followed by 1N NaOH (1 mL). The resulting slurry was filtered over Celite and washed with EtOAc. The aqueous layer was extracted with EtOAc 3× and the combined organics were washed with water and brine, dried over Na$_2$SO$_4$, filtered, and concentrated; yielding the title compound as a white solid (38 mg, 79% yield). $^1$H NMR (500 MHz, CDCl$_3$) δ 7.98 (d, J=1.1 Hz, 1H), 7.88 (t, J=8.5 Hz, 2H), 7.82 (s, 1H), 7.74 (dd, J=8.5, 1.8 Hz, 1H), 7.60 (d, J=2.3 Hz, 1H), 7.53 (dd, J=8.4, 2.3 Hz, 1H), 7.50 (dd, J=8.4, 1.6 Hz, 1H), 6.99 (d, J=8.4 Hz, 1H), 4.87 (s, 2H), 3.90 (s, 3H), 2.20 (s, 6H), 2.11 (s, 3H), 1.81 (s, 6H); $^{13}$C NMR (125 MHz, CDCl$_3$) δ 158.72, 139.19, 139.01, 138.09, 133.44, 133.20, 132.29, 128.64, 128.36, 126.17, 126.01, 125.70, 125.65, 125.40, 124.98, 112.22, 65.69, 55.31, 40.76, 37.28, 29.26; HRMS Accurate mass (ES+): Found 421.2141, $C_{28}H_{31}O_2Na$ (M+Na+) requires 421.2143.

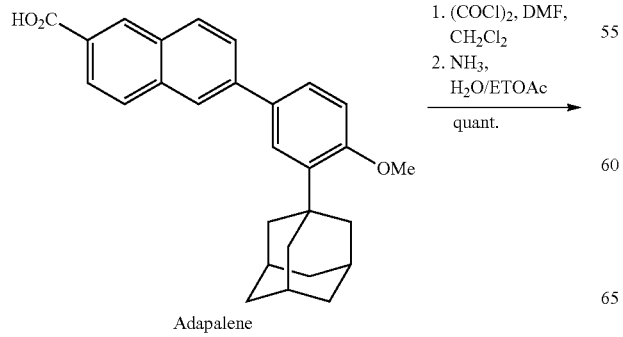

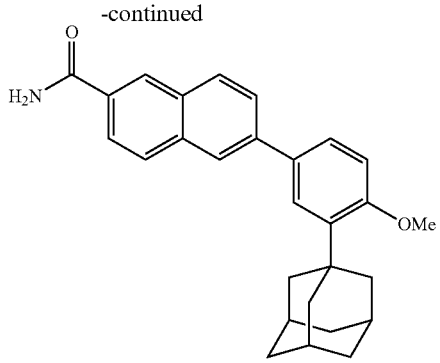

6-(3-(adamantan-1-yl)-4-methoxyphenyl)-2-naphthamide (7)

To a solution of adapalene (50 mg, 0.121 mmol) in CH$_2$Cl$_2$ (3 mL) and DMF (one drop, cat.) was added oxalyl chloride (2M in CH$_2$Cl$_2$, 0.15 mL, 0.30 mmol), and the reaction was stirred at room temperature 2 hours. The reaction was concentrated and dissolved in 8:1 EtOAc/NH$_4$OH (5 mL) and stirred at 0° C. for 30 minutes. The reaction was diluted with EtOAc and water, and the aqueous layer was extracted with EtOAc 3×. The combined organic layers were washed with water and brine, dried over Na$_2$SO$_4$, filtered, and concentrated, yielding the title compound as a white solid (49 mg, quant.). $^1$H NMR (500 MHz, CDCl$_3$) δ 8.36 (s, 1H), 8.02 (s, 1H), 8.00-7.93 (m, 2H), 7.87 (dd, J=8.5, 1.8 Hz, 1H), 7.81 (dd, J=8.5, 1.8 Hz, 1H), 7.60 (d, J=2.4 Hz, 1H), 7.55 (dd, J=8.4, 2.4 Hz, 1H), 7.00 (d, J=8.5 Hz, 1H), 3.91 (s, 3H), 2.19 (s, 6H), 2.11 (s, 3H), 1.80 (s, 6H); $^{13}$C NMR (125 MHz, CDCl$_3$) δ 170.04, 159.00, 141.20, 139.11, 135.53, 132.60, 131.39, 129.97, 129.49, 128.68, 128.09, 126.77, 126.03, 125.79, 124.79, 124.11, 112.22, 55.26, 40.69, 37.20, 29.19; HRMS Accurate mass (ES+): Found 434.2085, $C_{28}H_{29}NO_2Na$ (M+Na+) requires 434.2096.

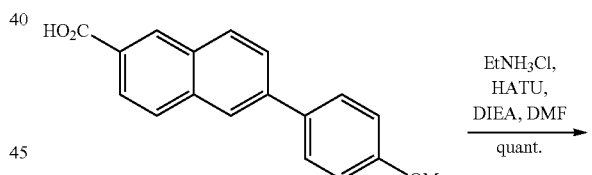

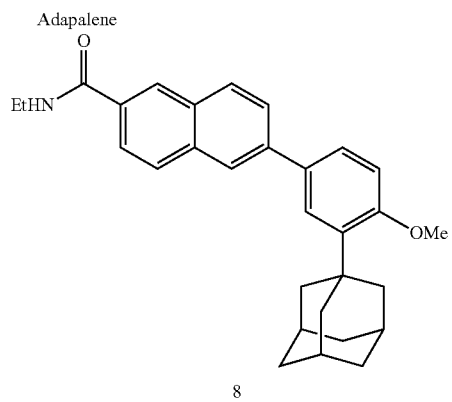

6-(3-(adamantan-1-yl)-4-methoxyphenyl)-N-ethyl-2-naphthamide (8)

To a slurry of adapalene (50 mg, 0.121 mmol) in DMF (3 mL) was added DIEA (0.13 mL, 0.726 mmol) followed by HATU (50.6 mg, 0.133 mmol) and EtNH$_3$Cl (30 mg, 0.363 mmol) and the reaction was stirred at room temperature overnight. The reaction poured into water and quenched with sat. NaHCO$_3$, then extracted with CH$_2$Cl$_2$ 3×. The combined organic layers were washed with water and brine, dried over Na$_2$SO$_4$, filtered, concentrated, and purified by prep TLC (neat EtOAc), yielding the title compound as a white solid (53 mg, quant.). $^1$H NMR (500 MHz, CDCl$_3$) δ 8.28 (s, 1H), 8.00 (s, 1H), 7.94 (dd, J=13.3, 8.6 Hz, 2H), 7.83 (dd, J=8.5, 1.7 Hz, 1H), 7.79 (dd, J=8.5, 1.8 Hz, 1H), 7.59 (d, J=2.4 Hz, 1H), 7.54 (dd, J=8.4, 2.4 Hz, 1H), 7.00 (d, J=8.5 Hz, 1H), 6.24 (br s, 1H), 3.91 (s, 3H), 3.58 (qd, J=7.3, 5.9 Hz, 2H), 2.19 (s, 6H), 2.10 (s, 3H), 1.80 (s, 6H), 1.32 (t, J=7.3 Hz, 3H); $^{13}$C NMR (125 MHz, CDCl$_3$) δ 167.64, 158.98, 140.85, 139.12, 135.23, 132.76, 131.65, 131.53, 129.36, 128.64, 127.15, 126.70, 126.08, 125.81, 124.86, 124.01, 112.24, 55.30, 40.75, 37.27, 35.20, 29.25, 15.13; HRMS Accurate mass (ES+): Found 462.2404, C$_{30}$H$_{33}$NO$_2$Na (M+Na+) requires 462.2409.

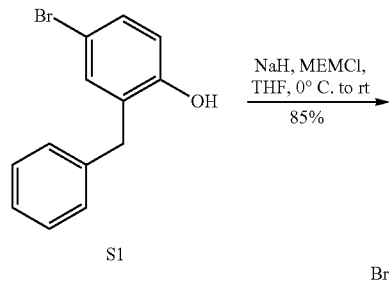

2-benzyl-4-bromo-1-((2-methoxyethoxy)methoxy)benzene (S2)

Phenol S1[55] (1.500 g, 5.701 mmol) dissolved in THF (5 mL) was added via cannula to a suspension of NaH (60% in mineral oil, 296 mg, 7.411 mmol) in THF (15 mL) at 0° C. The solution was warmed to room temperature and stirred for 30 minutes, after which time MEMCl (1.04 mL, 9.12 mmol) was added, and the reaction was stirred for 2 hours at room temperature. The reaction was quenched with water and extracted with EtOAc 3×. The combined organic layers were washed with brine, dried over Na$_2$SO$_4$, filtered, concentrated, and purified by column chromatography, yielding the title compound as a clear oil (1.70 g, 85% yield). $^1$H NMR (500 MHz, CDCl$_3$) δ 7.32-7.27 (m, 3H), 7.25 (d, J=2.5 Hz, 1H), 7.21 (t, J=6.6 Hz, 3H), 7.04 (d, J=8.7 Hz, 1H), 5.25 (s, 2H), 3.96 (s, 2H), 3.66 (dd, J=5.5, 3.7 Hz, 2H), 3.49 (dd, J=5.5, 3.8 Hz, 2H), 3.37 (s, 3H); $^{13}$C NMR (125 MHz, CDCl$_3$) δ 153.91, 139.93, 132.99, 132.38, 130.09, 128.68, 128.22, 125.94, 115.60, 113.87, 93.04, 71.34, 67.49, 58.77, 35.92; HRMS Accurate mass (ES+): Found 375.0382, C$_{17}$H$_{19}$$^{81}$BrO$_3$Na (M+Na+) requires 375.0382.

Methyl 6-(3-benzyl-4-((2-methoxyethoxy)methoxy)phenyl)-2-naphthoate (S4)

To a solution of bromide S2 (198 mg, 0.56 mmol) in THF (5 mL) at −78° C. was added n-BuLi (2.40 M in hexanes, 0.26 mL, 0.62 mmol) dropwise. The reaction was stirred for 15 minutes at −78° C. B(OMe)$_3$ was then added dropwise, and the reaction stirred for an additional hour at −78° C., then warmed to room temperature. After one hour at room temperature, 0.1 M HCl was added (5 mL) and the reaction was stirred for an additional 30 minutes. Water was added, and the solution was extracted with EtOAc 3×. The combined organic layers were washed with brine, dried over Na$_2$SO$_4$, filtered, concentrated and purified by column chromatography (EtOAc/hexanes then MeOH/CH$_2$Cl$_2$). The intended boronic acid product also contained another similar compound, presumably a borate oligomer of the material (Rf=0.75 in 5% MeOH/95% CH$_2$Cl$_2$, stains red in vanillin), both of which reacted in the following step. The boronic acid mixture was then dissolved in 9:1 DME:H$_2$O (5 mL), then methyl 6-bromo-2-naphthoate (S3) (126 mg, 0.47 mmol) and Na$_2$CO$_3$ (100 mg, 0.94 mmol) were added, then argon was bubbled through the mixture for 5 minutes. After degassing, Pd(PPh$_3$)$_4$ (16 mg, 0.014 mmol) was added, and the reaction was heated to 75° C. for 6 hours. Water and EtOAc were added, and the aqueous layer was extracted with EtOAc 3×. The combined organic layers were washed with brine, dried over Na$_2$SO$_4$, filtered, concentrated, and purified by column chromatography, yielding the title compound as a white foam (86 mg, 40% yield with respect to S3). $^1$H NMR (500 MHz, CDCl$_3$) δ 8.60 (s, 1H), 8.06 (dd, J=8.6, 1.7 Hz, 1H), 7.98-7.97 (m, 2H), 7.90 (d, J=8.7 Hz, 1H), 7.75 (dd, J=8.5, 1.8 Hz, 1H), 7.56 (dd, J=8.5, 2.4 Hz, 1H), 7.52 (d, J=2.3 Hz, 1H), 7.30-7.24 (m, 5H), 7.20-7.16 (m, 1H), 5.32 (s, 2H), 4.08 (s, 2H), 3.99 (s, 3H), 3.70-3.65 (m, 2H), 3.52-3.47 (m, 2H), 3.37 (s, 3H); $^{13}$C NMR (125

MHz, CDCl$_3$) δ 167.33, 155.09, 140.88, 140.64, 135.94, 133.96, 131.42, 130.88, 130.76, 129.85, 129.79, 128.91, 128.40, 128.33, 127.15, 126.67, 126.35, 126.02, 125.71, 124.94, 114.47, 93.22, 71.64, 67.71, 59.10, 52.29, 36.59; HRMS Accurate mass (ES+): Found 457.2028, C$_{29}$H$_{29}$O$_5$ (M+H+) requires 457.2015.

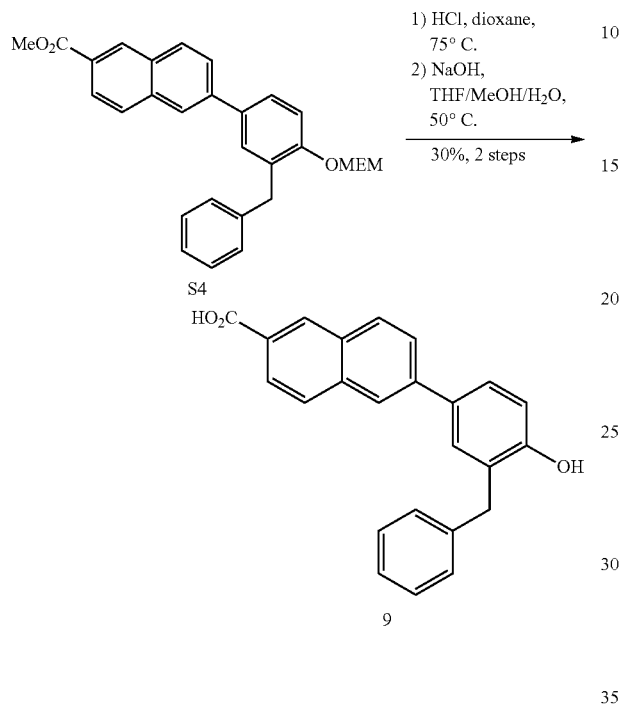

6-(3-benzyl-4-hydroxyphenyl)-2-naphthoic acid (9)

MEM ether S4 (78 mg, 0.17 mmol) was dissolved in dioxane (1.5 mL) and 4M HCl in dioxane (0.5 mL) was added. The reaction was heated to 75° C. for 2 hours. The solution was concentrated under reduced pressure, then dissolved in 1:1 THF:MeOH (2 mL) and 1M NaOH was added (0.34 mL, 0.34 mmol), and this reaction was heated to 50° C. overnight. The following day, the reaction was acidified with 1M HCl (pH 1) and filtered. The filter cake was washed with water, yielding the title compound as a white solid (20 mg, 30% yield over two steps). $^1$H NMR (500 MHz, CD$_3$CN) δ 9.51 (br s, 1H), 8.60 (s, 1H), 8.11 (s, 1H), 8.06 (d, J=8.7 Hz, 1H), 8.02 (dd, J=8.6, 1.6 Hz, 1H), 7.97 (d, J=8.6 Hz, 1H), 7.83 (dd, J=8.6, 1.8 Hz, 1H), 7.61 (d, J=2.4 Hz, 1H), 7.53 (dd, J=8.3, 2.4 Hz, 1H), 7.33-7.25 (m, 4H), 7.20-7.13 (m, 2H), 6.96 (d, J=8.3 Hz, 1H), 4.03 (s, 2H); $^{13}$C NMR (125 MHz, DMSO) δ 167.51, 155.48, 141.24, 139.95, 135.49, 130.83, 130.30, 130.27, 129.81, 129.29, 128.67, 128.25, 128.22, 128.15, 127.56, 126.14, 125.71, 125.55, 123.65, 115.79, 35.53; HRMS Accurate mass (ES+): Found 355.1331, C$_{24}$H$_{19}$O$_3$(M+H+) requires 355.1334.

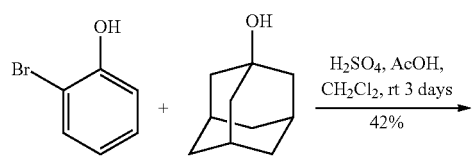

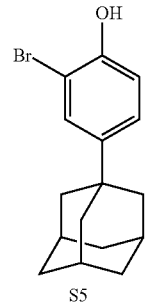

4-(adamantan-1-yl)-2-bromophenol (S5)

To a mixture of 2-bromophenol (1.475 g, 8.526 mmol) and 1-adamantol (1.298 g, 8.526 mmol) in CH$_2$Cl$_2$ (4 mL) was added 5:1 AcOH:H$_2$SO$_4$ (3 mL), and the reaction was stirred at room temperature for 3 days. The reaction poured into water and quenched with sat. NaHCO$_3$, then extracted with CH$_2$Cl$_2$ 3×. The combined organic layers were washed with water and brine, dried over Na$_2$SO$_4$, filtered, concentrated, and purified by column chromatography (loaded crude oil in hexanes, 0-2% EtOAc/hexanes), yielding the title compound as a white solid (1.100 g, 42% yield). $^1$H NMR (500 MHz, CDCl$_3$) δ 7.41 (d, J=2.3 Hz, 1H), 7.21 (dd, J=8.5, 2.3 Hz, 1H), 6.98-6.95 (m, 1H), 5.34 (s, 1H), 2.08 (s, 3H), 1.85 (d, J=2.6 Hz, 6H), 1.81-1.70 (m, 6H); $^{13}$C NMR (125 MHz, CDCl$_3$) δ 150.10, 145.54, 128.70, 125.83, 115.68, 110.16, 68.11, 43.40, 36.78, 35.83, 29.02, 25.74; HRMS Accurate mass (ES+): Found 307.0711, C$_{16}$H$_{20}$$^{79}$BrO (M+H+) requires 307.0698.

1-(3-bromo-4-((2-methoxyethoxy)methoxy)phenyl) adamantane (S6)

To a suspension of sodium hydride (60% in mineral oil, 258 mg, 6.453 mmol) in THF (5 mL) at 0° C. was added a solution of phenol S5 (1.525 g, 4.964 mmol) in THF (3 mL) dropwise. The ice bath was removed and the reaction was stirred at room temperature for 30 minutes, at which time MEMCl (0.91 mL, 7.942 mmol) was added. After 2 hours at room temperature, the reaction was quenched with water and extracted with EtOAc 3×. The combined organic layers were washed with brine, dried over Na$_2$SO$_4$, filtered, concentrated, and purified by column chromatography, yielding the title compound as a clear oil (1.650 g, 84% yield). $^1$H NMR (500 MHz, CDCl$_3$) δ 7.50 (d, J=2.3 Hz, 1H), 7.22 (dd, J=8.6, 2.3 Hz, 1H), 7.13 (d, J=8.7 Hz, 1H), 5.30 (d, J=5.2 Hz, 2H), 3.89-3.85 (m, 2H), 3.59-3.55 (m, 2H), 3.37 (s, 3H), 2.08 (s, 3H), 1.85 (d, J=2.3 Hz, 6H), 1.75 (dd, J=26.7, 12.1 Hz, 6H); $^{13}$C NMR (125 MHz, CDCl$_3$) δ 151.53, 146.85, 130.11, 125.04, 116.05, 112.65, 94.33, 71.62, 68.02, 59.12, 43.28, 36.74, 35.84, 28.96; HRMS Accurate mass (ES+): Found 417.1058, C$_{20}$H$_{27}$$^{79}$BrO$_3$Na (M+Na+) requires 417.1041.

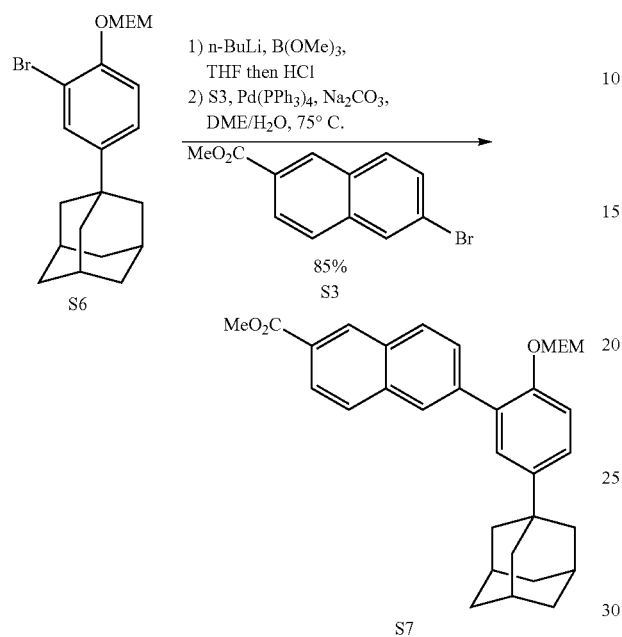

Methyl 6-(5-(adamantan-1-yl)-2-((2-methoxyethoxy)methoxy)phenyl)-2-naphthoate (S7)

To a solution of bromide S6 (31 mg, 0.079 mmol) in THF (2 mL) at −78° C. was added n-BuLi (2.40 M in hexanes, 0.036 mL, 0.087 mmol) dropwise and then stirred for 15 minutes at −78° C., over which time the reaction turned blue. B(OMe)$_3$ was then added dropwise, and the reaction stirred for an additional hour at −78° C., then warmed to room temperature, over which time the reaction turned maroon. After one hour at room temperature, 0.1 M HCl was added (2 mL) and the reaction was stirred for an additional 30 minutes. Water was added, and the solution was extracted with EtOAc 3x. The combined organic layers were washed with brine, dried over Na$_2$SO$_4$, filtered, concentrated and purified by column chromatography (EtOAc/hexanes then MeOH/CH$_2$Cl$_2$). The intended boronic acid product also contained another similar compound, presumably a borate oligomer of the material (Rf=0.75 in 5% MeOH/95% CH$_2$Cl$_2$, stains red in vanillin), both of which reacted in the following step. The boronic acid mixture was then dissolved in 9:1 DME:H$_2$O (2 mL), then methyl 6-bromo-2-naphthoate (21 mg, 0.079 mmol), and Na$_2$CO$_3$ (17 mg, 0.158 mmol) were added, then argon was bubbled through the mixture for 5 minutes. After degassing, Pd(PPh$_3$)$_4$ (3 mg, 0.002 mmol) was added, and the reaction was heated to 75° C. for 6 hours. Water and EtOAc were added, and the aqueous layer was extracted with EtOAc 3x. The combined organic layers were washed with brine, dried over Na$_2$SO$_4$, filtered, concentrated, and purified by column chromatography, yielding the title compound as a white foam (34 mg, 85% yield with respect to naphthyl bromide). $^1$H NMR (500 MHz, CDCl$_3$) δ 8.63 (s, 1H), 8.07 (d, J=8.6 Hz, 1H), 7.99-7.89 (m, 3H), 7.75 (d, J=8.5 Hz, 1H), 7.40 (s, 1H), 7.34 (d, J=8.6 Hz, 1H), 7.25 (d, J=8.2 Hz, 1H), 5.21 (s, 2H), 3.99 (s, 3H), 3.72-3.65 (m, 2H), 3.49-3.42 (m, 2H), 3.32 (s, 3H), 2.10 (s, 3H), 1.95 (s, 6H), 1.77 (q, J=12.2 Hz, 6H); $^{13}$C NMR (125 MHz, CDCl$_3$) δ 167.44, 152.34, 145.63, 139.61, 135.65, 131.47, 130.89, 130.71, 129.23, 128.68, 128.41, 127.99, 127.88, 127.31, 125.73, 125.46, 115.63, 94.46, 71.61, 67.82, 59.07, 52.32, 43.46, 36.87, 35.91, 29.07; HRMS Accurate mass (ES+): Found 523.2461, C$_{32}$H$_{36}$O$_5$Na (M+Na+) requires 523.2460.

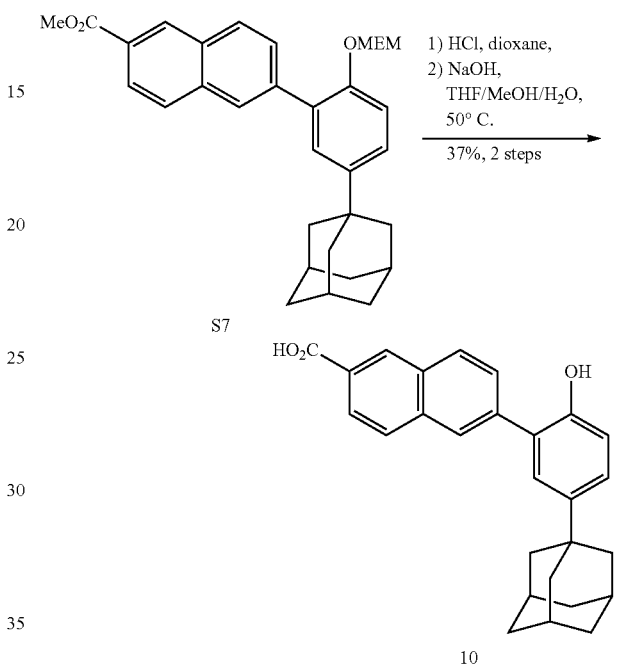

6-(5-(adamantan-1-yl)-2-hydroxyphenyl)-2-naphthoic acid (10)

MEM ether S7 (34 mg, 0.068 mmol) was dissolved in 4M HCl in dioxane (1 mL), and stirred for 2 hours at room temperature. The solution was concentrated under reduced pressure, then dissolved in 1:1 THF:MeOH (2 mL) and 1M NaOH was added (0.34 mL, 0.34 mmol), and this reaction was heated to 50° C. overnight. The following day, the reaction was acidified with 1M HCl (pH 1) and extracted with EtOAc 3x. The combined organic layers were washed with brine, dried over Na$_2$SO$_4$, filtered, concentrated, and purified by column chromatography (0 to 3% MeOH/0.1% AcOH/CH$_2$Cl$_2$, loaded in EtOAc), yielding the title compound as a white solid (10 mg, 37% yield over two steps). $^1$H NMR (500 MHz, DMSO) δ 13.06 (br s, 1H), 9.47 (br s, 1H), 8.60 (d, J=0.7 Hz, 1H), 8.13-8.07 (m, 2H), 8.04 (d, J=8.8 Hz, 1H), 7.97 (dd, J=8.5, 1.6 Hz, 1H), 7.82 (dd, J=8.5, 1.7 Hz, 1H), 7.32 (d, J=2.5 Hz, 1H), 7.20 (dd, J=8.5, 2.5 Hz, 1H), 6.93 (d, J=8.5 Hz, 1H), 2.04 (s, 3H), 1.88 (d, J=2.7 Hz, 6H), 1.72 (s, 6H); $^{13}$C NMR (100 MHz, DMSO) δ 167.56, 152.33, 142.08, 139.35, 135.05, 130.83, 130.18, 128.88, 128.46, 128.32, 127.73, 127.14, 126.89, 126.48, 125.35, 125.18, 115.82, 42.88, 36.23, 35.11, 28.41; HRMS Accurate mass (ES+): Found 399.1957, C$_{27}$H$_{27}$O$_3$(M+H+) requires 399.1960.

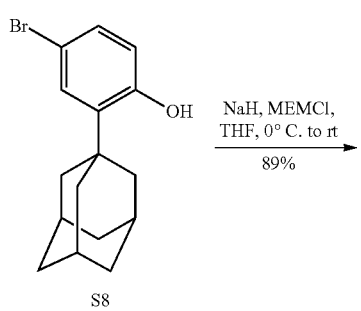

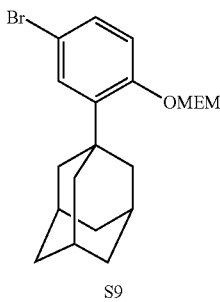

1-(5-bromo-2-((2-methoxyethoxy)methoxy)phenyl) adamantane (S9)

To a suspension of sodium hydride (60% in mineral oil, 53 mg, 1.33 mmol) in THF (3 mL) at 0° C. was added phenol S8[56] (314 mg, 1.02 mmol) dissolved in THF (2 mL). The solution was warmed to room temperature and stirred for one hour, at which time MEMCl (0.19 mL, 1.64 mmol) was added dropwise, and the reaction was stirred for two hours at room temperature. The reaction was quenched with water, and extracted with EtOAc 3×. The combined organic layers were washed with water then brine, dried over $Na_2SO_4$, filtered, concentrated, and purified by column chromatography, yielding the title compound as a white solid (361 mg, 89% yield). $^1$H NMR (500 MHz, $CDCl_3$) δ 7.31 (d, J=2.5 Hz, 1H), 7.23 (dd, J=8.7, 2.5 Hz, 1H), 7.04 (d, J=8.7 Hz, 1H), 5.28 (s, 2H), 3.87-3.79 (m, 2H), 3.59-3.56 (m, 2H), 3.39 (s, 3H), 2.06 (s, 9H), 1.76 (s, 6H); $^{13}$C NMR (125 MHz, $CDCl_3$) δ 155.68, 140.93, 129.95, 129.55, 116.49, 114.54, 93.51, 71.62, 67.91, 59.11, 40.52, 37.31, 37.02, 29.03; HRMS Accurate mass (ES+): Found 417.1036, $C_{20}H_{27}{}^{79}BrO_3Na$ (M+Na+) requires 417.1041.

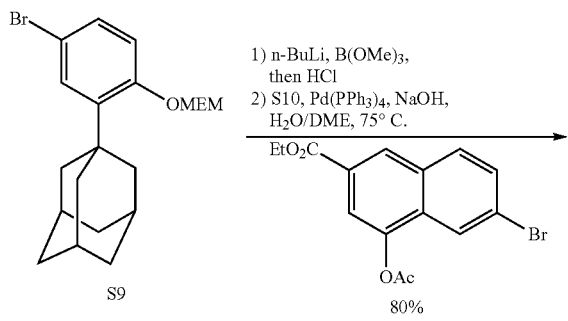

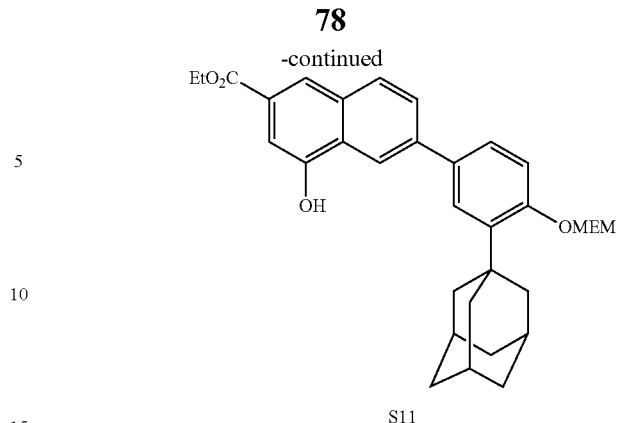

Ethyl 6-(3-(adamantan-1-yl)-4-((2-methoxyethoxy)methoxy)phenyl)-4-hydroxy-2-naphthoate (S11)

General Procedure A:

To a solution of bromide S9 (68 mg, 0.172 mmol) in THF (2 mL) at −78° C. was added n-BuLi (2.40 M in hexanes, 0.036 mL, 0.087 mmol) dropwise and then stirred for 15 minutes at −78° C., over which time the reaction turned blue. $B(OMe)_3$ was then added dropwise, and the reaction stirred for an additional hour at −78° C., then warmed to room temperature, over which time the reaction turned maroon. After one hour at room temperature, 0.1 M HCl was added (2 mL) and the reaction was stirred for an additional 30 minutes. Water was added, and the solution was extracted with EtOAc 3×. The combined organic layers were washed with brine, dried over $Na_2SO_4$, filtered, concentrated and purified by column chromatography (EtOAc/hexanes then MeOH/$CH_2Cl_2$). The intended boronic acid product also contained another similar compound, presumably a borate oligomer of the material (Rf=0.75 in 5% MeOH/95% $CH_2Cl_2$, stains red in vanillin), both of which reacted in the following step. The boronic acid mixture was then dissolved in DME (2 mL), then naphthyl bromide S10[57] (53 mg, 0.143 mmol), and 1M NaOH (0.72 mL, 0.72 mmol) were added, then argon was bubbled through the mixture for 5 minutes. After degassing, $Pd(PPh_3)_4$ (5 mg, 0.004 mmol) was added, and the reaction was heated to 75° C. for 4 hours, at which time another portion of 1M NaOH (0.72 mL, 0.72 mmol) was added, to ensure complete acetate hydrolysis. After 2 additional hours, the reaction was complete by TLC and S10 was consumed. Water and EtOAc were added, and the aqueous layer was extracted with EtOAc 3×. The combined organic layers were washed with brine, dried over $Na_2SO_4$, filtered, concentrated, and purified by column chromatography, yielding the title compound as a white foam (64 mg, 80% yield with respect to S10). $^1$H NMR (500 MHz, $CDCl_3$) δ 8.40 (s, 1H), 8.21 (s, 1H), 7.95 (d, J=8.6 Hz, 1H), 7.79 (dd, J=8.5, 1.8 Hz, 1H), 7.65-7.60 (m, 2H), 7.53 (dd, J=8.5, 2.3 Hz, 1H), 7.27 (d, J=8.4 Hz, 1H), 6.64 (br s, 1H), 5.38 (s, 2H), 4.46 (q, J=7.1 Hz, 2H), 3.95-3.88 (m, 2H), 3.69-3.62 (m, 2H), 3.44 (s, 3H), 2.19 (d, J=2.0 Hz, 6H), 2.10 (s, 3H), 1.80

(s, 6H), 1.46 (t, J=7.1 Hz, 3H); $^{13}$C NMR (125 MHz, CDCl$_3$) δ 167.41, 156.59, 152.38, 140.70, 139.06, 134.07, 132.71, 129.68, 127.39, 126.96, 126.23, 126.08, 123.35, 119.37, 115.19, 108.12, 93.51, 71.80, 67.97, 61.48, 59.21, 40.85, 37.40, 37.23, 29.23, 14.51; HRMS Accurate mass (ES+): Found 531.2758, C$_{33}$H$_{39}$O$_6$(M+H+) requires 531.2747.

6H); $^{13}$C NMR (100 MHz, CD$_3$CN) δ 167.87, 156.85, 153.83, 141.36, 137.78, 133.46, 132.88, 130.63, 128.30, 128.17, 127.45, 126.85, 126.61, 123.50, 119.26, 108.29, 41.05, 37.74, 30.04; HRMS Accurate mass (ES+): Found 415.1906, C$_{27}$H$_{27}$O$_4$(M+H+) requires 415.1909.

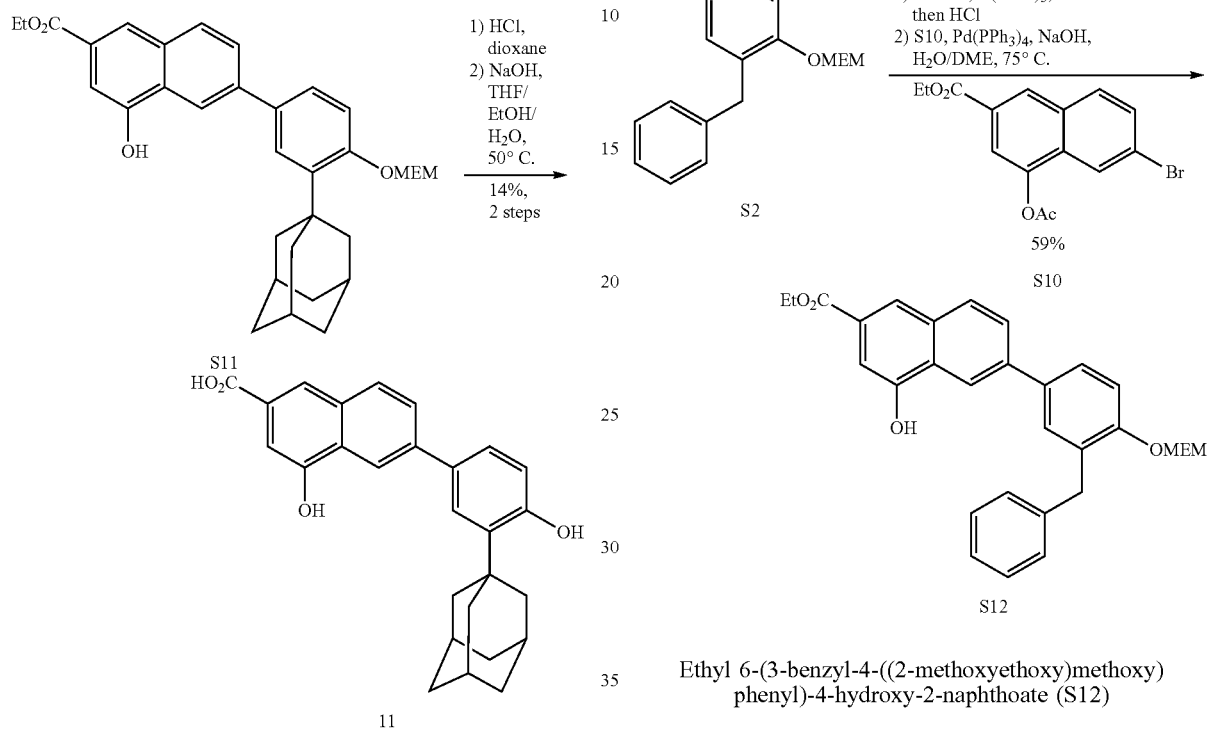

6-(3-(adamantan-1-yl)-4-hydroxyphenyl)-4-hydroxy-2-naphthoic acid (11)

General Procedure B:

MEM ether S11 (20 mg, 0.038 mmol) was dissolved in 4M HCl in dioxane (2 mL) and the reaction was stirred at room temperature overnight. The reaction was quenched with water and extracted with EtOAc 3×. The combined organic layers were washed with brine, dried over Na$_2$SO$_4$, filtered, and concentrated. The crude intermediate was dissolved in 2:1 EtOH/THF (1.5 mL) and 1N NaOH was added (0.2 mL), the mixture was heated to 50° C. and stirred overnight. The reaction was cooled to room temperature, acidified (pH 1) with 1M HCl and extracted with EtOAc 3×. The combined organic layers were washed with brine, dried over Na$_2$SO$_4$, filtered, concentrated, and purified by column chromatography (0→6% MeOH/0.1% AcOH/CH$_2$Cl$_2$) yielding the title compound as a white solid (2.1 mg, 14% over two steps). $^1$H NMR (500 MHz, CD$_3$CN) δ 8.33 (d, J=1.9 Hz, 1H), 8.14 (s, 1H), 8.00 (d, J=8.5 Hz, 1H), 7.84 (dd, J=8.6, 1.9 Hz, 1H), 7.58 (d, J=2.4 Hz, 1H), 7.47 (dd, J=8.2, 2.4 Hz, 1H), 7.37 (d, J=1.4 Hz, 1H), 6.88 (d, J=8.2 Hz, 1H), 2.22-2.19 (m, 6H), 2.10-2.07 (m, 3H), 1.81 (t, J=2.8 Hz, Ethyl 6-(3-benzyl-4-((2-methoxyethoxy)methoxy)phenyl)-4-hydroxy-2-naphthoate (S12)

Following general procedure A, bromide S2 (40 mg, 0.114 mmol) and naphthyl bromide S10 (32 mg, 0.095 mmol) yielded the title compound as a clear oil (26 mg, 59% yield with respect to S10). $^1$H NMR (400 MHz, CDCl$_3$) δ 8.35 (s, 1H), 8.20 (s, 1H), 7.93 (d, J=8.5 Hz, 1H), 7.75 (dd, J=8.5, 1.8 Hz, 1H), 7.60-7.54 (m, 2H), 7.48 (d, J=1.2 Hz, 1H), 7.26-7.23 (m, 5H), 7.20-7.14 (m, 1H), 5.80 (br s, 1H), 5.30 (s, 2H), 4.43 (q, J=7.1 Hz, 2H), 4.07 (s, 2H), 3.69-3.61 (m, 2H), 3.53-3.45 (m, 2H), 3.36 (s, 3H), 1.44 (t, J=7.1 Hz, 3H); $^{13}$C NMR (125 MHz, CDCl$_3$) δ 167.48, 155.01, 152.52, 141.04, 139.89, 134.27, 132.74, 130.62, 129.92, 129.71, 128.90, 128.39, 127.45, 126.79, 126.70, 125.98, 123.20, 119.40, 114.45, 108.12, 93.20, 71.70, 67.67, 61.52, 59.12, 36.70, 29.84, 14.49; HRMS Accurate mass (ES+): Found 487.2126, C$_{30}$H$_{31}$O$_6$(M+H+) requires 487.2121.

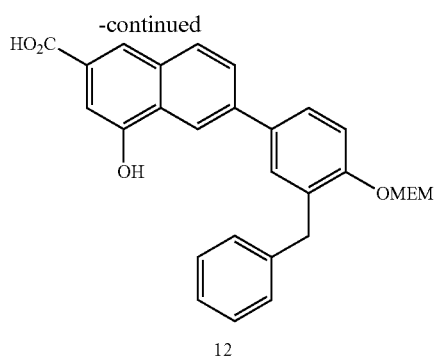

6-(3-benzyl-4-hydroxyphenyl)-4-hydroxy-2-naphthoic acid (12)

Following general procedure B, MEM ether S12 (25 mg, 0.055 mmol) yielded the title compound as a yellow residue (7.0 mg, 35% yield over two steps). $^1$H NMR (500 MHz, CD$_3$CN) δ 8.31 (s, 1H), 8.15 (d, J=14.7 Hz, 1H), 8.01-7.93 (m, 1H), 7.83-7.77 (m, 1H), 7.58 (d, J=1.9 Hz, 1H), 7.54-7.50 (m, 1H), 7.37 (s, 1H), 7.28 (q, J=8.1 Hz, 4H), 7.18 (t, J=6.9 Hz, 1H), 6.95 (d, J=8.3 Hz, 2H), 4.02 (s, 2H); $^{13}$C NMR (125 MHz, CD$_3$CN) δ 172.55, 167.98, 155.76, 153.85, 142.27, 140.70, 133.53, 133.20, 130.65, 129.69, 129.46, 129.31, 128.27, 127.40, 127.29, 126.85, 123.49, 119.33, 116.72, 108.35, 36.52; HRMS Accurate mass (ES+): Found 393.1093, C$_{24}$H$_{18}$O$_4$Na (M+Na+) requires 393.1103.

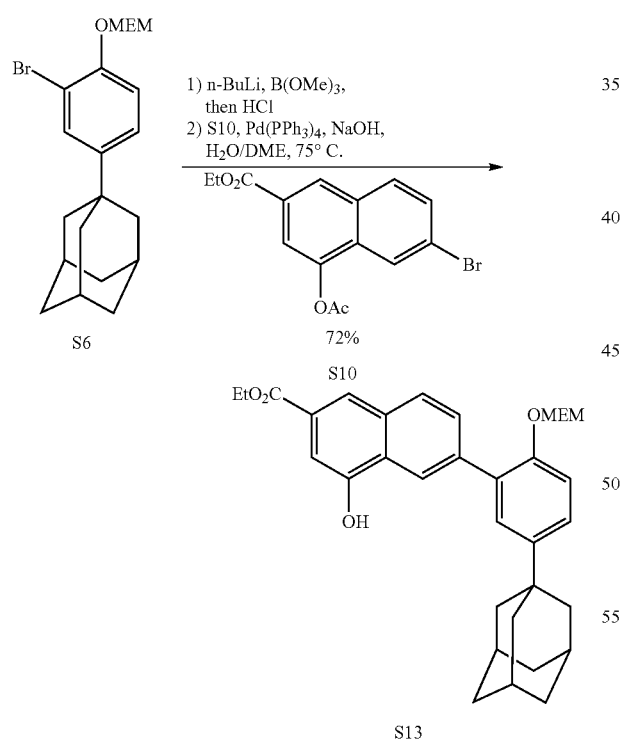

Ethyl 6-(5-(adamantan-1-yl)-2-((2-methoxyethoxy)methoxy)phenyl)-4-hydroxy-2-naphthoate (S13)

Following general procedure A, bromide S6 (66 mg, 0.167 mmol) and naphthyl bromide S10 (47 mg, 0.139 mmol) yielded the title compound as a clear oil (53 mg, 72% yield with respect to S10). $^1$H NMR (500 MHz, CDCl$_3$) δ 8.37 (s, 1H), 8.22 (s, 1H), 7.93 (d, J=8.4 Hz, 1H), 7.75 (d, J=8.2 Hz, 1H), 7.58 (s, 1H), 7.42 (s, 1H), 7.31 (t, J=11.5 Hz, 1H), 7.23 (d, J=8.6 Hz, 1H), 6.76 (br s, 1H), 5.22 (s, 2H), 4.46 (dd, J=13.7, 6.7 Hz, 2H), 3.73 (s, 2H), 3.50 (s, 2H), 3.34 (s, 3H), 2.10 (s, 3H), 1.94 (s, 6H), 1.77 (q, J=11.6 Hz, 6H), 1.46 (t, J=7.0 Hz, 3H); $^{13}$C NMR (125 MHz, CDCl$_3$) δ 167.42, 152.23, 145.60, 138.77, 132.77, 131.05, 129.56, 128.60, 127.97, 127.64, 127.03, 125.61, 123.23, 122.38, 115.46, 108.00, 94.35, 71.70, 67.88, 61.49, 59.10, 43.45, 36.88, 35.90, 29.09, 14.51; HRMS Accurate mass (ES+): Found 553.2562, C$_{33}$H$_{38}$O$_6$Na (M+Na+) requires 553.2566.

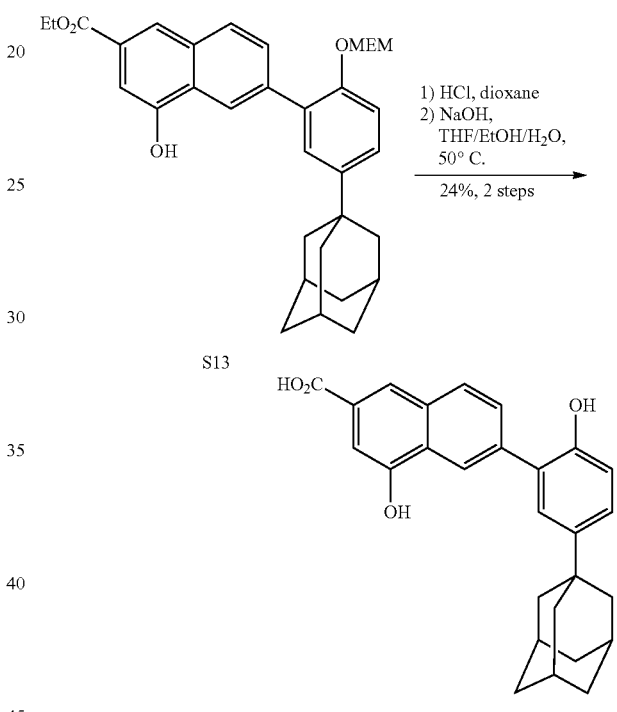

6-(5-(adamantan-1-yl)-2-hydroxyphenyl)-4-hydroxy-2-naphthoic acid (13)

Following general procedure B, MEM ether S13 (39 mg, 0.073 mmol) yielded the title compound as a yellow residue (7.2 mg, 24% yield over two steps). $^1$H NMR (500 MHz, CD$_3$CN) δ 8.31 (s, 1H), 8.17 (s, 1H), 7.98 (d, J=8.5 Hz, 1H), 7.78 (dd, J=8.5, 1.7 Hz, 1H), 7.40-7.35 (m, 2H), 7.24 (dd, J=8.5, 2.5 Hz, 1H), 6.90 (d, J=8.5 Hz, 1H), 1.97-1.95 (m, 6H), 1.93-1.90 (m, 3H), 1.81-1.75 (m, 6H); $^{13}$C NMR (125 MHz, CD$_3$CN) δ 172.64, 168.08, 153.93, 152.55, 144.70, 139.34, 133.62, 130.15, 129.69, 128.49, 128.44, 128.35, 127.93, 126.55, 123.48, 122.82, 116.84, 108.17, 44.04, 37.37, 30.04; HRMS Accurate mass (ES+): Found 415.1905, C$_{27}$H$_{27}$O$_4$ (M+H+) requires 415.1909.

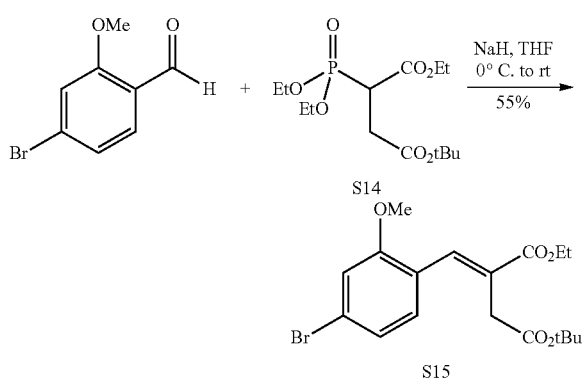

4-(tert-butyl) 1-ethyl (E)-2-(4-bromo-2-methoxy-benzylidene)succinate (S15)

To a suspension of NaH (60% in mineral oil, 176 mg, 4.6 mmol) in THF (10 mL) at 0° C. was added phosphonate S14[58] (1.56 g, 4.6 mmol), and the solution was warmed to room temperature and stirred for 1 hour. The solution was cooled back down to 0° C. and 4-bromo-2-methoxybenzaldehyde dissolved in THF (2 mL) was added dropwise. The resulting orange suspension was allowed to warm to room temperature and stirred overnight. The following day, the solvent was concentrated and diluted with EtOAc, then washed with water 3× and brine, dried over Na$_2$SO$_4$, filtered, concentrated, and purified by column chromatography, yielding the title compound as a clear oil (731 mg, 55% yield). $^1$H NMR (500 MHz, CDCl$_3$) δ 7.83 (s, 1H), 7.15 (dd, J=8.1, 0.6 Hz, 1H), 7.10 (dd, J=8.1, 1.7 Hz, 1H), 7.04 (d, J=1.7 Hz, 1H), 4.27 (q, J=7.1 Hz, 2H), 3.84 (s, 3H), 3.34 (d, J=0.6 Hz, 2H), 1.46 (s, 9H), 1.33 (t, J=7.1 Hz, 3H); $^{13}$C NMR (100 MHz, CDCl$_3$) δ 170.52, 167.38, 158.19, 136.60, 130.77, 127.51, 123.88, 123.65, 123.44, 114.42, 81.09, 61.16, 55.92, 35.37, 28.15, 14.40; HRMS Accurate mass (ES+): Found 365.0007, C$_{14}$H$_{15}$$^{79}$BrO$_5$Na (M+Na+) requires 365.0001.

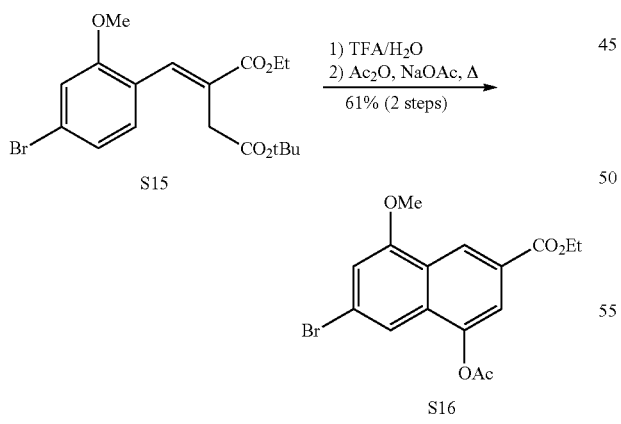

Ethyl 4-acetoxy-6-bromo-8-methoxy-2-naphthoate (S16)

Ester S15 (1.02 g, 2.55 mmol) was dissolved in 9:1 TFA:H$_2$O (3 mL) and stirred at room temperature for 3.5 hours. The reaction was concentrated under reduced pressure and azeotropically dried twice with toluene. The crude oil was cooled to 0° C. and saturated NaHCO$_3$ was added (3 mL), then the mixture was acidified with 1M HCl (pH 1). The aqueous layer was extracted with EtOAc 3×, and the combined organic layers were washed with brine, dried over Na$_2$SO$_4$, filtered and concentrated, yielding the crude acid as a clear oil. The crude acid was dissolved in Ac$_2$O (13 mL) and sodium acetate (227 mg, 2.77 mmol) was added, and the mixture turned from pink to yellow. The reaction was refluxed for 2 hours, cooled to room temperature, and then poured into water. The yellow precipitate was filtered and washed with water. The solids were dissolved in CH$_2$Cl$_2$, washed with brine, and dried over Na$_2$SO$_4$, filtered and concentrated, yielding the title compound as a yellow solid (568 mg, 61% yield over two steps). $^1$H NMR (500 MHz, CDCl$_3$) δ 8.84 (dd, J=1.5, 0.9 Hz, 1H), 7.86 (d, J=1.6 Hz, 1H), 7.59 (dd, J=1.5, 0.9 Hz, 1H), 6.97 (d, J=1.6 Hz, 1H), 4.43 (q, J=7.1 Hz, 1H), 4.03 (s, 1H), 2.48 (s, 1H), 1.43 (t, J=7.1 Hz, 1H); $^{13}$C NMR (125 MHz, CDCl3) δ 169.12, 165.80, 157.05, 145.38, 130.60, 127.18, 124.77, 123.72, 123.23, 119.56, 115.85, 109.31, 61.41, 56.08, 21.01, 14.43; HRMS Accurate mass (ES+): Found 367.0162, C$_{16}$H$_{16}$$^{79}$BrO$_5$ (M+H+) requires 367.0181.

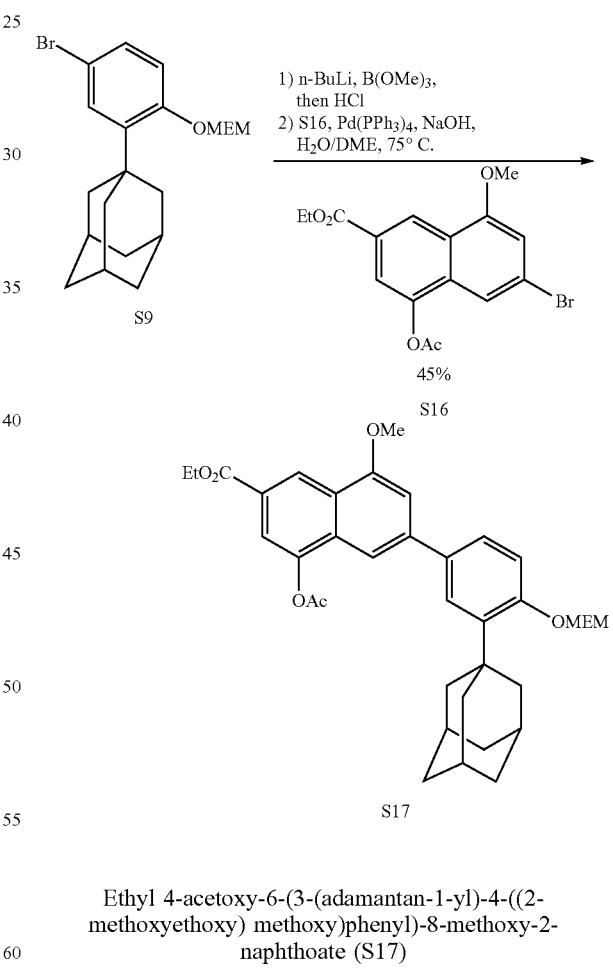

Ethyl 4-acetoxy-6-(3-(adamantan-1-yl)-4-((2-methoxyethoxy) methoxy)phenyl)-8-methoxy-2-naphthoate (S17)

Following general procedure A, bromide S9 (43 mg, 0.109 mmol) and naphthyl bromide S16 (30 mg, 0.090 mmol) yielded the title compound as a clear oil (21 mg, 45% yield with respect to S16). $^1$H NMR (500 MHz, CDCl$_3$) δ 8.92 (s, 1H), 7.86 (s, 1H), 7.53 (d, J=8.4 Hz, 2H), 7.47 (d, J=8.4 Hz, 1H), 7.29 (d, J=8.4 Hz, 1H), 7.08 (s, 1H), 5.40 (s, 2H), 4.44 (q, J=7.1 Hz, 2H), 4.10 (s, 3H), 3.94-3.86 (m, 2H), 3.67-3.60 (m, 2H), 3.42 (s, 3H), 2.47 (s, 3H), 2.19 (s, 6H), 2.11 (s, 3H), 1.81 (s, 6H), 1.45 (t, J=7.1 Hz, 3H); $^{13}$C NMR (125 MHz, CDCl$_3$) δ 169.44, 166.29, 157.00, 156.80, 146.60, 143.00, 139.11, 134.51, 130.47, 126.45, 126.28, 126.18, 125.12, 123.43, 118.85, 115.16, 111.03, 105.42, 93.49, 71.74, 68.01, 61.31, 59.21, 55.94, 40.80, 37.39, 37.19, 29.82, 29.19, 21.11, 14.55; HRMS Accurate mass (ES+): Found 625.2781, C$_{36}$H$_{42}$O$_8$Na (M+Na+) requires 625.2777.

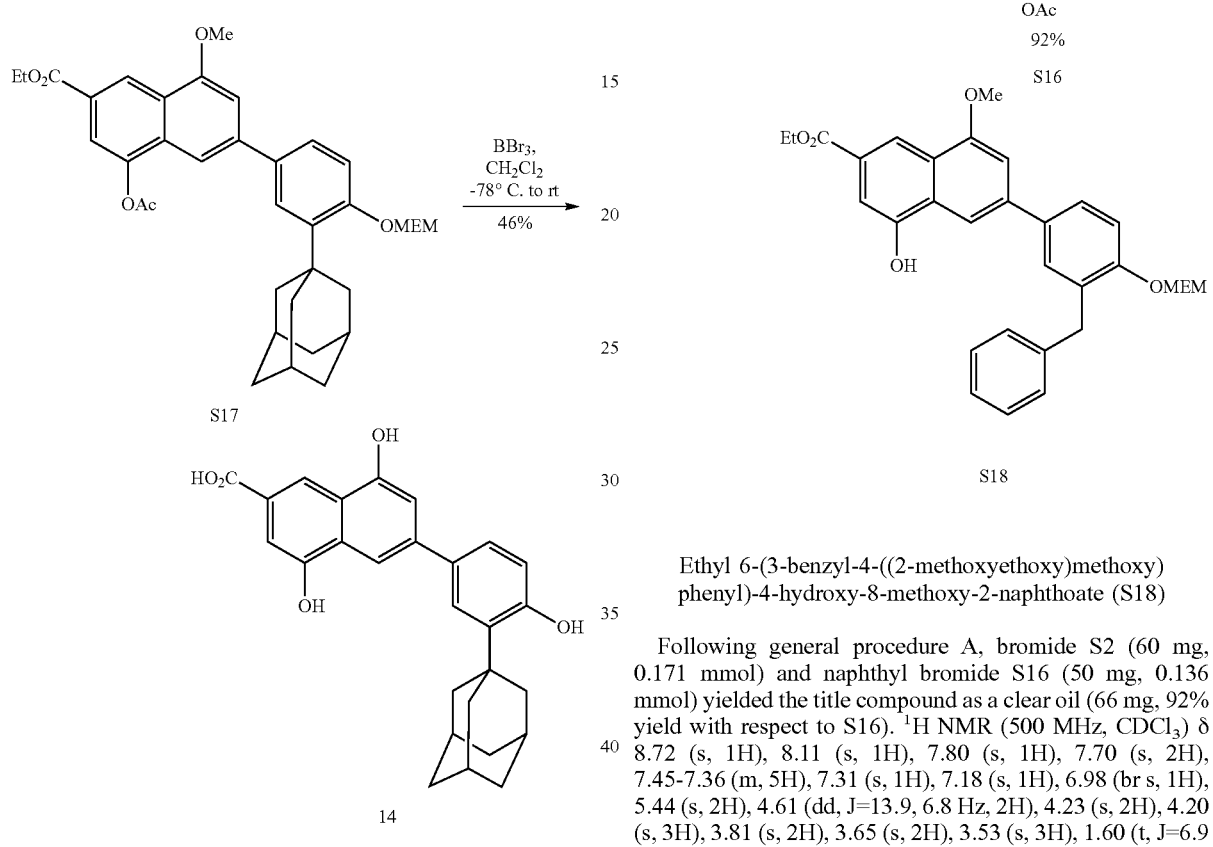

6-(3-(adamantan-1-yl)-4-hydroxyphenyl)-4,8-dihydroxy-2-naphthoic acid (14)

General Procedure C:

To a solution of MEM ether S17 (18 mg, 0.03 mmol) dissolved in CH$_2$Cl$_2$ (2 mL) at −78° C. was added BBr$_3$ (1M in CH$_2$Cl$_2$, 0.24 mL, 0.24 mmol) dropwise, and the mixture was allowed to warm to room temperature and stir overnight. The reaction was quenched with water and extracted with EtOAc 3×. The combined organic layers were washed with brine, dried over Na$_2$SO$_4$, filtered, concentrated, and purified by column chromatography (0→6% MeOH/0.1% AcOH/DCM) yielding the title compound as an orange oil (7 mg, 46% yield). 1H NMR (400 MHz, CD$_3$CN) δ 8.37 (s, 1H), 7.85 (s, 1H), 7.55 (d, J=2.2 Hz, 1H), 7.43 (dd, J=8.3, 2.3 Hz, 1H), 7.34 (s, 1H), 7.23 (s, 1H), 6.87 (d, J=8.1 Hz, 1H), 2.22-2.17 (m, 6H), 2.11-2.05 (m, 3H), 1.83-1.79 (m, 6H); $^{13}$C NMR (125 MHz, CD$_3$CN) δ 168.03, 156.86, 155.13, 153.73, 142.15, 137.68, 133.00, 129.59, 126.92, 126.69, 126.44, 124.74, 111.14, 109.72, 108.71, 41.07, 37.75, 30.07; HRMS Accurate mass (ES+): Found 431.1856, C$_{27}$H$_{27}$O$_5$(M+H+) requires 431.1859.

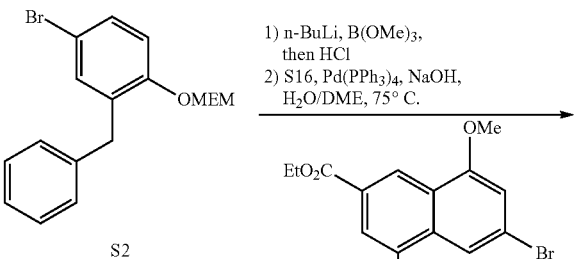

Ethyl 6-(3-benzyl-4-((2-methoxyethoxy)methoxy) phenyl)-4-hydroxy-8-methoxy-2-naphthoate (S18)

Following general procedure A, bromide S2 (60 mg, 0.171 mmol) and naphthyl bromide S16 (50 mg, 0.136 mmol) yielded the title compound as a clear oil (66 mg, 92% yield with respect to S16). $^1$H NMR (500 MHz, CDCl$_3$) δ 8.72 (s, 1H), 8.11 (s, 1H), 7.80 (s, 1H), 7.70 (s, 2H), 7.45-7.36 (m, 5H), 7.31 (s, 1H), 7.18 (s, 1H), 6.98 (br s, 1H), 5.44 (s, 2H), 4.61 (dd, J=13.9, 6.8 Hz, 2H), 4.23 (s, 2H), 4.20 (s, 3H), 3.81 (s, 2H), 3.65 (s, 2H), 3.53 (s, 3H), 1.60 (t, J=6.9 Hz, 3H); $^{13}$C NMR (125 MHz, CDCl$_3$) δ 167.73, 156.74, 154.97, 152.42, 141.03, 140.46, 134.80, 130.48, 129.92, 128.85, 128.34, 126.74, 126.54, 125.93, 125.04, 117.50, 114.33, 111.85, 108.96, 104.82, 93.14, 71.69, 67.62, 61.46, 59.08, 55.74, 36.69, 29.82, 14.50; HRMS Accurate mass (ES+): Found 517.2227, C$_{31}$H$_{33}$O$_7$ (M+H+) requires 517.2226.

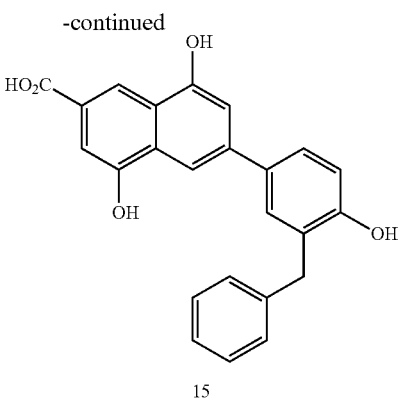

6-(3-benzyl-4-hydroxyphenyl)-4,8-dihydroxy-2-naphthoic acid (15)

Following general procedure C, MEM ether S18 (20 mg, 0.039 mmol) yielded the title compound as an orange oil (3.0 mg, 20% yield). ¹H NMR (400 MHz, CD₃CN) δ 8.36 (s, 1H), 7.82 (s, 1H), 7.76 (br s, 1H), 7.52 (d, J=2.4 Hz, 1H), 7.47 (dd, J=8.3, 2.4 Hz, 1H), 7.34 (d, J=1.4 Hz, 1H), 7.33-7.25 (m, 5H), 7.22-7.11 (m, 2H), 6.94 (d, J=8.3 Hz, 1H), 4.02 (s, 2H); ¹³C NMR (125 MHz, CD₃CN) δ 168.08, 155.74, 155.12, 153.74, 142.28, 141.51, 133.36, 130.48, 129.67, 129.52, 129.30, 127.26, 127.02, 126.84, 124.79, 117.86, 116.62, 111.23, 109.59, 108.71, 36.48; HRMS Accurate mass (ES+): Found 387.1241, C₂₄H₁₉O₅(M+H+) requires 387.1233.

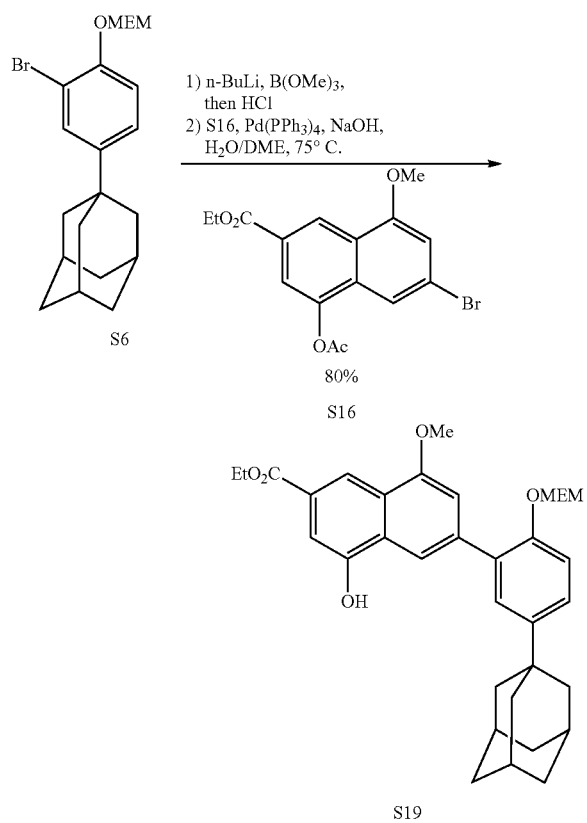

Ethyl 6-(5-(adamantan-1-yl)-2-((2-methoxyethoxy)methoxy)phenyl)-4-hydroxy-8-methoxy-2-naphthoate (S19)

Following general procedure A, bromide S6 (68 mg, 0.172 mmol) and naphthyl bromide S16 (53 mg, 0.143 mmol) yielded the title compound as a white foam (64 mg, 80% yield with respect to S16). ¹H NMR (500 MHz, CDCl₃) δ 8.60 (s, 1H), 7.89 (s, 1H), 7.60 (s, 1H), 7.42 (d, J=2.2 Hz, 1H), 7.33 (dd, J=8.6, 2.1 Hz, 1H), 7.22 (d, J=8.7 Hz, 1H), 7.10 (s, 1H), 6.49 (br s, 1H), 5.22 (s, 2H), 4.46 (q, J=7.0 Hz, 2H), 4.03 (s, 3H), 3.75-3.70 (m, 2H), 3.52-3.48 (m, 2H), 3.34 (s, 3H), 2.10 (s, 3H), 1.94 (s, 6H), 1.77 (q, J=12.2 Hz, 6H), 1.46 (t, J=7.1 Hz, 3H); ¹³C NMR (125 MHz, CDCl₃) δ 167.74, 155.67, 152.48, 152.09, 145.57, 139.24, 131.66, 128.06, 127.79, 126.72, 125.54, 125.07, 117.40, 115.65, 114.67, 108.74, 107.83, 94.42, 71.65, 67.84, 61.41, 59.02, 55.73, 43.40, 36.84, 35.85, 29.05, 14.49; HRMS Accurate mass (ES+): Found 583.2653, C₃₄H₄₀O₇Na (M+Na+) requires 583.2672.

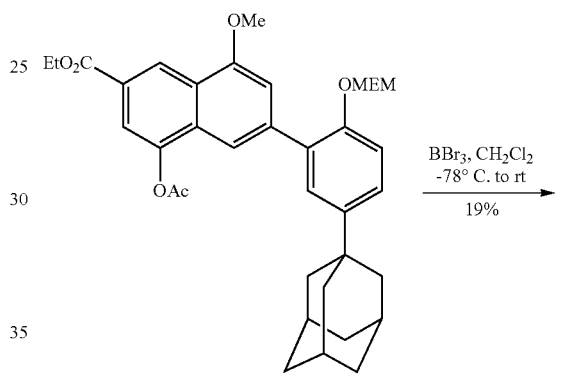

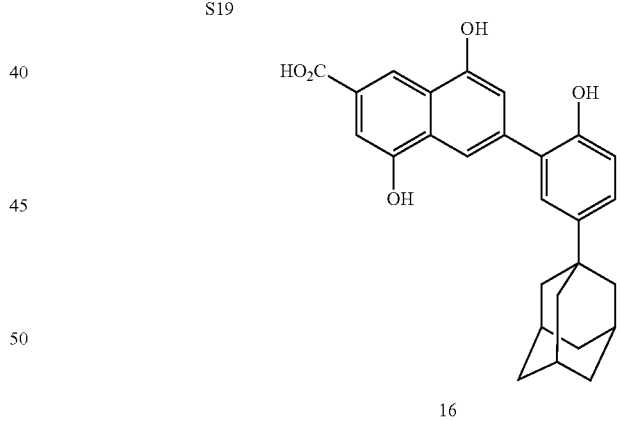

6-(5-(adamantan-1-yl)-2-hydroxyphenyl)-4,8-dihydroxy-2-naphthoic acid (16)

Following general procedure C, MEM ether S19 (19 mg, 0.034 mmol) yielded the title compound as an orange oil (2.8 mg, 19% yield). ¹H NMR (500 MHz, CD₃CN) δ 8.40 (s, 1H), 7.80 (s, 1H), 7.74 (br s, 1H), 7.35 (s, 2H), 7.29-7.22 (m, 1H), 7.18 (s, 1H), 6.90 (d, J=8.4 Hz, 1H), 6.74 (br s, 1H), 2.10-2.03 (m, 3H), 1.96-1.89 (m, 6H overlaps with CD₃CN signal), 1.83-1.75 (m, 6H); ¹³C NMR (125 MHz, CD₃CN) δ 168.06, 154.35, 153.77, 152.45, 144.59, 139.97, 129.19, 128.52, 128.12, 127.20, 126.50, 124.90, 117.85, 116.84, 114.63, 112.47, 108.54, 44.03, 37.35, 30.02; HRMS Accurate mass (ES+): Found 453.1673, $C_{27}H_{26}O_5Na$ (M+Na+) requires 453.1678.

Example 2—Biological Activity of Exemplified Compounds

Antibacterial activity of 16 analogs is examined in FIG. 4. Analog 2, having a less polar primary alcohol substituted for a carboxylic acid, shows a similar level of anti-persister activity as CD437 but exhibits significantly reduced hemolytic activity, cytotoxicity, and anticancer activity (FIG. 2, 4). Replacement of the phenol group of Analog 2, which has a methoxy group (Analog 6 in FIG. 4a), eliminated both antimicrobial activity and membrane permeability (FIG. 4b). These results support the conclusion that two polar branch groups, for example a carboxylic group and a hydroxyl group, facilitate membrane penetration of the retinoids.

Analog 10, the ortho-phenol derivative, was >30-fold less active that the parent compound (FIG. 4).

Analog 9, which has a benzyl group substituted for the adamantane group, has a 2-fold higher MIC (2 μg/ml) against growing MRSA MW2 cells (FIG. 4), as well as against MRSA persisters (16 μg/ml; FIG. 5c). Importantly, Analog 9 demonstrated similar hemolytic activity and hepatotoxicity as CD437 (FIG. 5).

Figure 4A:
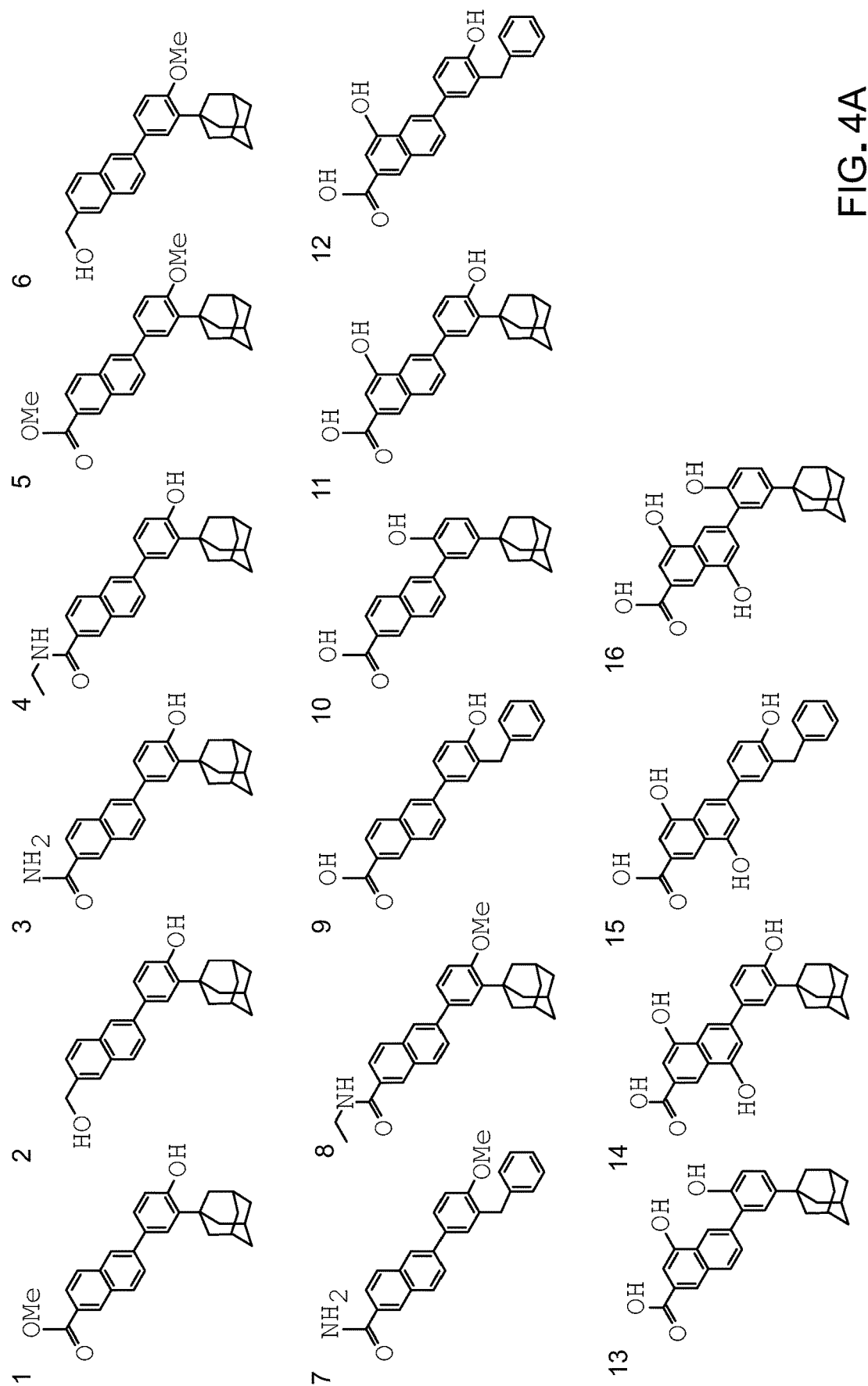
Figure 4B:
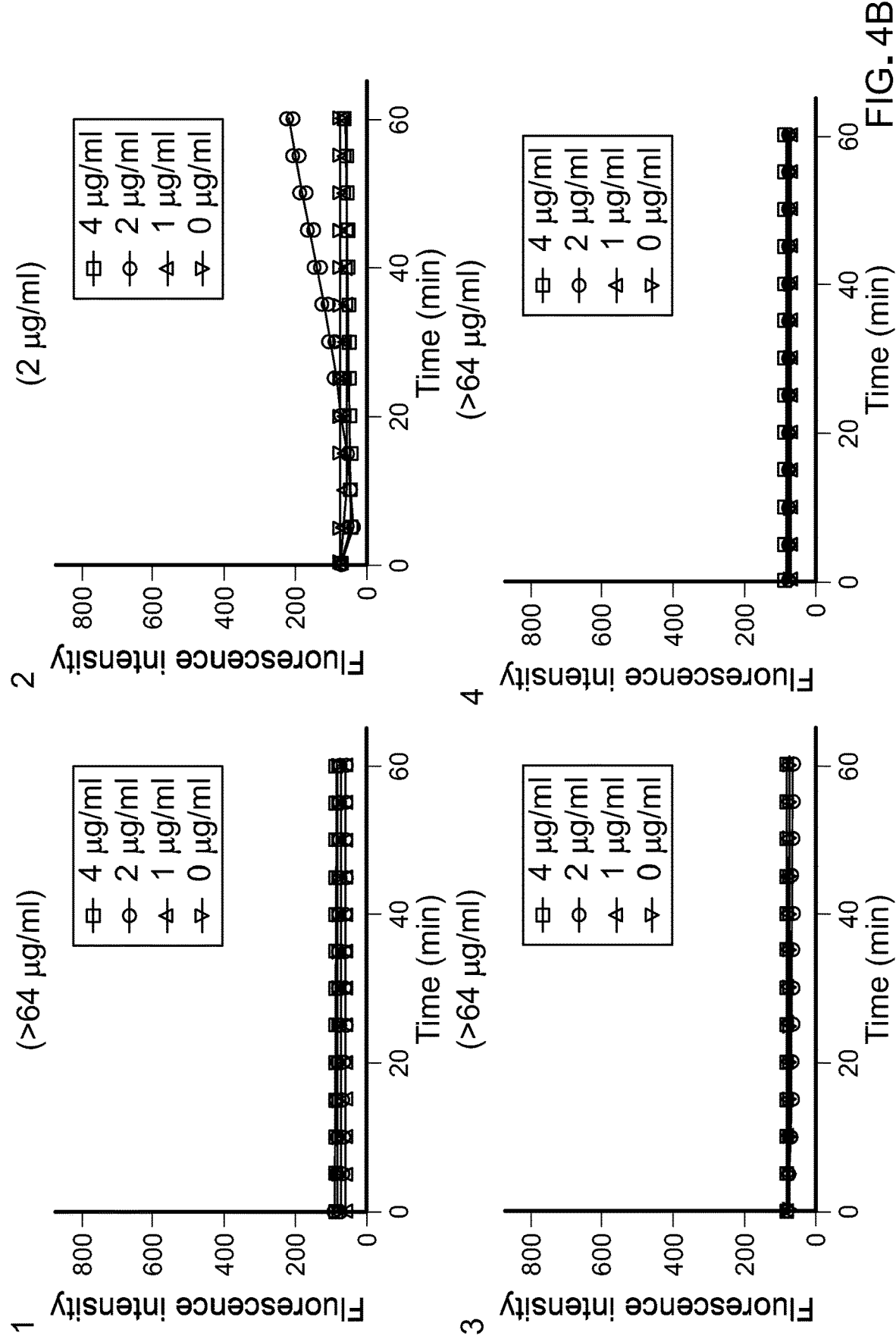
Figure 4B:
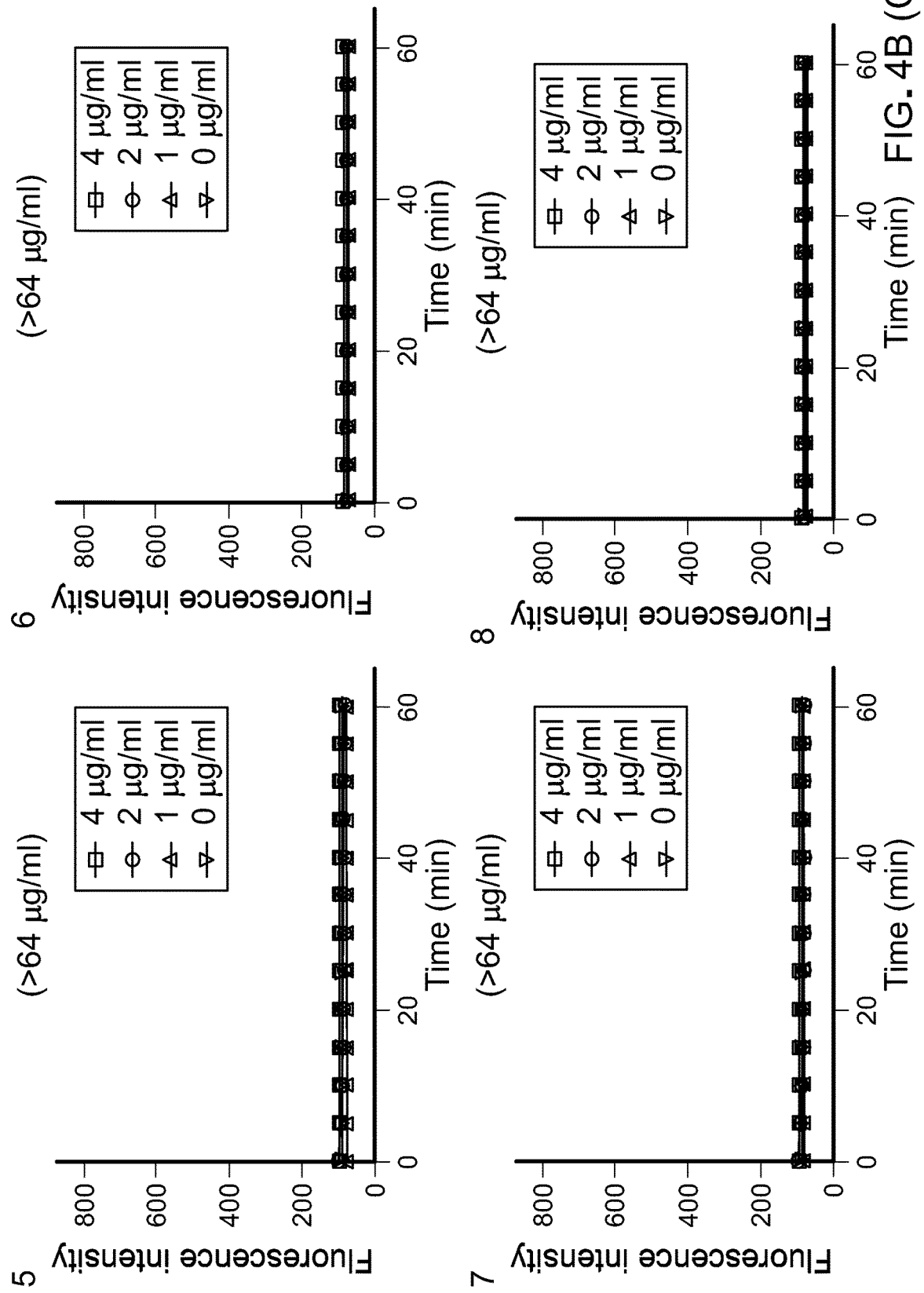
Figure 4B:
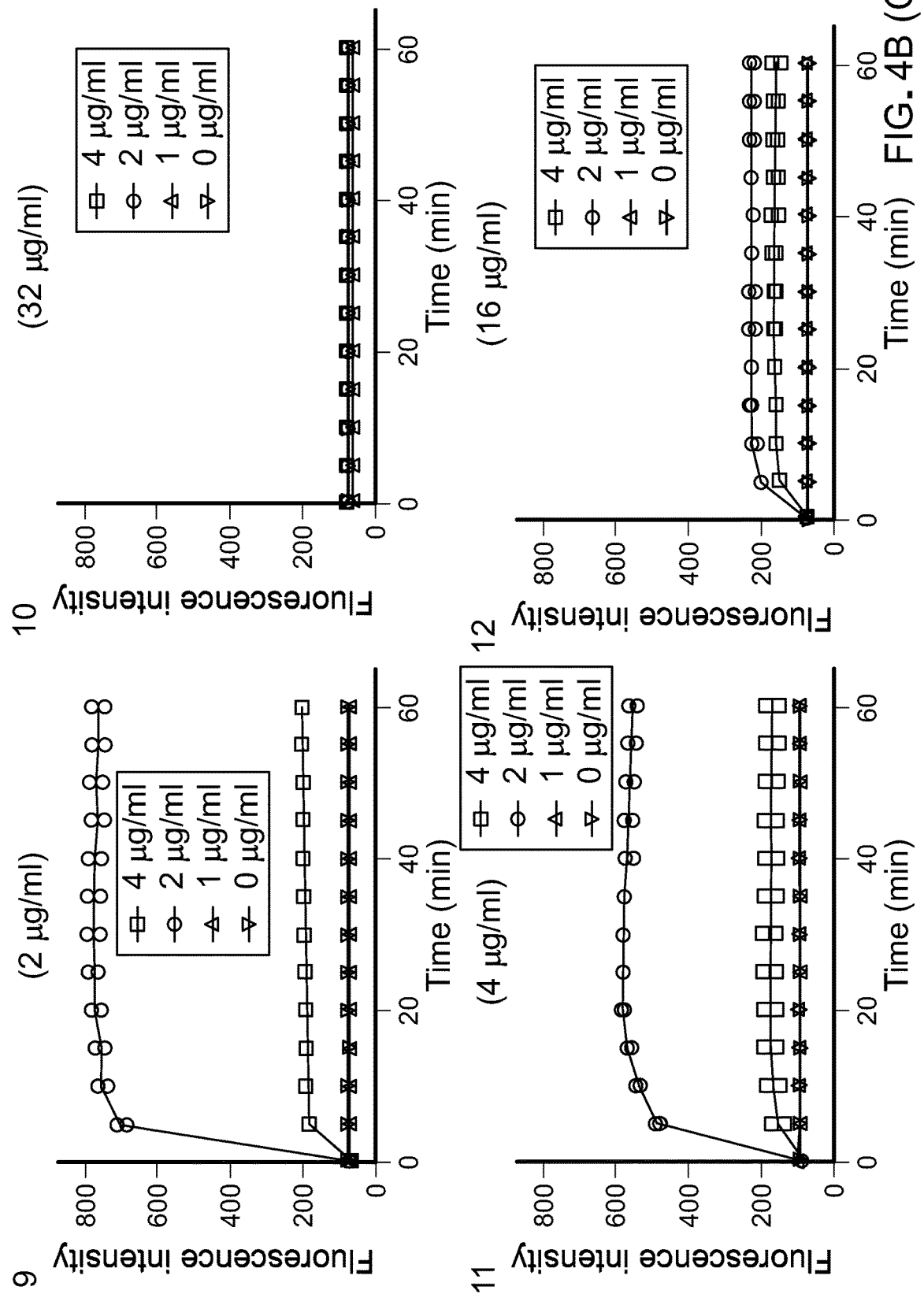
Figure 4B:
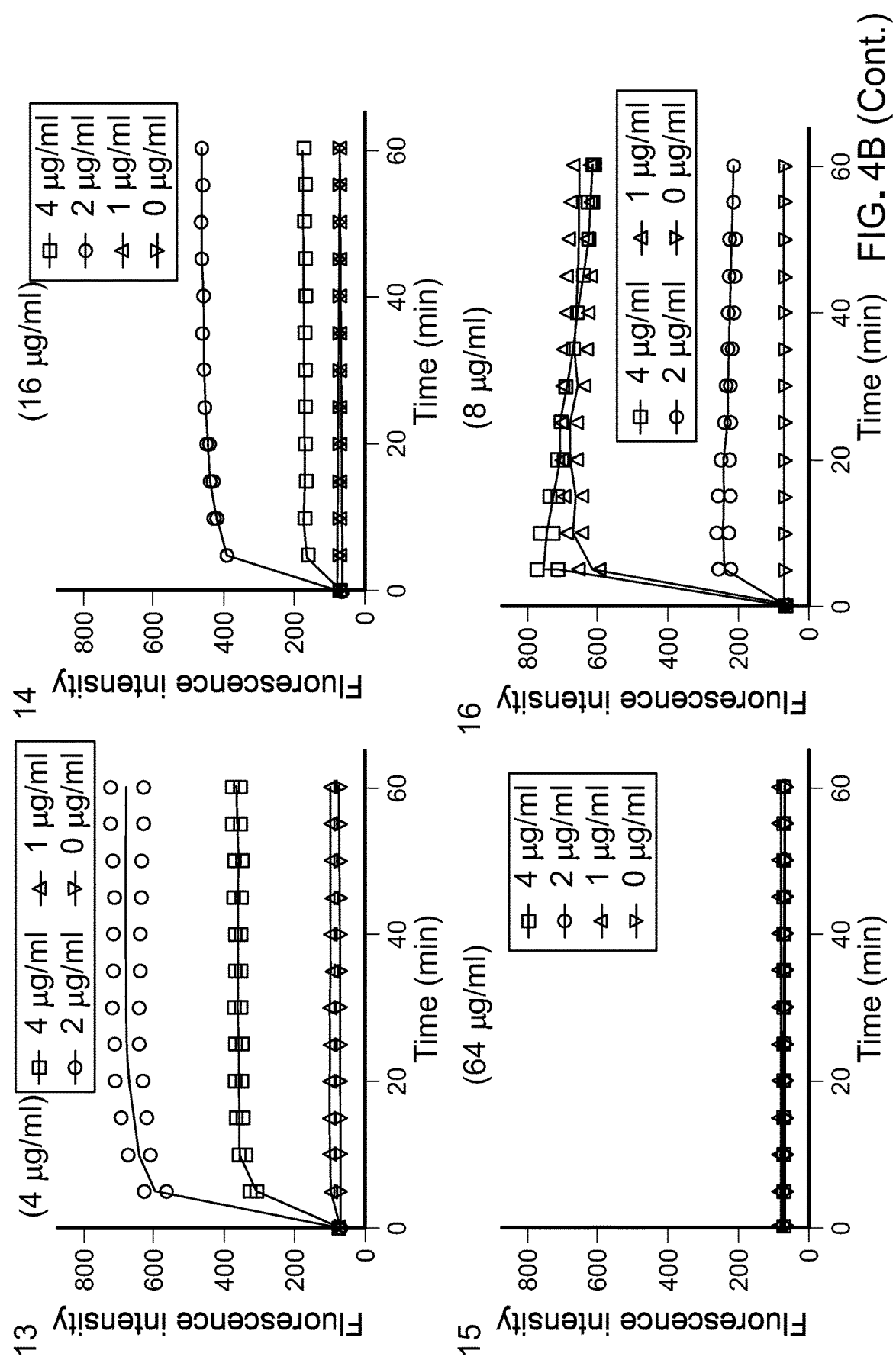

Analog 3 in FIG. 4a is an amide. Like carboxylic acids, amides form hydrogen bonds. However, the nitrogen in the amide is known to have a higher negative charge than the carboxylic acid's oxygen because the nitrogen in the primary resonance form of the amide attracts shared electrons from two N—H bonds and is consistent with calculations of partial atomic charges (FIG. 6a). Analog 3 exhibited comparatively low antimicrobial activity (FIG. 4b).

MD simulations of Analog 3 with lipid bilayers consisting of 7DOPC/3DOPG revealed that Analog 3 could not penetrate, and instead was repelled away from the membrane due to electrostatic repulsion (FIG. 6b), with a high energy barrier and an unfavorable transfer energy (FIG. 6c).

Analog 11, which has an additional hydroxyl group, showed a 4-fold decrease in antimicrobial activity (MIC 4 μg/ml vs. 1 μg/ml for CD437).

The MIC of Analog 14, which has two additional hydroxyl groups, was 16 μg/ml, which is another 4-fold decrease in antimicrobial activity.

Analog 12, has one more hydroxyl group than Analog 9, and Analog 15, which has two more hydroxyl groups than Analog 9 (FIG. 4). The MD simulations using the 7DOPC/3DOPG lipid bilayers showed that the attachment energies of Analogs 11 and 14 are −5.29 $k_BT$, and −6.82 $k_BT$, respectively, which are better than the −3.61 $k_BT$ of CD437 (FIG. 6e). However, Analogs 11 and 14 have higher transfer energies of −2.79 $k_BT$ and −1.58 $k_BT$, respectively, than the −8.92 $k_BT$ of CD437 (FIG. 6e), and their energy barriers are also higher (3.36 $k_BT$ for Analog 11, and 4.32 $k_BT$ for Analog 14 vs. 1.42 $k_BT$ for CD437 in FIG. 6e). These results demonstrate that the addition of hydroxyl groups on CD437 can provide stronger binding to lipid head groups, but the increased hydrophilicity may prevent penetration deep into hydrophobic core of membranes.

Although Analog 13, which has an additional hydroxyl group on Analog 10, showed an 8-fold increase in antimicrobial activity (4 μg/ml for Analog 13 vs. 32 g/ml for Analog 10), the attachment of one more hydroxyl group on Analog 13 led to a decrease in antimicrobial activity (8 μg/ml for Analog 16 vs. 4 μg/ml for Analog 13 in FIG. 4).

Example 3—Antibacterial Activity of Analog 2

Figure 3A:
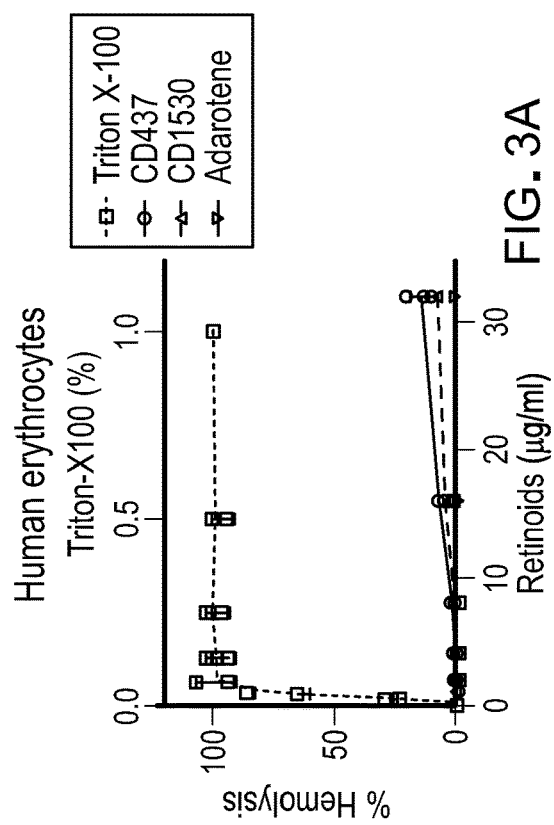
Figure 3B:
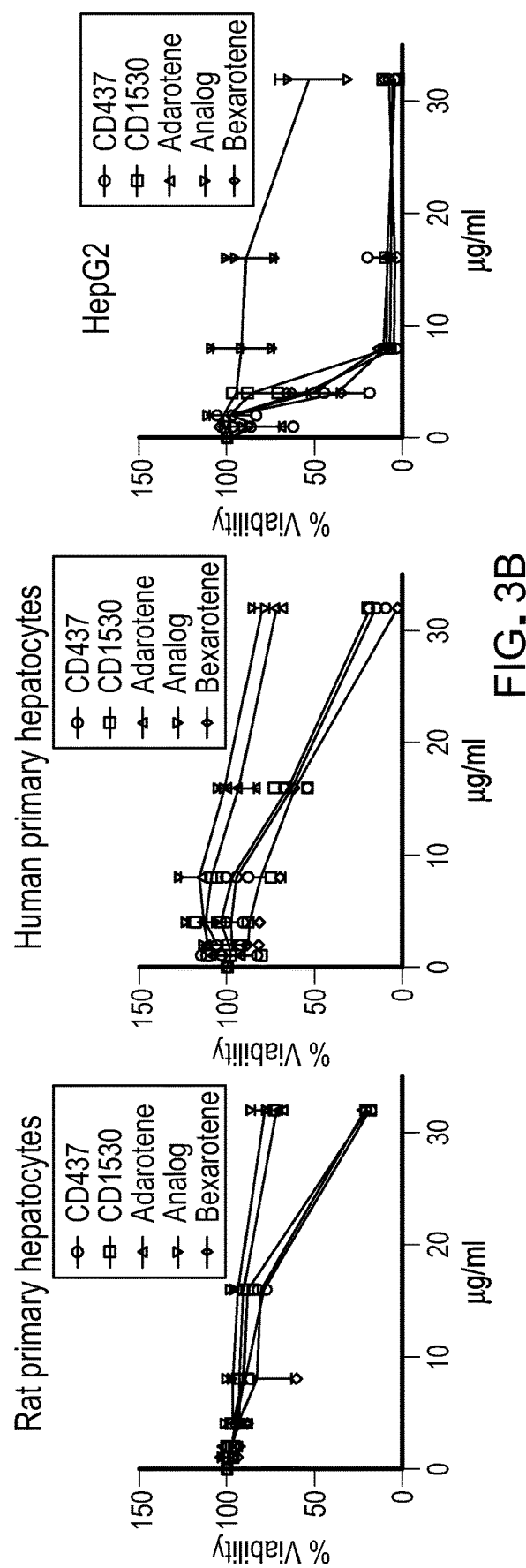
Figure 3B:
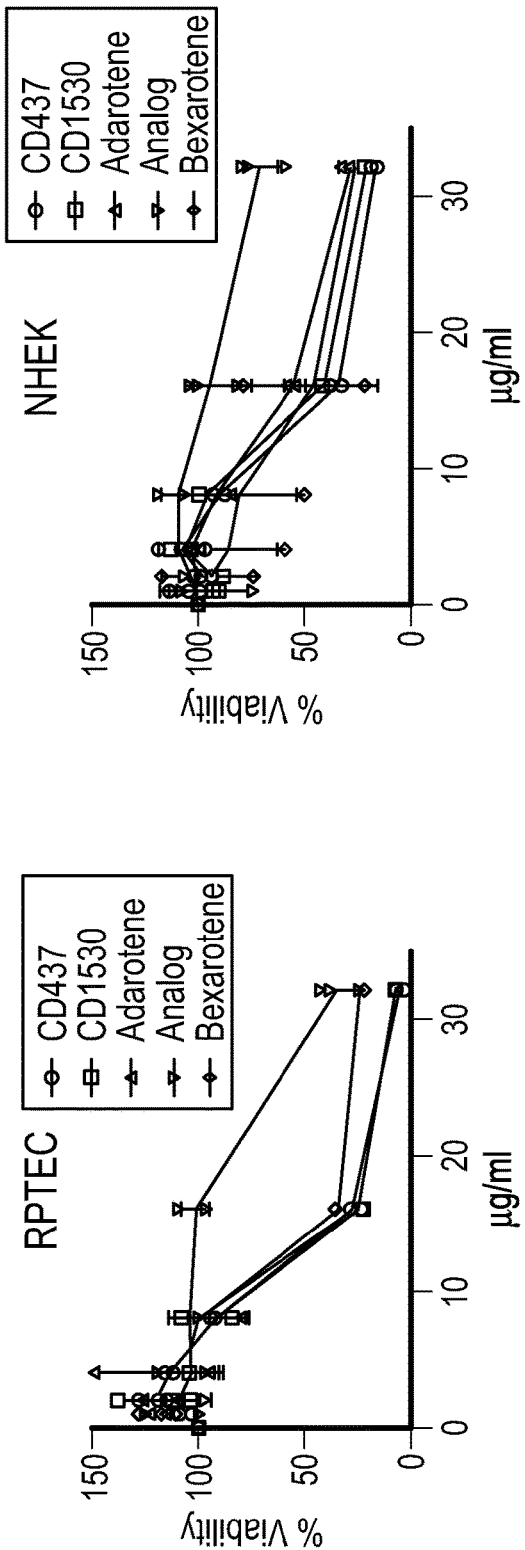
Figure 3C:
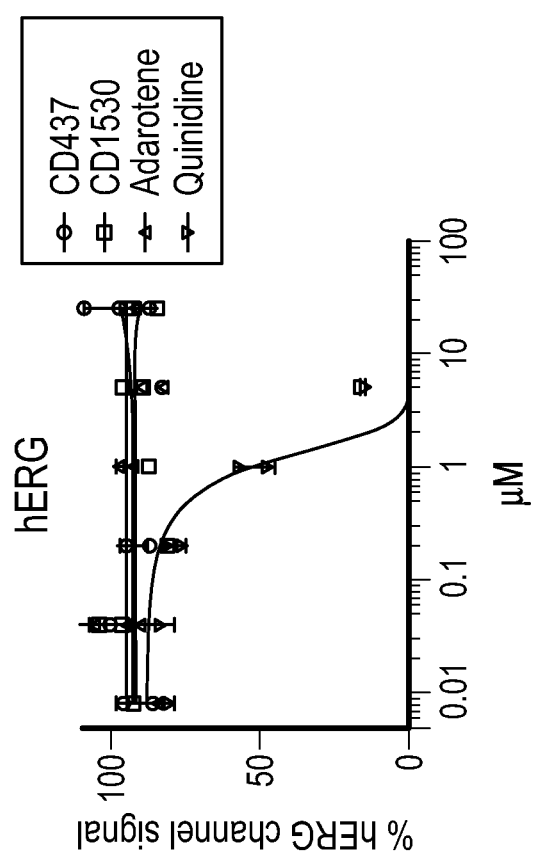

Analog 2 retained bacterial activity against MRSA persisters (FIGS. 2 a,b), but showed significantly less hemolytic activity (HC50>32 μg/ml, FIG. 5a) and cytotoxicity in a panel of human cell lines ($LC_{50}$>31 μg/ml) th an CD437 (FIG. 2c, FIG. 3b). Analog 2 also showed significantly reduced activity to human hepatoma HepG2 cells with an $LC_{50}$>32 μg/ml (FIG. 2c).

Figure 5B:
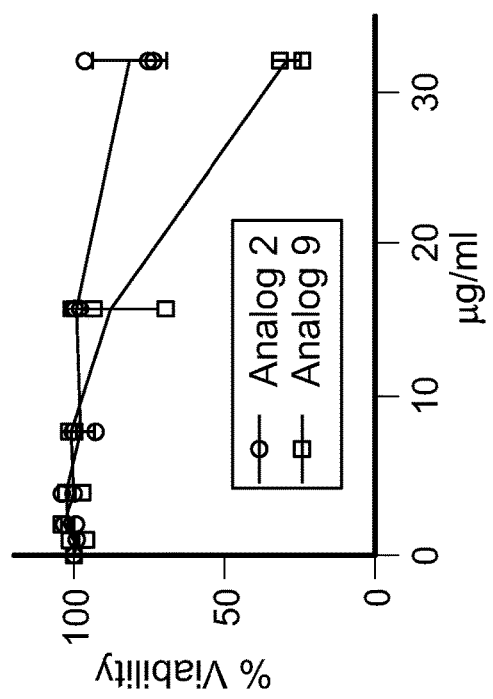
Figure 5A:
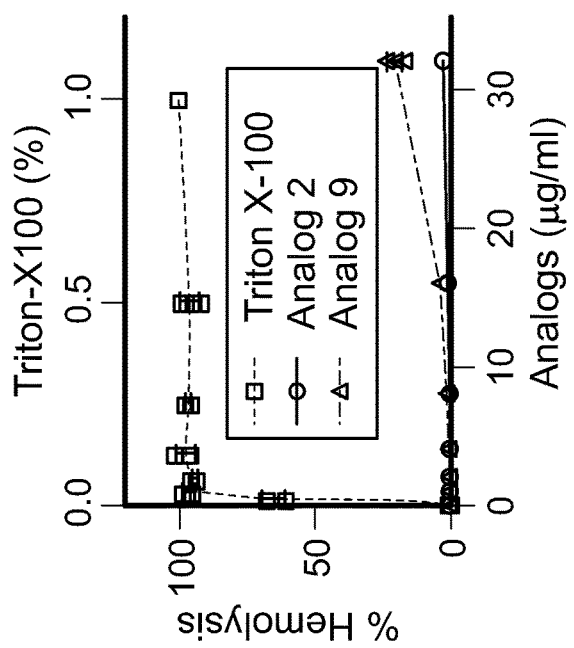
Figure 5C:
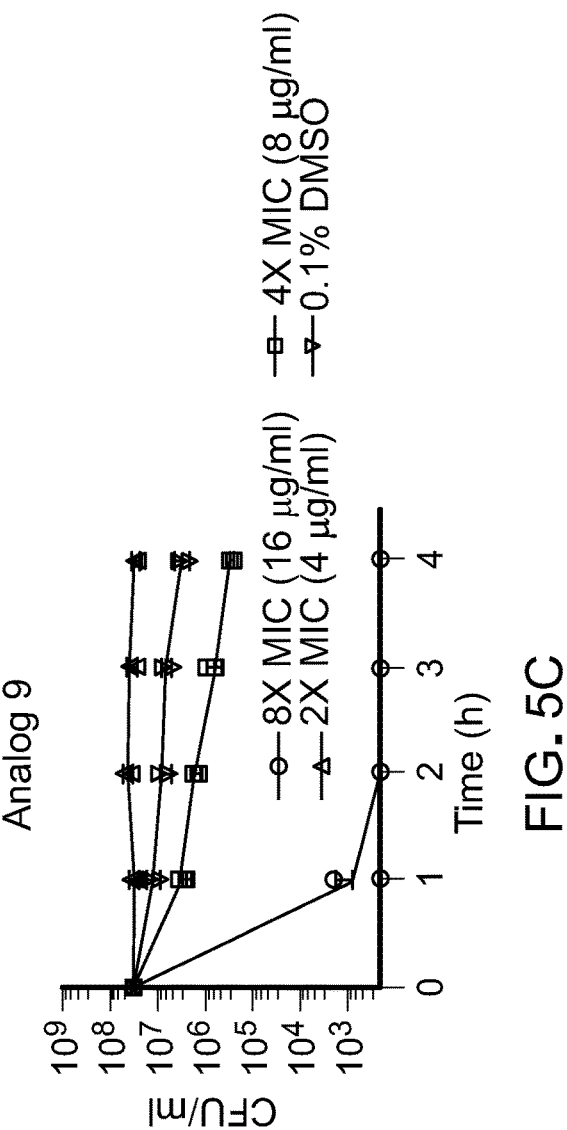
Figure 5D:
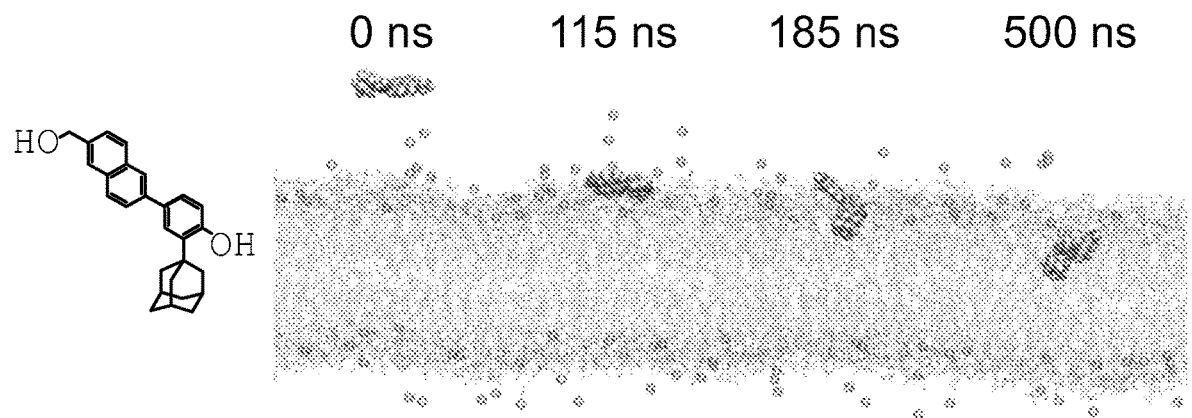
Figure 5E:
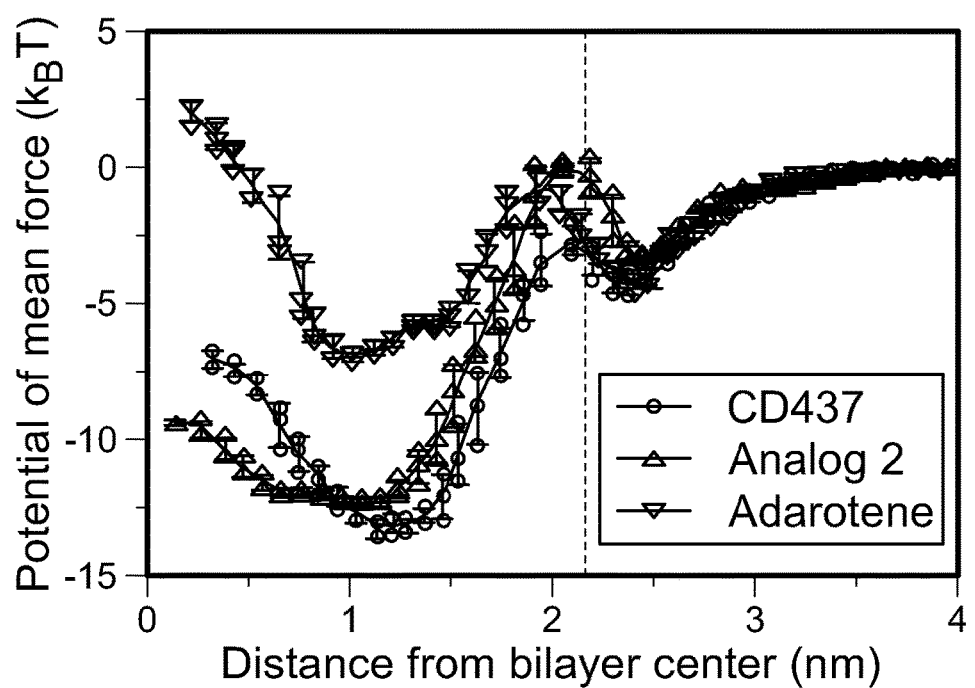

Analog 2 also exhibited favorable pharmacokinetic profiles after intraperitoneal administration of a single dose of 20 mg/kg, with a maximum plasma concentration of ~10 μg/ml and an elimination half-life of 4.5 h (FIG. 5f). In contrast, adarotene is excreted rapidly. Analog 2 showed no detectable hepatic or renal toxicity in mice up to an intraperitoneal dose of 80 mg/kg (the highest tested dose) every 12 h for 3 days (FIG. 5g).

Example 4—Combination of Analog 2 and Gentamicin

Combination of Analog 2+gentamicin in a mouse deep-seated thigh MRSA infection model was evaluated. This model mimics human deep-seated chronic infections. Consistent with previous findings, the combination of vancomycin and gentamicin did not significantly reduce MRSA abundance (FIG. 2d), even though MW2 is sensitive to both antibiotics, suggesting that the bacterial cells in this infection model are persisters. As shown in FIG. 2d, 80 mg/kg Analog 2 alone led to ~1-log decrease (p<0.001), and 40 or 80 mg/kg Analog 2 in combination with 30 mg/kg gentamicin resulted in ~1-log (p<0.001) and ~2-log decreases (p<0.001) in bacterial burden, respectively.

Example 5—Retinoids Selectively Disrupt Bacterial Membrane

MD simulations revealed that Analog 2 penetrates membrane lipid bilayers with similar energy profiles as CD437 (FIGS. 5 d,e), further establishing the extent of membrane penetration inferred from MD simulations correlates with antimicrobial activity.

The result of bacterial membrane penetration experiments by analog 2 are shown in FIG. 7.

Example 6—Antibacterial Activity of Tested Compounds Against *P. acnes*

Retinoids CD437 and compound 2 (but not adapalene) inhibit the growth of *Cutibacterium (Propionibacterium) acnes* (FIG. 11). Using standard protocols, it was found that the MIC ranged from 2-8 μg/mL (FIG. 8) and that the mode of action is by increasing permeability of the bacterial membrane (FIGS. 12 and 13). More specifically, uptake of SYTOX Green by *Cutibacterium (Propionibacterium) acnes* cells treated with retinoids CD437 and Analog 2 increased, indicating higher permeability (FIG. 12; individual data points (n=3 biologically independent samples) and means are shown). Moreover, the morphology of bacteria was altered and elongated further confirming that the retinoids CD437 and compound 2 affect the membrane of *Cutibacterium (Propionibacterium) acnes* bacteria.

REFERENCES

1. Tong, S. Y. C., Davis, J. S., Eichenberger, E., Holland, T. L. & Fowler, V. G. *Staphylococcus aureus* infections:

1. epidemiology, pathophysiology, clinical manifestations, and management. *Clin. Microbiol. Rev.* 28, 603-661 (2015).
2. Allison, K. R., Brynildsen, M. P. & Collins, J. J. Metabolite-enabled eradication of bacterial persisters by aminoglycosides. *Nature* 473, 216-220 (2011).
3. Conlon, B. P. et al. Activated ClpP kills persisters and eradicates a chronic biofilm infection. *Nature* 503, 365-370 (2013).
4. Lehar, S. M. et al. Novel antibody-antibiotic conjugate eliminates intracellular *S. aureus*. *Nature* 527, 323-328 (2015).
5. Davies, J. & Davies, D. Origins and evolution of antibiotic resistance. *Microbiol Mol Biol Rev* 74, 417-433 (2010).
6. Lew, D. P. & Waldvogel, F. A. Osteomyelitis. *The Lancet* 364, 369-379 (2004).
7. Baddour, L. M. et al. Infective endocarditis in adults: diagnosis, antimicrobial therapy, and management of complications: a scientific statement for healthcare professionals from the American Heart Association. *Circulation* 132, 1435-1486 (2015).
8. Rajamuthiah, R. et al. Whole animal automated platform for drug discovery against multi-drug resistant *Staphylococcus aureus*. *PLoS ONE* 9, e89189 (2014).
9. Altucci, L., Leibowitz, M. D., Ogilvie, K. M., de Lera, A. R. & Gronemeyer, H. RAR and RXR modulation in cancer and metabolic disease. *Nat. Rev. Drug Discov.* 6, 793-810 (2007).
10. Valli, C. et al. Atypical retinoids ST1926 and CD437 are S-phase-specific agents causing DNA double-strand breaks: significance for the cytotoxic and antiproliferative activity. *Mol. Cancer Ther.* 7, 2941-2954 (2008).
11. Shimono, K. et al. Potent inhibition of heterotopic ossification by nuclear retinoic acid receptor-γ agonists. *Nat. Med.* 17, 454-460 (2011).
12. Tang, X.-H. et al. Combination of bexarotene and the retinoid CD1530 reduces murine oral-cavity carcinogenesis induced by the carcinogen 4-nitroquinoline 1-oxide. *Proc. Natl. Acad. Sci. U.S.A* 111, 8907-8912 (2014).
13. Irby, C. E., Yentzer, B. A. & Feldman, S. R. A review of adapalene in the treatment of acne vulgaris. *J. Adolesc. Health* 43, 421-424 (2008).
14. Fey, P. D. et al. A genetic resource for rapid and comprehensive phenotype screening of nonessential *Staphylococcus aureus* genes. *MBio* 4, e00537-12-e 00537-12 (2013).
15. Meehl, M., Herbert, S., Götz, F. & Cheung, A. Interaction of the GraRS two-component system with the VraFG ABC transporter to support vancomycin-intermediate resistance in *Staphylococcus aureus*. *Antimicrob. Agents Chemother.* 51, 2679-2689 (2007).
16. Yang, S.-J. et al. The *Staphylococcus aureus* two-component regulatory system, GraRS, senses and confers resistance to selected cationic antimicrobial peptides. *Infect. Immun.* 80, 74-81 (2012).
17. Elbaz, M. & Ben-Yehuda, S. The metabolic enzyme ManA reveals a link between cell wall integrity and chromosome morphology. *PLoS Genet.* 6, e1001119 (2010).
18. Falord, M., Mäder, U., Hiron, A., Débarbouillé, M. & Msadek, T. Investigation of the *Staphylococcus aureus* GraSR regulon reveals novel links to virulence, stress response and cell wall signal transduction pathways. *PLoS ONE* 6, e21323 (2011).
19. Göhring, N. et al. New role of the disulfide stress effector YjbH in β-lactam susceptibility of *Staphylococcus aureus*. *Antimicrob. Agents Chemother.* 55, 5452-5458 (2011).
20. Friedrich, C. L., Moyles, D., Beveridge, T. J. & Hancock, R. E. Antibacterial action of structurally diverse cationic peptides on Gram-positive bacteria. *Antimicrob. Agents Chemother.* 44, 2086-2092 (2000).
21. Chen, Y.-F., Sun, T.-L., Sun, Y. & Huang, H. W. Interaction of daptomycin with lipid bilayers: a lipid extracting effect. *Biochemistry* 53, 5384-5392 (2014).
22. Ganewatta, M. S. et al. Bio-inspired resin acid-derived materials as anti-bacterial resistance agents with unexpected activities. *Chem Sci* 5, 2011-2016 (2014).
23. Piggot, T. J., Holdbrook, D. A. & Khalid, S. Electroporation of the *E. coli* and *S. aureus* membranes: molecular dynamics simulations of complex bacterial membranes. *J Phys Chem B* 115, 13381-13388 (2011).
24. Hurdle, J. G., O'Neill, A. J., Chopra, I. & Lee, R. E. Targeting bacterial membrane function: an underexploited mechanism for treating persistent infections. *Nat. Rev. Microbiol.* 9, 62-75 (2011).
25. Liu, C. et al. Clinical practice guidelines by the Infectious Diseases Society of America for the treatment of methicillin-resistant *Staphylococcus aureus* infections in adults and children. *Clin. Infect. Dis.* 52, e18-e55 (2011).
26. Cosgrove, S. E. et al. Initial low-dose gentamicin for *Staphylococcus aureus* bacteremia and endocarditis is nephrotoxic. *Clin. Infect. Dis.* 48, 713-721 (2009).
27. Buchholtz, K., Larsen, C. T., Hassager, C. & Bruun, N. E. Severity of gentamicin's nephrotoxic effect on patients with infective endocarditis: a prospective observational cohort study of 373 patients. *Clin. Infect. Dis.* 48, 65-71 (2009).
28. Cui, P. et al. Disruption of membrane by colistin kills uropathogenic *Escherichia coli* persisters and enhances killing of other antibiotics. *Antimicrob. Agents Chemother.* 60, 6867-6871 (2016).
29. Rajamuthiah, R. et al. A defensin from the model beetle *Tribolium castaneum* acts synergistically with telavancin and daptomycin against multidrug resistant *Staphylococcus aureus*. *PLoS ONE* 10, e0128576 (2015).
30. Farha, M. A., Verschoor, C. P., Bowdish, D. & Brown, E. D. Collapsing the proton motive force to identify synergistic combinations against *Staphylococcus aureus*. *Chemistry &Biology* 20, 1168-1178 (2013).
31. Baba, T. et al. Genome and virulence determinants of high virulence community-acquired MRSA. *Lancet* 359, 1819-1827 (2002).
32. Weigel, L. M. et al. Genetic analysis of a high-level vancomycin-resistant isolate of *Staphylococcus aureus*. *Science* 302, 1569-1571 (2003).
33. Kim, W. et al. NH125 kills methicillin-resistant *Staphylococcus aureus* persisters by lipid bilayer disruption. *Future Med. Chem.* 8, 257-269 (2016).
34. Garsin, D. A. et al. A simple model host for identifying Gram-positive virulence factors. *Proc. Natl. Acad. Sci. U.S.A* 98, 10892-10897 (2001).
35. Rice, L. B. et al. *Enterococcus faecium* low-affinity pbp5 is a transferable determinant. *Antimicrob. Agents Chemother.* 49, 5007-5012 (2005).
36. Carias, L. L., Rudin, S. D., Donskey, C. J. & Rice, L. B. Genetic linkage and cotransfer of a novel, vanB-containing transposon (Tn5382) and a low-affinity penicillin-binding protein 5 gene in a clinical vancomycin-resistant *Enterococcus faecium* isolate. *J. Bacteriol.* 180, 4426-4434 (1998).

37. Garcia-Solache, M. & Rice, L. B. Genome sequence of the multiantibiotic-resistant *Enterococcus faecium* Strain C68 and insights on the pLRM23 colonization plasmid. *Genome Announc.* 4, e01719-15 (2016).
38. Thorisdottir, A. S. et al. IS6770, an enterococcal insertion-like sequence useful for determining the clonal relationship of clinical enterococcal isolates. *J. Infect. Dis.* 170, 1539-1548 (1994).
39. Smith, M. G. et al. New insights into *Acinetobacter baumannii* pathogenesis revealed by high-density pyrosequencing and transposon mutagenesis. *Genes Dev.* 21, 601-614 (2007).
40. Rahme, L. G. et al. Common virulence factors for bacterial pathogenicity in plants and animals. *Science* 268, 1899-1902 (1995).
41. Tan, M. W., Mahajan-Miklos, S. & Ausubel, F. M. Killing of *Caenorhabditis elegans* by *Pseudomonas aeruginosa* used to model mammalian bacterial pathogenesis. *Proc. Natl. Acad. Sci. U.S.A* 96, 715-720 (1999).
42. Beanan, M. J. & Strome, S. Characterization of a germ-line proliferation mutation in *C. elegans*. *Development* 116, 755-766 (1992).
43. Hino, M. T. et al. SEK-1 MAPKK mediates Ca2+ signaling to determine neuronal asymmetric development in *Caenorhabditis elegans*. *EMBO reports* 3, 56-62 (2002).
44. Moy, T. I. et al. High-throughput screen for novel antimicrobials using a whole animal infection model. *ACS Chem. Biol.* 4, 527-533 (2009).
45. Kamentsky, L. et al. Improved structure, function and compatibility for CellProfiler: modular high-throughput image analysis software. *Bioinformatics* 27, 1179-1180 (2011).
46. Clinical and Laboratory Standards Institute. *Methods for dilution antimicrobial susceptibility tests for bacteria that grow aerobically; approved standard-ninth edition. CLSI document* M0 7-A9. 1-88 (2012).
47. Keren, I., Kaldalu, N., Spoering, A., Wang, Y. & Lewis, K. Persister cells and tolerance to antimicrobials. *FEMS Microbiol. Lett.* 230, 13-18 (2004).
48. Conlon, B. P. et al. Persister formation in *Staphylococcus aureus* is associated with ATP depletion. *Nature Microbiology* 1, 16051 (2016).
49. Kim, W. et al. Identification of an antimicrobial agent effective against methicillin-resistant *Staphylococcus aureus* persisters using a fluorescence-based screening strategy. *PLoS ONE* 10, e0127640 (2015).
50. Cassat, J. E., Lee, C. Y. & Smeltzer, M. S. Investigation of biofilm formation in clinical isolates of *Staphylococcus aureus*. *Methods Mol. Biol.* 391, 127-144 (2007).
51. Friedman, L., Alder, J. D. & Silverman, J. A. Genetic changes that correlate with reduced susceptibility to daptomycin in *Staphylococcus aureus*. *Antimicrob. Agents Chemother.* 50, 2137-2145 (2006).
52. Sharma-Kuinkel, B. K. et al. The *Staphylococcus aureus* LytSR two-component regulatory system affects biofilm formation. *J. Bacteriol.* 191, 4767-4775 (2009).
53. Monk, I. R., Shah, I. M., Xu, M., Tan, M.-W. & Foster, T. J. Transforming the untransformable: application of direct transformation to manipulate genetically *Staphylococcus aureus* and *Staphylococcus epidermidis*. *MBio* 3, e00277-11-e 00277-11 (2012).
54. Grosser, M. R. & Richardson, A. R. in *The Genetic Manipulation of Staphylococci* 1373, 51-57 (Springer, 2016).
55. Hess, B., Kutzner, C., van der Spoel, D. & Lindahl, E. GROMACS 4: algorithms for highly efficient, load-balanced, and scalable molecular Simulation. *J. Chem. Theory Comput.* 4, 435-447 (2008).
56. Schmid, N. et al. Definition and testing of the GROMOS force-field versions 54A7 and 54B7. *Eur Biophys J* 40, 843-856 (2011).
57. Malde, A. K. et al. An automated force field topology builder (ATB) and repository: version 1.0. *J. Chem. Theory Comput.* 7, 4026-4037 (2011).
58. Lee, M.-T., Sun, T.-L., Hung, W.-C. & Huang, H. W. Process of inducing pores in membranes by melittin. *Proc. Natl. Acad. Sci. U.S.A* 110, 14243-14248 (2013).
59. Joshi, S., Dewangan, R. P., Yar, M. S., Rawat, D. S. & Pasha, S. N-terminal aromatic tag induced self assembly of tryptophan-arginine rich ultra short sequences and their potent antibacterial activity. *RSC Advances* 5, 68610-68620 (2015).
60. Berger, O., Edholm, O. & Jähnig, F. Molecular dynamics simulations of a fluid bilayer of dipalmitoylphosphatidylcholine at full hydration, constant pressure, and constant temperature. *Biophys. J.* 72, 2002-2013 (1997).
61. Tu, Y. et al. Destructive extraction of phospholipids from *Escherichia coli* membranes by graphene nanosheets. *Nat Nanotechnol* 8, 594-601 (2013).
62. Zhu, W. et al. Nanomechanical mechanism for lipid bilayer damage induced by carbon nanotubes confined in intracellular vesicles. *Proc. Natl. Acad. Sci. U.S.A.* 113, 12374-12379 (2016).
63. Creighton, M. A. et al. Three-dimensional graphene-based microbarriers for controlling release and reactivity in colloidal liquid phases. *ACS Nano* 10, 2268-2276 (2016).
64. Isralewitz, B., Gao, M. & Schulten, K. Steered molecular dynamics and mechanical functions of proteins. *Curr. Opin. Struct. Biol.* 11, 224-230 (2001).
65. Kumar, S., Rosenberg, J. M., Bouzida, D., Swendsen, R. H. & Kollman, P. A. The weighted histogram analysis method for free-energy calculations on biomolecules. I. The method. *J Comput Chem* 13, 1011-1021 (1992).
66. Hub, J. S., de Groot, B. L. & van der Spoel, D. g wham—a free weighted histogram analysis implementation including robust error and autocorrelation estimates. *J. Chem. Theory Comput.* 6, 3713-3720 (2010).
67. Dunn, J. C., Yarmush, M. L., Koebe, H. G. & Tompkins, R. G. Hepatocyte function and extracellular matrix geometry: long-term culture in a sandwich configuration. *FASEB J.* 3, 174-177 (1989).
68. Dunn, J. C., Tompkins, R. G. & Yarmush, M. L. Hepatocytes in collagen sandwich: evidence for transcriptional and translational regulation. *J. Cell Biol.* 116, 1043-1053 (1992).
69. Sharma, N. S., Nagrath, D. & Yarmush, M. L. Metabolic profiling based quantitative evaluation of hepatocellular metabolism in presence of adipocyte derived extracellular matrix. *PLoS ONE* 6, e20137 (2011).
70. Maron, D. M. & Ames, B. N. Revised methods for the *Salmonella* mutagenicity test. *Mutat. Res.* 113, 173-215 (1983).
71. Odds, F. C. Synergy, antagonism, and what the chequerboard puts between them. *J. Antimicrob. Chemother.* 52, 1-1 (2003).
72. Williams, A. B. & Hanson, R. N. Synthesis of substituted asymmetrical biphenyl amino esters as alpha helix mimetics. *Tetrahedron* 68, 5406-5414 (2012).
73. Liu, Z. & Xiang, J. A high yield and pilot-scale process for the preparation of adapalene. *Org Process Res Dev* 10, 285-288 (2006).

74. Tietze, L. F., Panknin, O., Major, F. & Krewer, B. Synthesis of a novel pentagastrin—drug conjugate for a targeted tumor therapy. *Chem Eur J* 14, 2811-2818 (2008).
75. tert-Butyl 3-Carboxyethyl-3-phosphonodiethylpropionate. A Novel Reagent for Stobbe-Like Condensations. *Synth Commun* 23, 2119 (1993).
76. Cui, L., Lian, J.-Q., Neoh, H.-M., Reyes, E. & Hiramatsu, K. DNA microarray-based identification of genes associated with glycopeptide resistance in *Staphylococcus aureus*. *Antimicrob. Agents Chemother.* 49, 3404-3413 (2005).
77. Neoh, H.-M. et al. Mutated response regulator graR is responsible for phenotypic conversion of *Staphylococcus aureus* from heterogeneous vancomycin-intermediate resistance to vancomycin-intermediate resistance. *Antimicrob. Agents Chemother.* 52, 45-53 (2008).
78. Engman, J., Rogstam, A., Frees, D., Ingmer, H. & Wachenfeldt, von, C. The YjbH adaptor protein enhances proteolysis of the transcriptional regulator Spx in *Staphylococcus aureus*. *J. Bacteriol.* 194, 1186-1194 (2012).
79. Kemnitz, C. R. & Loewen, M. J. 'Amide Resonance' Correlates with a Breadth of C—N Rotation Barriers. *J Am Chem Soc* 129, 2521-2528 (2007).
80. Milner-White, E. J. The partial charge of the nitrogen atom in peptide bonds. *Protein Sci.* 6, 2477-2482 (1997).

Other Embodiments

It is to be understood that while the present application has been described in conjunction with the detailed description thereof, the foregoing description is intended to illustrate and not limit the scope of the present application, which is defined by the scope of the appended claims. Other aspects, advantages, and modifications are within the scope of the following claims.

What is claimed is:
1. A compound of Formula (II):

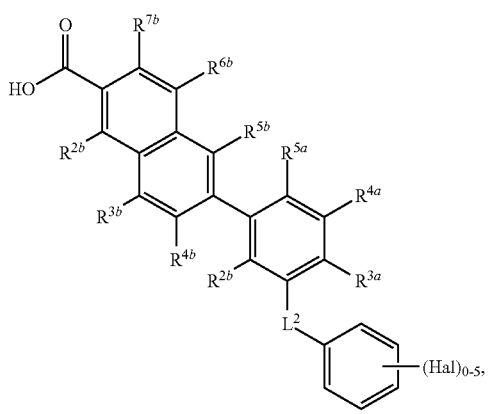

or a pharmaceutically acceptable salt thereof, wherein:
L² is $C_{1-3}$ alkylene;
each Hal is independently a halogen;
$R^{2a}$, $R^{3a}$, $R^{4a}$, and $R^{5a}$ are each independently selected from H and OH;

provided that at least one of $R^{2a}$, $R^{3a}$, $R^{4a}$, and $R^{5a}$ is OH; and
$R^{2b}$, $R^{3b}$, $R^{4b}$, $R^{5b}$, $R^{6b}$, and $R^{7b}$ are each independently selected from H, OH, HO—$C_{1-3}$ alkylene, and —C(=O)OH.

2. The compound of claim 1 having any one of the following formulae:

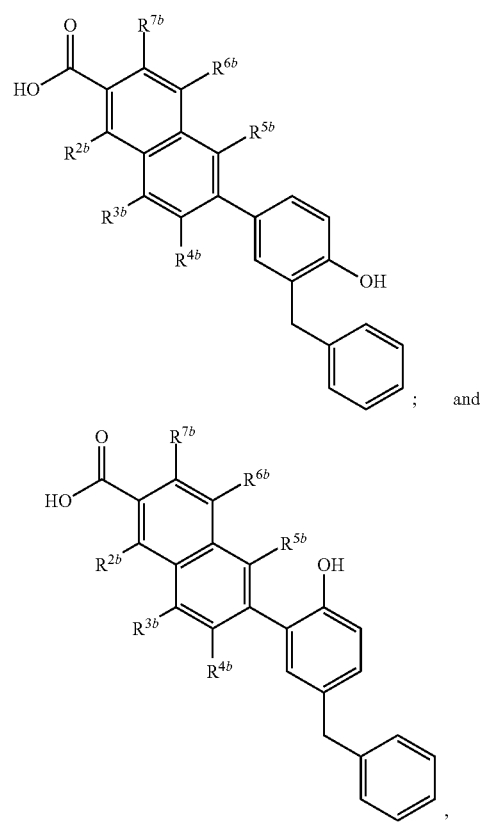

or pharmaceutically acceptable salt thereof, wherein:
wherein $R^{2b}$, $R^{3b}$, $R^{4b}$, $R^{5b}$, $R^{6b}$, and $R^{7b}$ are each independently selected from H, OH, and —C(=O)OH.

3. The compound of claim 1, wherein the compound of Formula (II) is selected from:

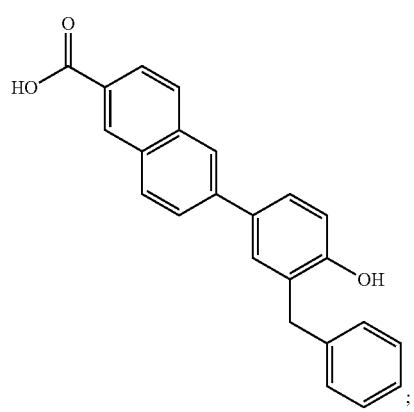

-continued

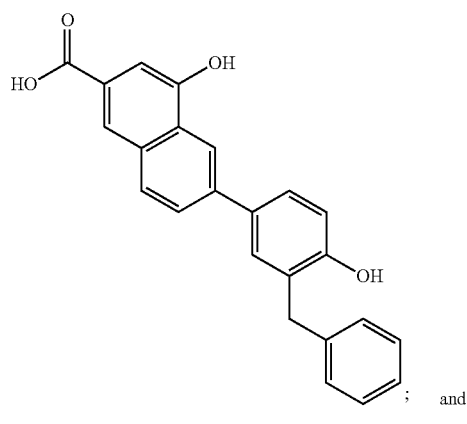

; and

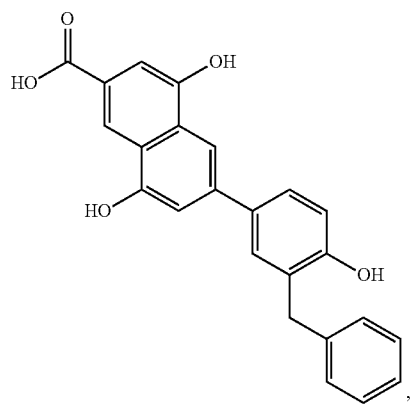

or a pharmaceutically acceptable salt thereof.

4. A compound having a formula:

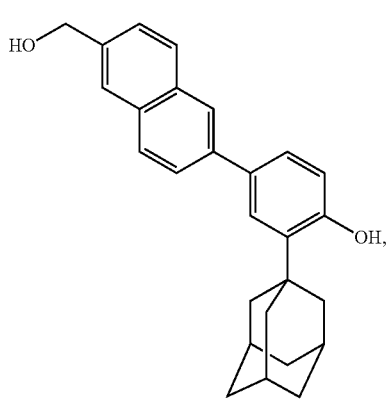 [SMILES: OCc1ccc2cc(-c3ccc(O)c(C45CC6CC(CC(C6)C4)C5)c3)ccc2c1]

or a pharmaceutically acceptable salt thereof.

5. The compound of claim 1, having formula:

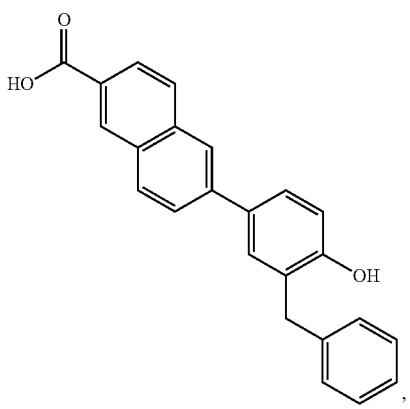 [SMILES: O=C(O)c1ccc2cc(-c3ccc(O)c(Cc4ccccc4)c3)ccc2c1]

or a pharmaceutically acceptable salt thereof.

6. The compound of claim 1, having formula:

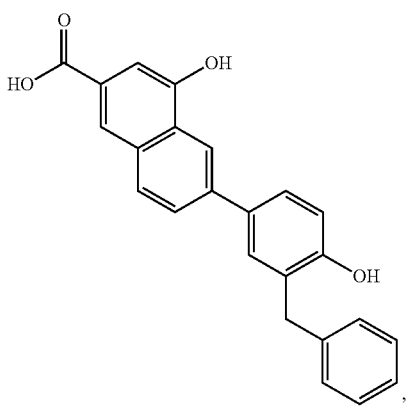 [SMILES: O=C(O)c1cc(O)c2cc(-c3ccc(O)c(Cc4ccccc4)c3)ccc2c1]

or a pharmaceutically acceptable salt thereof.

7. The compound of claim 1, having formula:

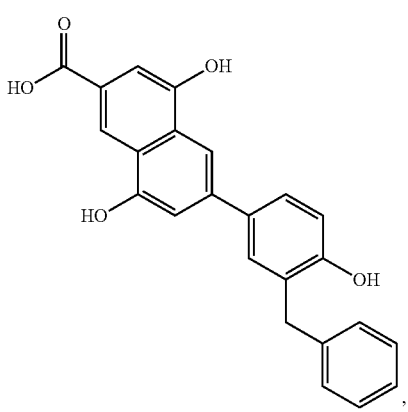 [SMILES: O=C(O)c1cc(O)c2cc(-c3ccc(O)c(Cc4ccccc4)c3)cc(O)c2c1]

or a pharmaceutically acceptable salt thereof.

* * * * *

UNITED STATES PATENT AND TRADEMARK OFFICE
CERTIFICATE OF CORRECTION

PATENT NO. : 11,278,025 B2
APPLICATION NO. : 16/614251
DATED : March 22, 2022
INVENTOR(S) : Frederick M. Ausubel et al.

Page 1 of 1

It is certified that error appears in the above-identified patent and that said Letters Patent is hereby corrected as shown below:

In the Specification

Column 1, Lines 12, replace "FEDERALLY SPONSORED RESEARCH OR DEVELOPMENT
This invention was made with Government support under Grant No. P01 A1083214 awarded by the National Institutes of Health , and Grant No. 1R35GM119426 awarded by National Institute of General Medical Sciences ."

With -- STATEMENT OF FEDERALLY SPONSORED RESEARCH
This invention was made with government support under Grant Nos. GM119426, and AI083214 awarded by the National Institutes of Health, and Grant Nos. CMMI1562904, and CBET1132446 awarded by the National Science Foundation. The government has certain rights in the invention. --

Signed and Sealed this
Twenty-third Day of May, 2023

Katherine Kelly Vidal
*Director of the United States Patent and Trademark Office*